US007922772B2

(12) United States Patent
Goble et al.

(10) Patent No.: US 7,922,772 B2
(45) Date of Patent: Apr. 12, 2011

(54) IMPLANTS AND RELATED METHODS AND APPARATUS FOR SECURING AN IMPLANT ON AN ARTICULATING SURFACE OF AN ORTHOPEDIC JOINT

(75) Inventors: E. Marlowe Goble, Alta, WY (US); Daniel F. Justin, Logan, UT (US); Joel Dever, Nibley, UT (US); Carlye J. Creger, Logan, UT (US); Daniel J. Triplett, Providence, UT (US); Robert A. Hodorek, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 922 days.

(21) Appl. No.: 10/798,665

(22) Filed: Mar. 11, 2004

(65) Prior Publication Data
US 2005/0015153 A1    Jan. 20, 2005

Related U.S. Application Data

(63) Continuation-in-part of application No. 10/749,346, filed on Dec. 30, 2003, now Pat. No. 7,771,483, and a continuation-in-part of application No. 10/444,927, filed on May 23, 2003, now Pat. No. 7,615,081.

(60) Provisional application No. 60/383,348, filed on May 24, 2002.

(51) Int. Cl.
*A61F 2/30* (2006.01)
(52) U.S. Cl. .................................................. 623/23.46
(58) Field of Classification Search ............... 623/20.14, 623/20.15, 20.21, 20.31, 20.32, 20.34, 23.44, 623/23.45, 23.46, 23.47
See application file for complete search history.

(56) References Cited

U.S. PATENT DOCUMENTS

| 3,748,662 | A | | 7/1973 | Helfet |
| 4,000,525 | A | * | 1/1977 | Klawitter et al. ............ 623/20.32 |
| 4,224,696 | A | | 9/1980 | Murray et al. |
| 4,479,271 | A | | 10/1984 | Bolesky et al. |
| 4,502,161 | A | | 3/1985 | Wall |
| 4,627,853 | A | | 12/1986 | Campbell et al. |
| 4,657,549 | A | | 4/1987 | Keller |
| 4,673,407 | A | | 6/1987 | Martin |

(Continued)

FOREIGN PATENT DOCUMENTS

DE    3 917 285    11/1990

(Continued)

OTHER PUBLICATIONS

Office Action mailed Apr. 9, 2009 in related Canadian application No. 2,490,673.*

(Continued)

*Primary Examiner* — Eduardo C Robert
*Assistant Examiner* — David Comstock
(74) *Attorney, Agent, or Firm* — Baker & Daniels LLP

(57) ABSTRACT

A method for mounting an implant at an orthopedic joint includes forming a tunnel through a bone, the tunnel having an open second end on a natural or resected articulating surface of the bone and an open first end at a location on the bone spaced apart from the natural or resected articulating surface. A fastener is advanced into the tunnel from the first end of the tunnel. The fastener, which is at least partially disposed within the tunnel, is then secured to the implant which is disposed over the second end of the tunnel.

43 Claims, 39 Drawing Sheets

U.S. PATENT DOCUMENTS

| | | | |
|---|---|---|---|
| 4,838,891 A | 6/1989 | Branemark et al. |
| 4,919,671 A | 4/1990 | Karpf |
| 4,927,421 A | 5/1990 | Goble et al. |
| 4,950,270 A | 8/1990 | Bowman et al. |
| 4,963,153 A | 10/1990 | Noesberger et al. |
| 4,964,868 A | 10/1990 | Bloebaum |
| 5,019,103 A | 5/1991 | Van Zile et al. |
| 5,035,699 A | 7/1991 | Coates |
| 5,037,439 A | 8/1991 | Albrektsson et al. |
| 5,092,895 A | 3/1992 | Albrektsson et al. |
| 5,100,409 A | 3/1992 | Coates et al. |
| 5,176,684 A | 1/1993 | Ferrante et al. |
| 5,180,383 A | 1/1993 | Haydon |
| 5,258,015 A | 11/1993 | Li et al. |
| 5,282,868 A | 2/1994 | Bahler |
| 5,346,496 A | 9/1994 | Pennig |
| 5,474,559 A | 12/1995 | Bertin et al. |
| 5,489,311 A | 2/1996 | Cipolletti |
| 5,507,812 A | 4/1996 | Moore |
| 5,549,683 A | 8/1996 | Bonutti |
| 5,569,259 A | 10/1996 | Ferrante et al. |
| 5,571,196 A | 11/1996 | Stein |
| 5,571,203 A * | 11/1996 | Masini ........................ 623/22.46 |
| 5,593,411 A | 1/1997 | Stalcup et al. |
| 5,634,927 A | 6/1997 | Houston et al. |
| 5,674,224 A | 10/1997 | Howell et al. |
| 5,702,397 A | 12/1997 | Goble et al. |
| 5,702,459 A | 12/1997 | Hummer et al. |
| 5,709,689 A | 1/1998 | Ferrante et al. |
| 5,741,262 A | 4/1998 | Albrektsson et al. |
| 5,743,915 A | 4/1998 | Bertin et al. |
| 5,746,771 A | 5/1998 | Clement, Jr. et al. |
| 5,755,800 A | 5/1998 | O'Neil et al. |
| 5,755,803 A | 5/1998 | Haines et al. |
| 5,766,255 A | 6/1998 | Slamin et al. |
| 5,769,855 A | 6/1998 | Bertin et al. |
| 5,776,201 A | 7/1998 | Colleran et al. |
| 5,782,924 A | 7/1998 | Johnson |
| 5,800,553 A | 9/1998 | Albrektsson et al. |
| 5,824,098 A | 10/1998 | Stein |
| 5,860,981 A | 1/1999 | Bertin et al. |
| 5,879,391 A | 3/1999 | Slamin |
| 5,885,035 A | 3/1999 | Hoffschneider |
| 5,968,045 A | 10/1999 | Frazier |
| 6,068,648 A | 5/2000 | Cole et al. |
| 6,071,311 A | 6/2000 | O'Neil et al. |
| 6,102,954 A | 8/2000 | Albrektsson et al. |
| 6,132,468 A | 10/2000 | Mansmann |
| 6,162,234 A | 12/2000 | Freedland et al. |
| 6,168,629 B1 | 1/2001 | Timoteo |
| 6,171,342 B1 | 1/2001 | O'Neil et al. |
| 6,245,110 B1 | 6/2001 | Grundei et al. |
| 6,299,645 B1 | 10/2001 | Ogden |
| 6,319,271 B1 | 11/2001 | Schwartz et al. |
| 6,368,326 B1 | 4/2002 | Dakin et al. |
| 6,436,101 B1 | 8/2002 | Hamada |
| 6,461,373 B2 | 10/2002 | Wyman et al. |
| 6,508,841 B2 | 1/2003 | Martin et al. |
| 6,520,964 B2 | 2/2003 | Tallarida et al. |
| 6,544,267 B1 | 4/2003 | Cole et al. |
| 6,554,838 B2 | 4/2003 | McGovern et al. |
| 6,610,067 B2 | 8/2003 | Tallarida et al. |
| 6,652,587 B2 | 11/2003 | Felt et al. |
| 6,679,917 B2 | 1/2004 | Ek |
| 6,736,819 B2 | 5/2004 | Tiirneni |
| 6,773,461 B2 | 8/2004 | Meyers |
| 6,866,683 B2 | 3/2005 | Gerbec et al. |
| 6,905,514 B2 | 6/2005 | Carignan et al. |
| 6,969,393 B2 | 11/2005 | Pinczewski et al. |
| 6,994,725 B1 | 2/2006 | Goble |
| 7,150,761 B2 | 12/2006 | Justin et al. |
| 7,250,061 B2 | 7/2007 | Jacobsson et al. |
| 2002/0019637 A1 | 2/2002 | Frey et al. |
| 2002/0055783 A1 | 5/2002 | Tallarida et al. |
| 2002/0107520 A1 | 8/2002 | Hoffman |
| 2002/0138150 A1 | 9/2002 | Leclercq |
| 2002/0147498 A1 | 10/2002 | Tallarida et al. |
| 2002/0198528 A1 | 12/2002 | Engh et al. |
| 2003/0033018 A1 | 1/2003 | Stolowitz et al. |
| 2003/0060887 A1 | 3/2003 | Ek |
| 2003/0120276 A1 | 6/2003 | Tallarida et al. |
| 2003/0158606 A1 | 8/2003 | Coon et al. |
| 2003/0225456 A1 | 12/2003 | Ek |
| 2003/0225457 A1 | 12/2003 | Justin et al. |
| 2004/0015170 A1 | 1/2004 | Tallarida et al. |
| 2004/0106928 A1 | 6/2004 | Ek |
| 2004/0148030 A1 | 7/2004 | Ek |
| 2005/0137708 A1 | 6/2005 | Clark |
| 2005/0143831 A1 | 6/2005 | Justin et al. |
| 2005/0149044 A1 | 7/2005 | Justin et al. |
| 2005/0154398 A1 | 7/2005 | Miniaci et al. |
| 2005/0177242 A1 | 8/2005 | Lotke |
| 2006/0004461 A1 | 1/2006 | Justin et al. |

FOREIGN PATENT DOCUMENTS

| | | |
|---|---|---|
| EP | 0 336 774 B1 | 10/1989 |
| EP | 0 714 645 B1 | 6/1996 |
| EP | 0 850 606 A2 | 7/1998 |
| EP | 0 980 679 A2 | 2/2000 |
| EP | 0 985 386 A2 | 3/2000 |
| FR | 2 521 421 | 11/1975 |
| FR | 2 521 421 A1 | 8/1983 |
| FR | 2 630 639 | 3/1988 |
| FR | 2 682 589 | 4/1993 |
| FR | 2 718 953 | 10/1995 |
| GB | 2 007 980 A | 5/1979 |
| WO | WO 89/09578 A1 | 10/1989 |
| WO | WO 89/11837 | 12/1989 |
| WO | WO 91/06260 | 5/1991 |
| WO | WO 94/09723 | 5/1994 |
| WO | WO 01/28457 A1 | 4/2001 |
| WO | WO 01/66021 A1 | 9/2001 |
| WO | WO 01/66022 A1 | 9/2001 |
| WO | WO 03/051210 A2 | 6/2003 |
| WO | WO 03/051211 A1 | 6/2003 |
| WO | WO 03/099159 A2 | 12/2003 |
| WO | WO 2005/069809 A3 | 8/2005 |

OTHER PUBLICATIONS

Response filed Oct. 8, 2009 to the Office Action mailed Apr. 9, 2009 in related Canadian application No. 2,490,673.*
Office Action mailed Nov. 3, 2005 in U.S. Appl. No. 10/749,346.
Response/Amendment to Office Action filed Jan. 30, 2006 in U.S. Appl. No. 10/749,346.
Office Action mailed Apr. 12, 2006 in U.S. Appl. No. 10/749,346.
Response/Amendment to Office Action filed Aug. 14, 2006 in U.S. Appl. No. 10/749,346.
Office Action mailed Oct. 20, 2006 in U.S. Appl. No. 10/749,346.
Response/Amendment to Office Action filed Jan. 23, 2007 in U.S. Appl. No. 10/749,346.
Office Action mailed Apr. 16, 2007 in U.S. Appl. No. 10/749,346.
Response/Amendment to Office Action filed May 31, 2007 in U.S. Appl. No. 10/749,346.
Advisory Action mailed Jul. 1, 2007 in U.S. Appl. No. 10/749,346.
Response/Amendment to Office Action filed Oct. 9, 2007 in U.S. Appl. No. 10/749,346.
Office Action mailed Dec. 10, 2007 in U.S. Appl. No. 10/749,346.
Response/Amendment to Office Action filed Jun. 5, 2008 in U.S. Appl. No. 10/749,346.
Office Action mailed Aug. 13, 2008 in U.S. Appl. No. 10/749,346.
Response/Amendment to Office Action filed Nov. 25, 2007 in U.S. Appl. No. 10/749,346.
Advisory Action mailed Dec. 12, 2008 in U.S. Appl. No. 10/749,346.
Response/Amendment to Office Action filed Jan. 13, 2009 in U.S. Appl. No. 10/749,346.
Office Action mailed Dec. 27, 2007 in U.S. Appl. No. 11/219,098.
Response/Amendment to Office Action filed May 20, 2008 in U.S. Appl. No. 11/219,098.

* cited by examiner

IMPLANTS AND RELATED METHODS AND APPARATUS FOR SECURING AN IMPLANT ON AN ARTICULATING SURFACE OF AN ORTHOPEDIC JOINT

CROSS-REFERENCE TO RELATED APPLICATIONS

The present application is a continuation-in-part of U.S. patent application Ser. No. 10/749,346, filed Dec. 30, 2003, now U.S. Pat. No. 7,771,483, and is a continuation-in-part of U.S. patent application Ser. No. 10/444,927, filed May 23, 2003, now U.S. Pat. No. 7,615,081, which claims priority to U.S. Provisional Application Ser. No. 60/383,348, filed May 24, 2002, which applications are incorporated herein by specific reference.

BACKGROUND OF THE INVENTION

1. The Field of the Invention

The present invention relates to implants and related methods and apparatus for mounting such implants on an articulating surface of an orthopedic joint of a patient.

2. The Relevant Technology

The human body has a variety of movable orthopedic joints such as the knee joint, hip joint, shoulder joint, and the like. These joints are formed by the intersection of two bones. The intersecting end of each bone has smooth articular surface that is comprised of cartilage. As a result of injury, wear, arthritis, disease or other causes, it is occasionally necessary to replace all or part of an orthopedic joint with an artificial implant. This procedure is referred to as a joint replacement or arthroplasty. For example, a total knee arthroplasty comprises cutting off or resecting the articular surfaces at both the distal end of the femur and the proximal end of the tibia. Complementary artificial implants are then mounted on the distal end of the femur and the proximal end of the tibia. Where only a portion of a joint is damaged, a partial joint arthroplasty can be performed. In this procedure, one or more artificial implants replace only a portion of a joint.

Although joint replacement is now a common procedure that has met with popular success, conventional implants and related mounting techniques have significant shortcomings. One significant drawback to many joint replacements is the extended and painful patient recovery. For example, a traditional knee replacement requires an open procedure wherein a relatively large incision is made which severs a portion of the muscle bounding the femur. The large incision is made so as to fully expose the respective ends of the femur and tibia.

This exposure is necessary when using conventional techniques to resect the femur and tibia and to mount the implants. For example, some conventional tibial implants are screwed directly into the resected end face of the tibia. Mounting such screws requires exposure of the resected end face. In yet other embodiments, the implants are formed with posts projecting therefrom. The posts are received within sockets formed on the resected end face of the tibia and femur. Again, forming of the sockets and inserting the posts into the sockets requires substantially full expose of the resected end face of the tibia and femur.

In general, the more invasive the surgery, the more painful, difficult, and time consuming the patient recovery. This is largely due to the significant amount of scar tissue produced the by incision and resection of various soft tissues. Furthermore, such open and invasive surgeries have a greater risk of infection.

Another problem with conventional joint implants and related techniques for mounting is that it can be difficult to fit, adjust, and/or exchange different implants during the fitting stage. That is, implants come in a variety of different sizes, shapes, and configurations. During the joint replacement procedure, the surgeon may often test a variety of different sized implants to determine the best fit and alignment. As conventional implants are screwed into or pounded onto the bone during placement, the fitting, adjustment, and/or replacement of different conventional implants can be difficult and potentially damaging to the bone. Likewise, it can often be difficult to replace worn or damaged implants.

Accordingly, what is needed are implants and related methods and systems for preparing an articular surface of a joint and mounting an implant thereat which minimizes the length of incision, the amount of bone resection, and/or the impact on soft tissue. What is also needed are implants and related methods and systems which enable easier fitting, alignment, testing, and/or replacement of implants.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
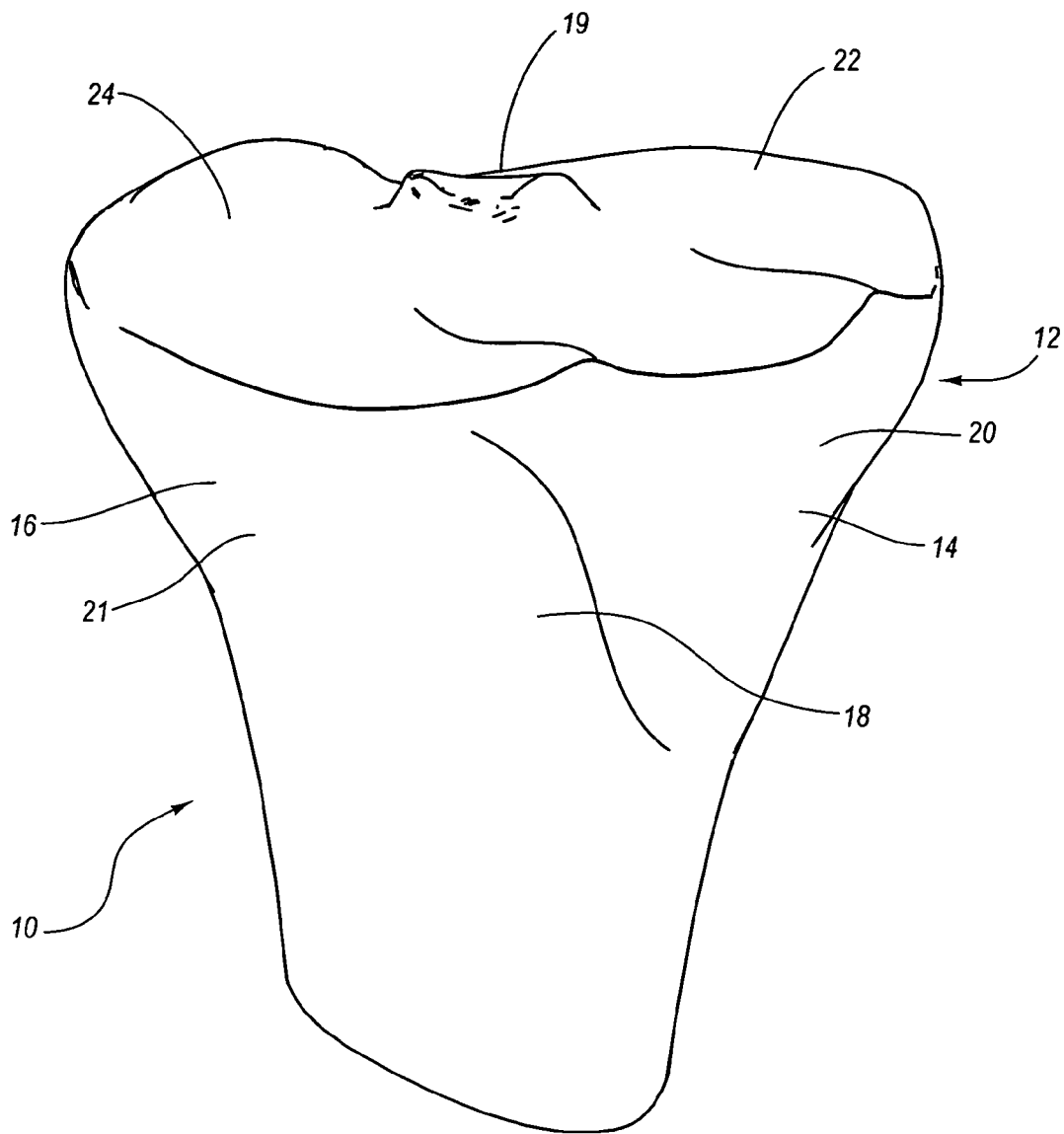
FIG. 1 is a perspective view of the proximal end of a tibia.

The present invention relates to methods and apparatus for preparing an articulating surface of an orthopedic joint to receive an implant, implants for mounting at an articulating surface of an orthopedic joint, anchoring systems for securing an implant at an articulating surface of an orthopedic joint, and related methods and instruments. As used in the specification and appended claims, the terms "articulating surface" and "natural articulating surface" are broadly intended to include all natural articular surfaces of a bone forming a portion of an orthopedic joint and all articulating wear surfaces of a bone forming a portion of an orthopedic joint which are produced as a result of ware, trauma, disease, or other causes which remove all or a portion of the natural articular surface.

The implants, anchoring systems, instruments, and methods of the present invention can be used in combination to mount an inventive implant or can be used separately or in combinations with other conventional implants, anchoring systems, instruments and/or methods. It is appreciated that the implants, anchoring systems, instruments, and methods of the present invention can be used for mounting an implant on virtually any articulating surface of any orthopedic joint in a human or other mammal. By way of example and not by limitation, the implants, anchoring systems, instruments, and methods of the present invention can be used in association with resurfacing an articulating surface of a knee joint, ankle joint, hip joint, shoulder joint, elbow joint, wrist joint, interphalangeal joint, or other joints. As such, the implants can be mounted on the proximal end and distal end of the femur, tibia, humerus, radius, and ulna, and on the articular surfaces of the scapula, pelvis, bones within the foot and hand, and other bone articular surfaces. Likewise, the implants, anchoring systems, instruments, and methods of the present invention can be used in facilitating a partial joint arthroplasty or a total joint arthroplasty.

In one embodiment, the implants, anchoring systems, instruments, and/or methods of the present invention are designed so that an articulating surface of a joint can be prepared and an implant mounted thereon using procedures that are minimally invasive. As a result, recovery time is significantly improved while the damage to soft tissue if decreased and the risk of infection minimized. Also in one embodiment of the present invention, the implants, anchoring systems, instruments, and/or methods are designed so that the implant can be selectively adjusted, tightened, and/or loosened after the implant is positioned on the articulating surface. This ability allows for greater ease in adjustment and fitting of an implant at the time of initial placement and for greater easy in replacement of an implant.

Set forth below are several embodiments of the present invention used in association with preparing an articulating surface at a proximal end of a tibia and mounting a condylar implant at the proximal end of the tibia. It is again noted that these embodiments are only given by way of example and that one skilled in the art based on the teaching provided herein would be able to use corresponding implants, methods, and instruments to prepare and/or mount an implant on other joint articulating surfaces.

Depicted in FIG. 1 is a proximal end 10 of a tibia 12. Proximal end 10 has a lateral side 14 and a medial side 16 which each extend between an anterior side 18 and a posterior side 19. Proximal end 10 further comprises a lateral condyle 20 and a medial condyle 21. Lateral condyle 20 terminates proximally at a lateral facet 22 of a superior articular surface of tibia 12 while medial condyle 21 terminates proximally at medial facet 24 of a superior articular surface of tibia 12.

Although tibia 12 shown in FIG. 1 is from a left leg, it is appreciated that the tibia of the right leg has a complimentary configuration and that the methods and apparatus of this specific example are equally applicable thereto. Furthermore, the methods and apparatus of this example are primarily illustrated in association with medial condyle 21 of tibia 12. It is also appreciated that the methods and apparatus can be used in association with lateral condyle 20.

In one embodiment, to facilitate mounting of a condylar implant on medial condyle 21, conventional arthroscopic procedures are used to resect the posterior portion of the medial meniscus. Once the posterior portion of the medial meniscus is removed, a vertical or horizontal incision, generally in a range between about 2 cm to about 6 cm, is formed over the anterior side of the medial meniscus. Following retraction of the surrounding tissue, the anterior side of the medial meniscus is resected. A coarse rasp is then inserted between the medial condyle of the femur and medial condyle 21 of tibia 12. The rasp is used to remove approximately 1-2 mm of articular cartilage on medial facet 24 of tibia 12. Removal of the meniscus and the articular cartilage provides increased access to medial facet 24 of tibia 12.

Figure 2:
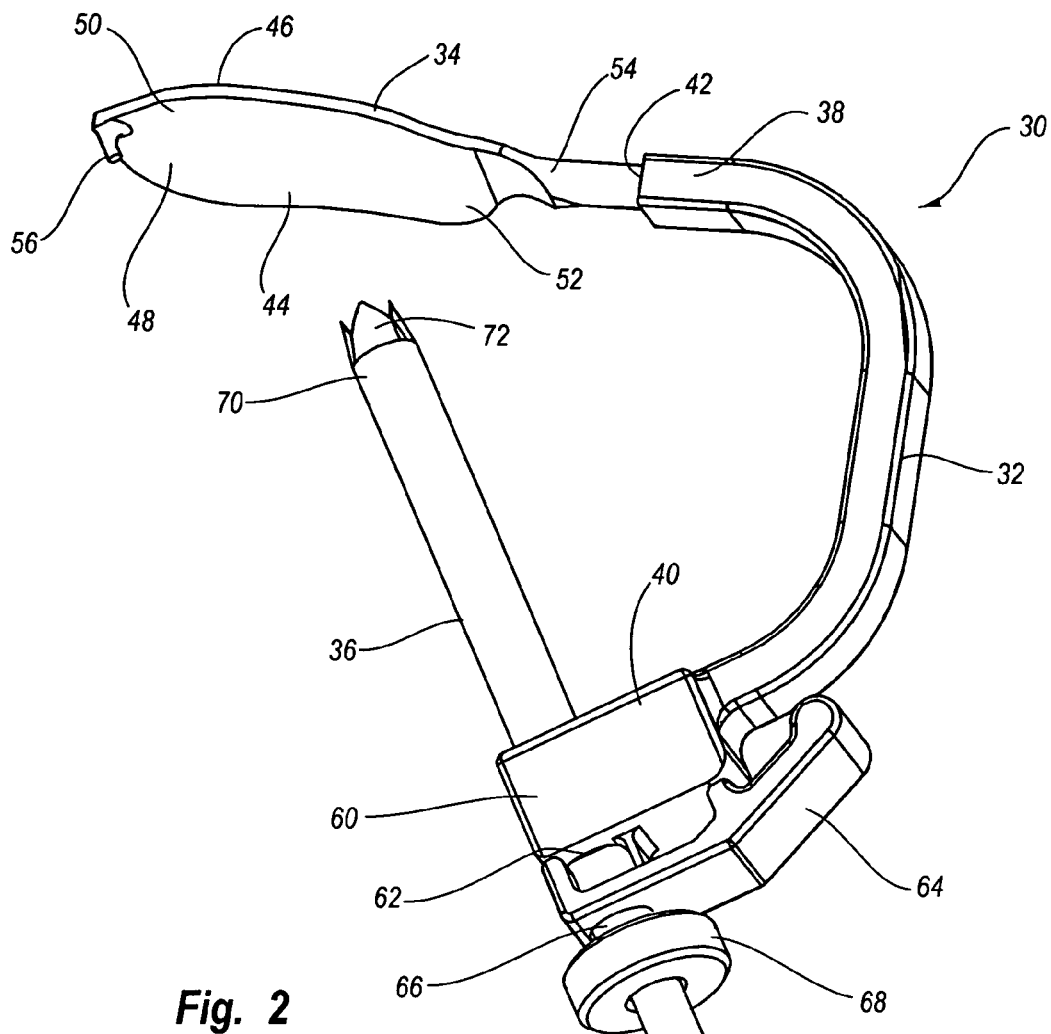
FIG. 2 is a perspective view of a guide assembly for forming a tunnel on the proximal end of the tibia shown in FIG. 1.

Depicted in FIG. 2 is one embodiment of a guide assembly 30 which is now used for forming a tunnel through a portion of tibia 12. As discussed below in greater detail, the tunnel can be used for preparing tibia 12 for a condylar implant and/or securing a condylar implant to tibia 12. In general, guide assembly 30 includes a substantially U-shaped guide brace 32 having a template 34 and a tubular guide sleeve 36 mounted on opposing ends thereof. More specifically, guide brace 32 has a first end 38 and an opposing second end 40. Recessed in first end 38 is a socket 42.

Template 34 comprises a low profile base plate 44 having a top surface 46 and an opposing bottom surface 48 which each extend between a first end 50 and an opposing second end 52. Although not required, in one embodiment bottom surface 48 has a configuration generally complementary to medial facet 24 of the superior auricular surface of tibia 12. Base plate 44 typically has a maximum thickness extending between surfaces 46 and 48 in a range between about 1 mm to about 4 mm. Projecting from second 52 of base plate 44 is a stem 54. Stem 54 is configured to be slidably received within socket 42 of guide brace 32. A projection 56 downwardly extends from bottom surface 48 of base plate 44 at first end 50. As depicted, projection 56 has the configuration of a narrow finger. In other embodiments, projection 56 can comprise an elongated ridge or other configurations.

Formed on second end 40 of guide brace 32 is an enlarged housing 60 having a passage 62 extending therethrough. A resiliently flexible clamp arm 64 is mounted to housing 60. An aperture 66 extends through clamp arm 64 in general alignment with passage 62.

Tubular guide sleeve 36 slidably extends through passage 62 and aperture 66. Guide sleeve 36 has a proximal end 68 and an opposing distal end 70. A plurality of sharpened teeth 72 are formed at distal end 70. By pressing clamp arm 64 toward housing 60, passage 62 and aperture 66 are aligned allowing guide sleeve 36 to freely slide within passage 62 and aperture 66 to a desired location. As clamp arm 56 is released, clamp arm 56 resiliently biases away from housing 60 so as to bind guide sleeve 36, thereby securing guide sleeve 36 in the desired location. In alternative embodiments, it is appreciated that clamp arm 64 can be replaced with a set screw, clamp, or a variety of other types of fasteners that can be used to selectively secure guide sleeve 36 to second end 40 of guide brace 32.

Figure 3:
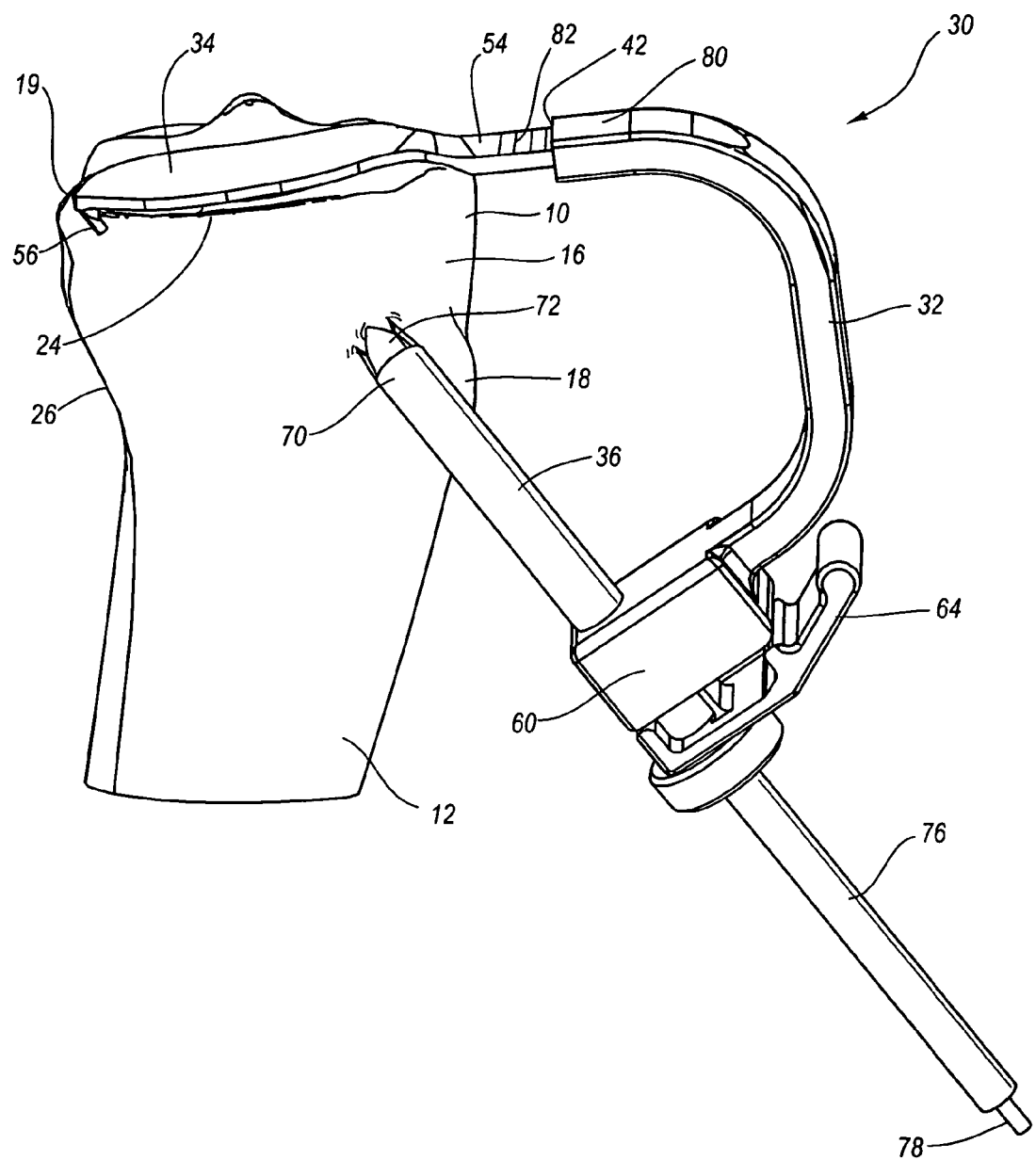
FIG. 3 is a perspective view showing the guide assembly in FIG. 2 mounted on the tibia of FIG. 1.

During use, as depicted in FIG. 3, template 34 is slid over medial facet 24 of tibia 12, i.e., the articulating surface, so that projection finger 56 catches on posterior side 19 of tibia 12. Projection finger 56 thus facilitates proper positioning of template 34 and also helps to retain template 34 on medial facet 24. It is appreciated that the size and shape of the lateral and medial facets of the superior articular surfaces of the tibia varies between different patients. As such, the present invention comprises a plurality of alternative templates 34 which are configured for placement on one of the lateral and medial facet and which each have a different configuration. As such a number of the alternative templates 34 can be initially test fitted to determine one that has a best fit for a particular patient.

Figure 2A:
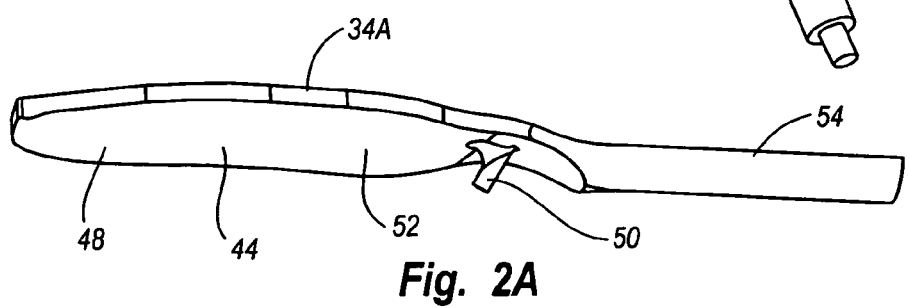
FIG. 2A is a perspective view of an alternative template used with the guide assembly shown in FIG. 2.

For example, depicted in FIG. 2A is one alternative template 34A that is smaller than template 34. Like elements between templates 34 and 34A are identified by like reference characters. In further contrast to template 34, template 34A has a projection 56A downwardly extending from second end 52 of base plate 44. Projection 56A thus biases against anterior side 18 or medial side 16 of tibia 12 to help properly position template 34A. In yet other embodiments, in contrast to positioning the projection on one of the opposing ends of base plate 44, the projection can be positioned along one of the opposing sides of base plate 44 so as to bias against lateral side 14 (when used on lateral facet 22) or bias against medial side 16 of tibia 12.

Once template 34 is selected and properly positioned on medial facet 24, tubular guide sleeve 36 is advanced within housing 60 so that teeth 72 at distal end 70 bias against medial side 16 of proximal end 10 of tibia 12. As such, tubular guide sleeve 36 biases against tibia 12 at a location spaced apart from the articulating surface of medial facet 24. Guide sleeve 36 is then secured in place by releasing clamp arm 64. By securing guide sleeve 36 against tibia 12, guide assembly 30 is clamped onto tibia 12. In one alternative embodiment, guide sleeve 36 can be biased against anterior side 18 of tibia 12.

Next, a tubular drill sleeve 76 is inserted into tubular guide sleeve 60. Positioned within drill sleeve 76 is a guide wire 78. Using drill sleeve 76 as a guide, guide wire 78 is drilled through tibia 12 until guide wire 78 reaches template 34, thereby forming a guide tunnel. In part, template 34 functions as a shield to prevent guide wire 78 and/or other drill tools from accidentally contacting and damaging the femur. In other embodiments, a hole or recess is formed on template 34. Guide wire 78 can passed through or into the hole or recess to ensure complete formation of the tunnel on medial facet 24.

Once the guide tunnel is formed, guide wire 78 and drill sleeve 76 are removed from guide sleeve 60. A larger drill tool, not show, such as a larger guide wire, drill bit, or the like is then passed through guide sleeve 60 and drilled through tibia 12 along the guide tunnel to form a final tunnel 90 (FIG. 4) through tibia 12. It is appreciated that any number of progressively larger drill tools can be used. In alternative embodiments guide wire 78 and drill sleeve 76 can be eliminated. A single larger drill tool can then be used to form tunnel 90 in a single pass. Using a sequence of larger drill tools, however, helps ensure proper placement of tunnel 90 and facilitates forming the opening of the tunnel adjacent to template 34.

As discussed below in greater detail, the angular orientation of tunnel 90 is typically held constant and is based on the configuration of the implant. However, depending on the amount of bone needed to be resected for mounting the condylar implant, it may be necessary to shift the position of tunnel 90 posterior or anterior. Shifting the position of tunnel 90 posterior-anterior is accomplished by selectively moving stem 54 of template 34 further into or further out of socket 42 of guide brace 32. Once template 34 and guide brace 32 are positioned at their relative positions, a set screw 80 is tightened so as to secure template 34 and guide brace 32 together.

Predefined markings 82 are formed on stem 54 to help define the relative positioning between template 34 and guide brace 32.

Figure 4:
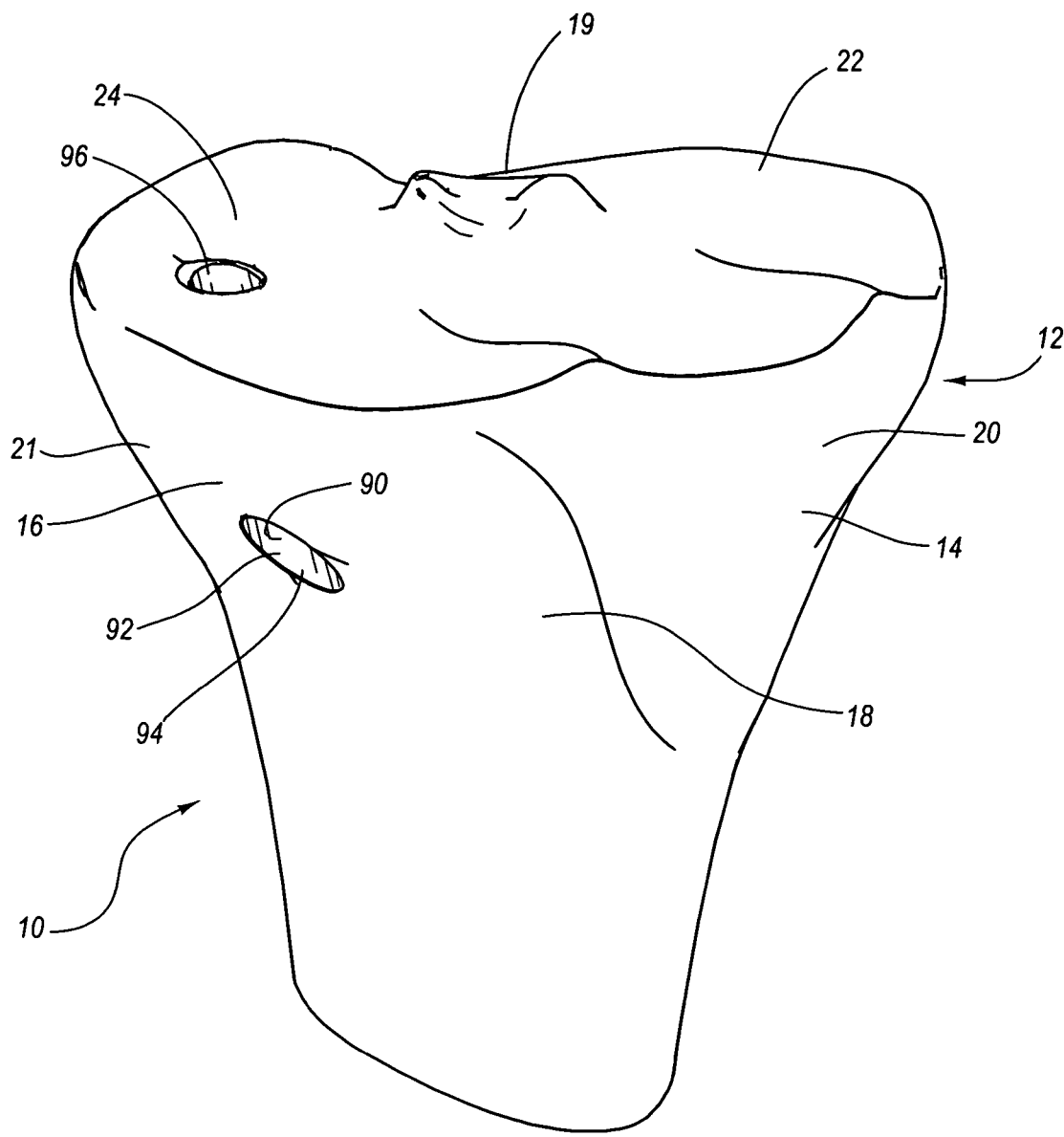
FIG. 4 is a perspective view of the tibia shown in FIG. 1 having a tunnel formed thereon.

Once tunnel 90 is formed, guide assembly 30 is removed so as to produce tibia 12 shown in FIG. 4. As depicted, tunnel 90 has an interior surface 92 that extends from a first end 94 to an opposing end second end 96. First end 94 is formed on medial side 16 of proximal end 10 of tibia 12. Second end 96 is formed on medial facet 24 of tibia 12. Expressed in other terms, second end 96 of tunnel 90 is formed on a section of an articulating surface, i.e., medial facet 24, while first end 94 is at a location on tibia 12 that is spaced apart from the articulating surface. Although tunnel 90 can be any desired size, in one embodiment tunnel 90 has a diameter in a range between about 5 mm to about 10 mm.

Using the above discussed methods and instruments, tunnel 90 is formed by procedures that are minimally invasive to the patient. As discussed below in greater detail, once tunnel 90 is formed, tunnel 90 can then be used to assist in the resection of medial fact 24 and/or the mounting of a condylar implant on the resected medial facet 24. Furthermore, by using tunnel 90 the resection of medial facet 24 and the mounting of the condylar implant can also be performed using procedures that are minimally invasive.

Figure 5:
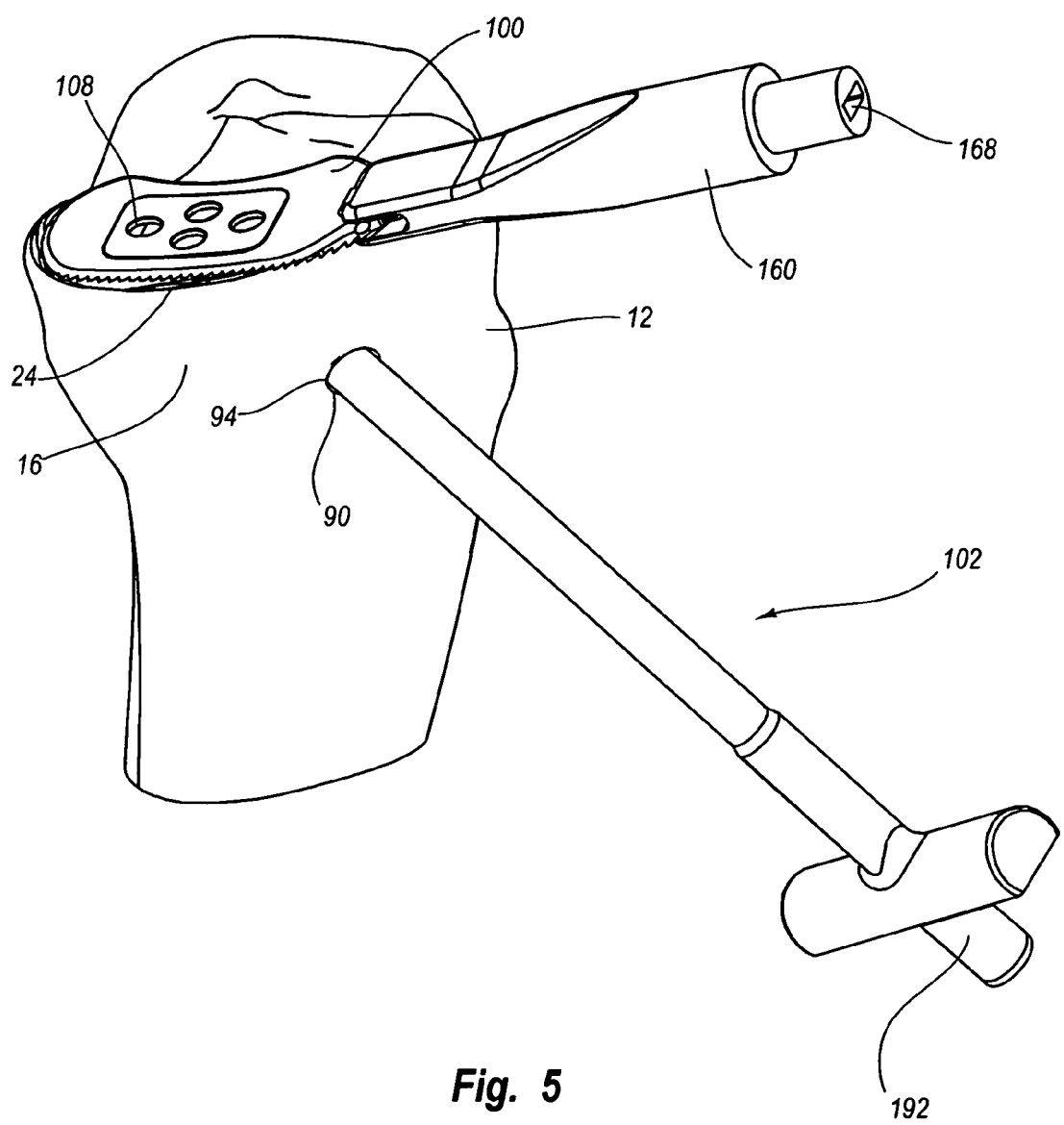
FIG. 5 is a perspective view of a rasp assembly resecting the tibia of FIG. 4.

Although not required, in one embodiment as mentioned above tunnel 90 is used in the resection of tibia 12 for preparing tibia 12 to receive a condylar implant. The resection of tibia 12 can be accomplished using a number of different procedures. For example, as depicted in FIG. 5, is one embodiment of a rasp assembly 100 is used in association with a retention rod 102 to facilitate resection of tibia 12.

Figure 6:
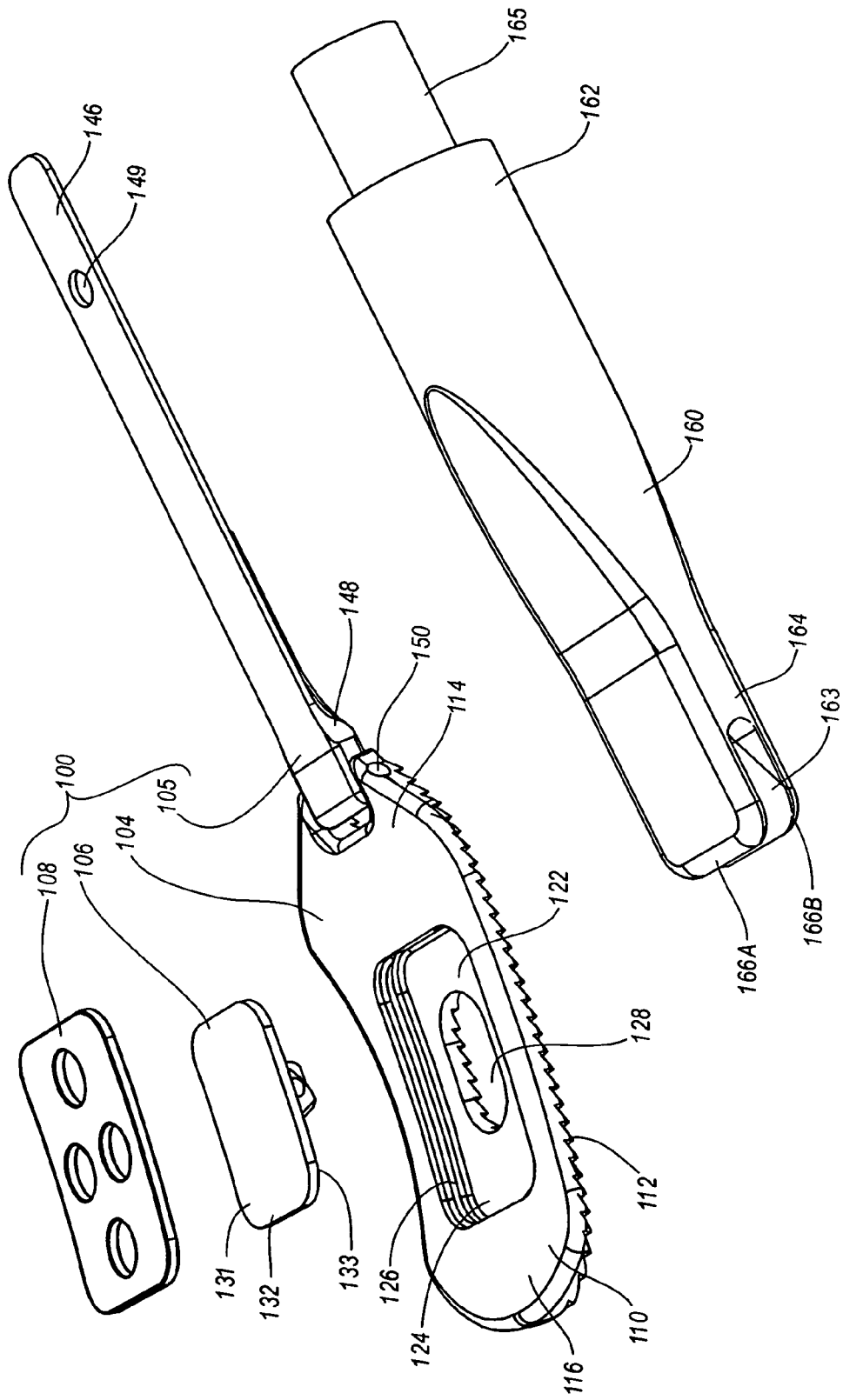
FIG. 6 is a top perspective view of the raps assembly shown in FIG. 5.
Figure 7:
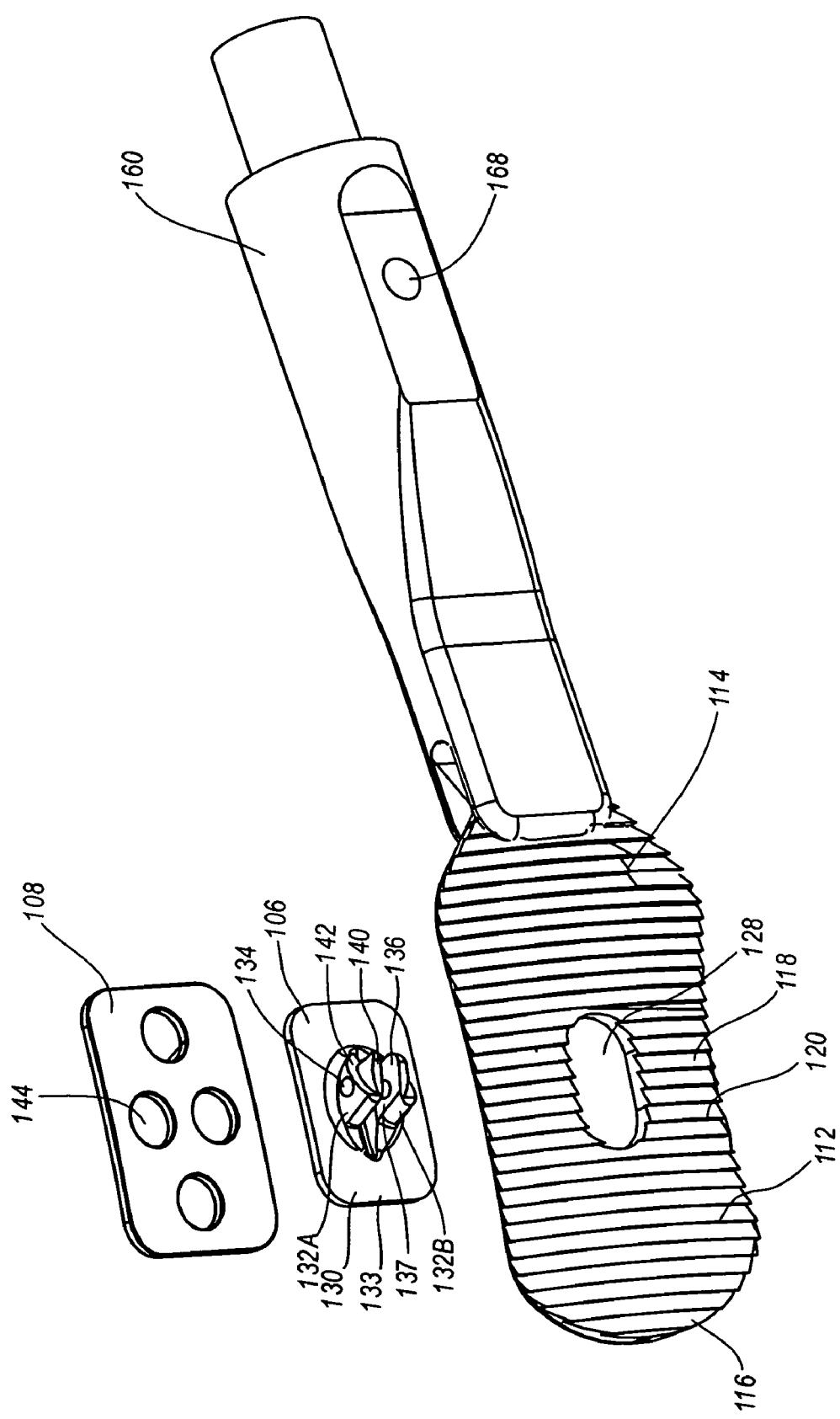
FIG. 7 is a bottom perspective view of the rasp assembly shown in FIG. 6.

As depicted in FIG. 6, rasp assembly 100 comprises a rasp body 104 having a pivot arm 105 mounted thereon, a rasp guide 106, and a cover plate 108. More specifically, as depicted in FIGS. 6 and 7, rasp body 104 has a top surface 110 and an opposing bottom surface 112 that each extend between a proximal end 114 and an opposing distal end 116. Transversely extending across bottom surface 112 are a plurality of ridges 118 that each terminate at a sharpened cutting edge 120. It is appreciated that ridges 118 and cutting edges 120 can be at any desired orientation or combination of different orientation that facilitate cutting. Bottom surface 112 is configured such that reciprocating movement of bottom surface 112 on tibia 12 produces a recess on tibia 12 that can receive a desired implant. Recessed on top surface 110 of rasp body 104 is a guide slot 122. Guide slot 122 is bounded by a floor 124 and a sidewall 126 upstanding from floor 124. Extending through floor 124 to bottom surface 112 is an opening 128.

Rasp guide 106 comprises a slide plate 130 having a top surface 131 and an opposing bottom surface 133. Downwardly projecting from bottom surface 133 are a pair of spaced apart forks 132A and 132B with a pin 134 extending therebetween. Forks 132A and B have facing interior surfaces 136 which bound a gap 137 and have opposing exterior surfaces 138. Forks 132A and B terminate at a free terminus 140. Exterior surface 138 of each fork 132A and B is recessed at terminus 140 such that a sloping shoulder 142 is formed on each fork 132A and B.

Rasp guide 106 is received within guide slot 122 so that forks 132A and B project through opening 128. Rasp guide 106 is slightly smaller than guide slot 122 such that forks 132A and B are free to reciprocate within opening 128 as slide plate 130 reciprocates within guide slot 122. As shown in FIG. 5, cover plate 108 is secured within guide slot 122 so as to retain rasp guide 106 within guide slot 122. Cover plate 108 can be mounted using conventional techniques such as welding, press fit, and the like. Holes 144 are formed through cover plate 108 to prevent unwanted build-up of resected bone particles within guide slot 122.

As depicted in FIG. 6, pivot arm 105 has a proximal end 146 and an opposing distal end 148. A set hole 149 extends through pivot arm 105 toward proximal end 146. Distal end 148 of arm 105 is hingedly mounted to proximal end 114 of rasp body 104 by a pin 150.

In one embodiment, an insertion handle 160 is used to place rasp body 104 over medial facet 24 of tibia 12. Insertion handle 160 has a proximal end 162 and an opposing distal end 164. A post 165 is formed a proximal end 162. Post 165 is adapted to receive an extension handle if desired. A pair of spaced apart lips 166A and B project from distal end 164 and bound a slot 163. A channel 168 (FIG. 5) longitudinally extends through insertion handle 160 so as to communicate with slot 163. Channel 168 is configured to receive pivot arm 105 when rasp body 104 is received within slot 163.

During use, pivot arm 105 is slid into channel 165 from between lips 166A and B. Lips 166A and B are then advanced to extend above and below proximal end 114 of rasp body 104. A set screw 168 (FIG. 7) is then advanced into insertion handle 160 so as to extend through set hole 149 on pivot arm 105. In this configuration insertion handle 160 rigidly supports rasp body 104 so as to prevent hinged movement of rasp body 104 during insertion.

Figure 8:
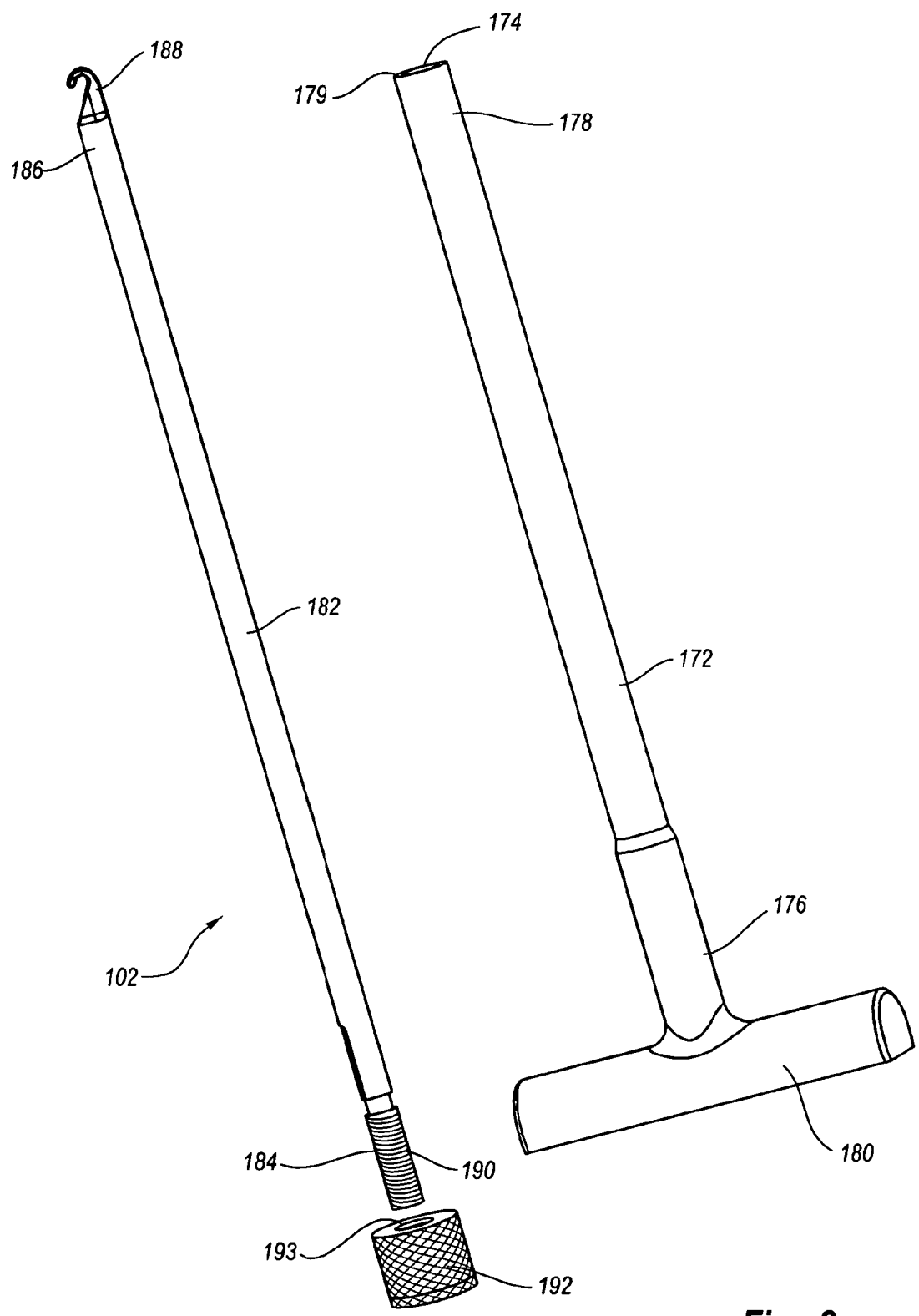
FIG. 8 is an exploded perspective view of the retention rod shown in FIG. 5.

Turning to FIG. 8, retention rod 102 comprises a tubular set rod 172 bounding a channel 174 extending from a proximal end 176 to an opposing distal end 178. Distal end 178 terminates at a distal end face 179. A handle 180 outwardly projects from proximal end 176 to facilitating grasping retention rod 102.

Retention rod 102 further comprises a hook rod 182. Hook rod 182 has a proximal end 184 and an opposing distal end 186. Projecting from distal end 186 is a hook 188. Threads 190 are formed on proximal end 184. A knob 192 is also provided having a threaded port 193. Threads 190 on hook rod 182 are configured to mate with threaded port 193 of knob 192. Hook rod 182 is received within channel 174 of set rod 172 such that knob 192 biases against handle 180 and hook 188 extends beyond distal end face 179. In this configuration, rotation of knob 192 relative to hook rod 182 causes hook 188 to extend or retract relative to set rod 172.

Figure 9A:
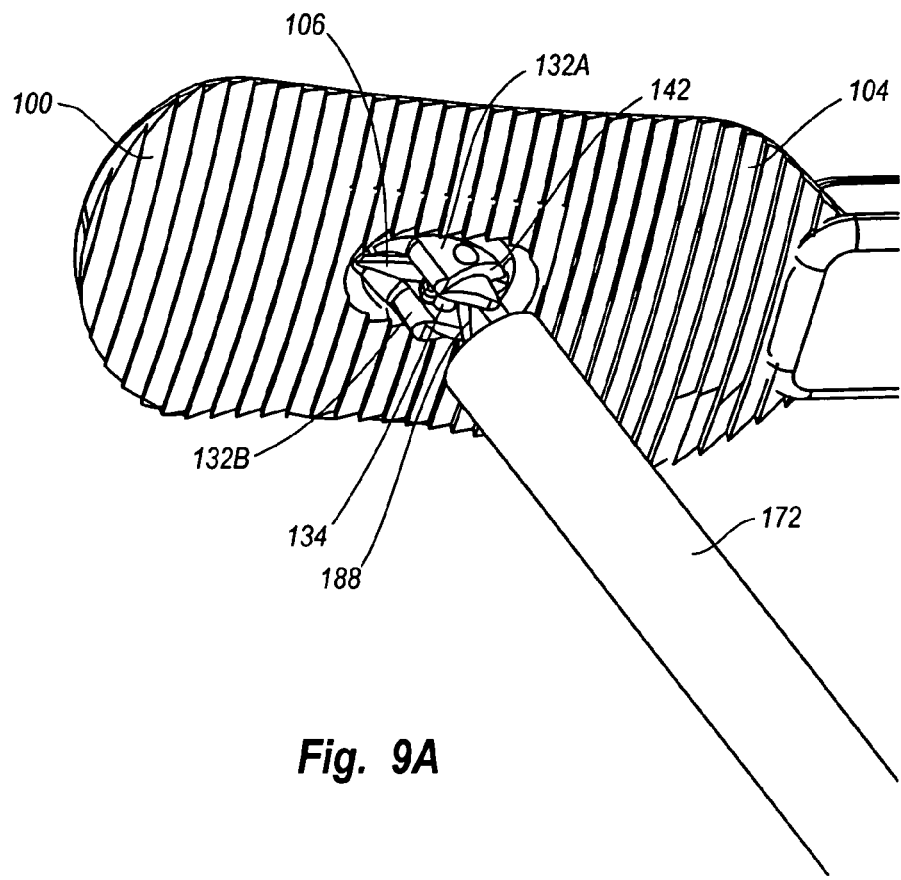
FIGS. 9A and 9B are perspective views of the retention rod shown in FIG. 8 being mounted to the rasp assembly shown in FIG. 5.

During operation, as depicted in FIG. 5, rasp assembly 100 is mounted on medial facet 24 of tibia 12. Rasp assembly 100 is positioned using the rigidly mounted insertion handle 160, as discussed above, such that forks 132A and B (FIG. 7) are aligned with the second end 96 of tunnel 90. Once rasp assembly 100 is positioned, retention rod 102 is advance within tunnel 90 from first end 94. As depicted in FIG. 9A, knob 192 is rotated so that hook 188 extends beyond set rod 172. With hook 188 freely exposed, hook 188 is hooked over pin 134 extending between forks 132A and B.

Figure 9B:
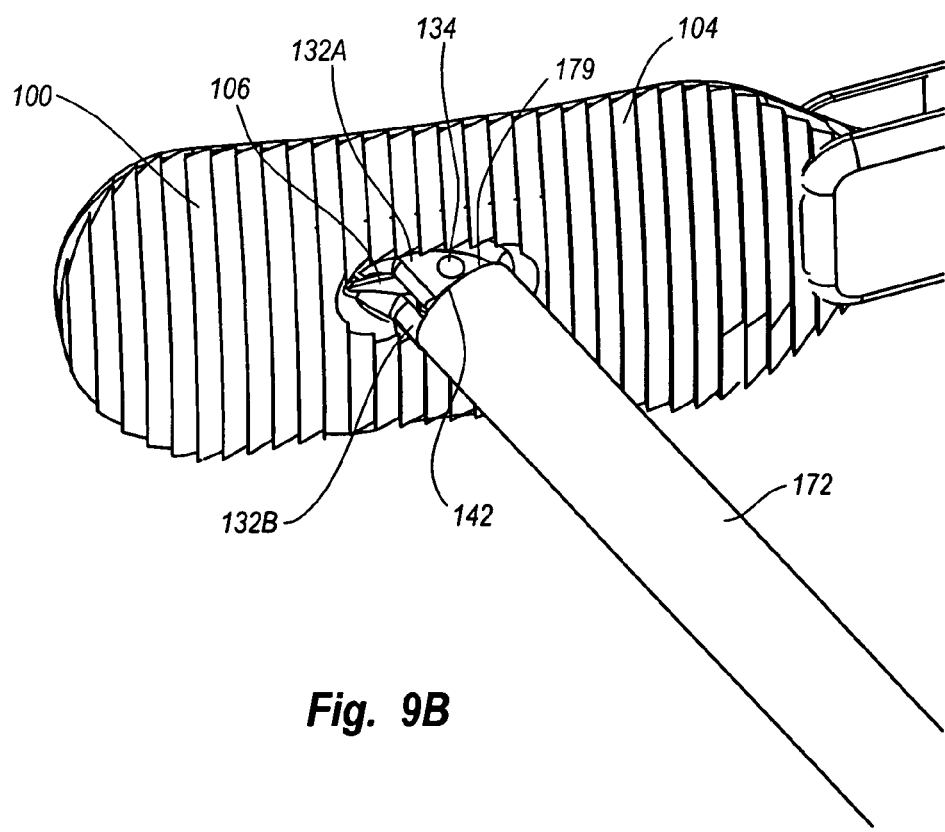

As depicted in FIG. 9B, once hook 188 has captured pin 134, knob 192 is rotated so as to advance set rod 172 toward hook 188. Set rod 172 is advanced until distal end face 179 of set rod 172 biases against shoulders 142 of forks 132A and B. Shoulders 142 are sloped such that end face 179 can sit flush against shoulder 142 while set rod 172 retains its orientation within tunnel 90. In this configuration, retention rod 102 is securely fixed to rasp guide 106.

Once retention rod 102 is secured to rasp assembly 100, insertion handle 160 is removed from pivot arm 105. A reciprocal driver, such as a reciprocal saw, not shown, is then connected pivot arm 105. While holding rasp guide 106 substantially stationary by holding onto retention rod 102, the reciprocal driver rapidly reciprocates rasp body 104 so that cutting edges 120 resect medial facet 24 of tibia 12. In one embodiment, rasp body 104 reciprocates along a length in a range between about 1 mm to about 4 mm. Other dimensions can also be used.

In one embodiment bottom surface 112 of rasp body 104 slightly arched so as to be convex. By having pivot arm 105 hingedly attached to rasp body 104, rasp body 104 is free to reciprocate along the arched path. The hinged attachment also helps to minimize binding of rasp body 104. In alternative embodiments, arm 105 can be rigidly attached to rasp body 104.

In one embodiment of the present invention means are provided for removably engaging retention rod 102 with rasp body 104 such that rasp body 104 can be selectively reciprocated without substantial movement of retention rod 102. By way of example and not by limitation, one embodiment of the means comprises rasp guide 106 slidably mounted on rasp body 104 and hook 188 mounted on retention rod 102. In alternative embodiments it is appreciated that a variety of different structures can accomplish the same function. For example, pin 134 and hook 188 can be replaced with a threaded connection, bayonet connection, or any number of other conventional connections which allows retention rod 102 to engage with rasp guide 106.

It is also appreciated that rasp guide 106 can be mounted on rasp body 104 in a variety of different ways. For example, opening 128 can extend through rasp body 104 without the formation of guide slot 122. In this embodiment slide plate 130 can be positioned directly on top surface 110 of rasp body 104 while forks 132A and B extend through opening 128. In yet another alternative, guide slot 122 can be formed on bottom surface 112 of rasp body 104. Cover plate 108 can be formed having opening 128 extending therethrough and cutting edges 120 formed on a bottom surface thereof. Slide plate 130 can be positioned within the guide slot 122 so that when cover plate 108 is secured over guide slot 122, forks 132A and B extend through opening 128 formed on cover plate 108.

It is also appreciated that retention rod 102 can have a variety of different configurations. For example, in alternative embodiments set rod 172 can be eliminated. As such, retention rod 102 can simply comprise hook rod 182. Furthermore, as discussed above, hook 188 can be replaced with a variety of different types of connectors.

Figure 10:
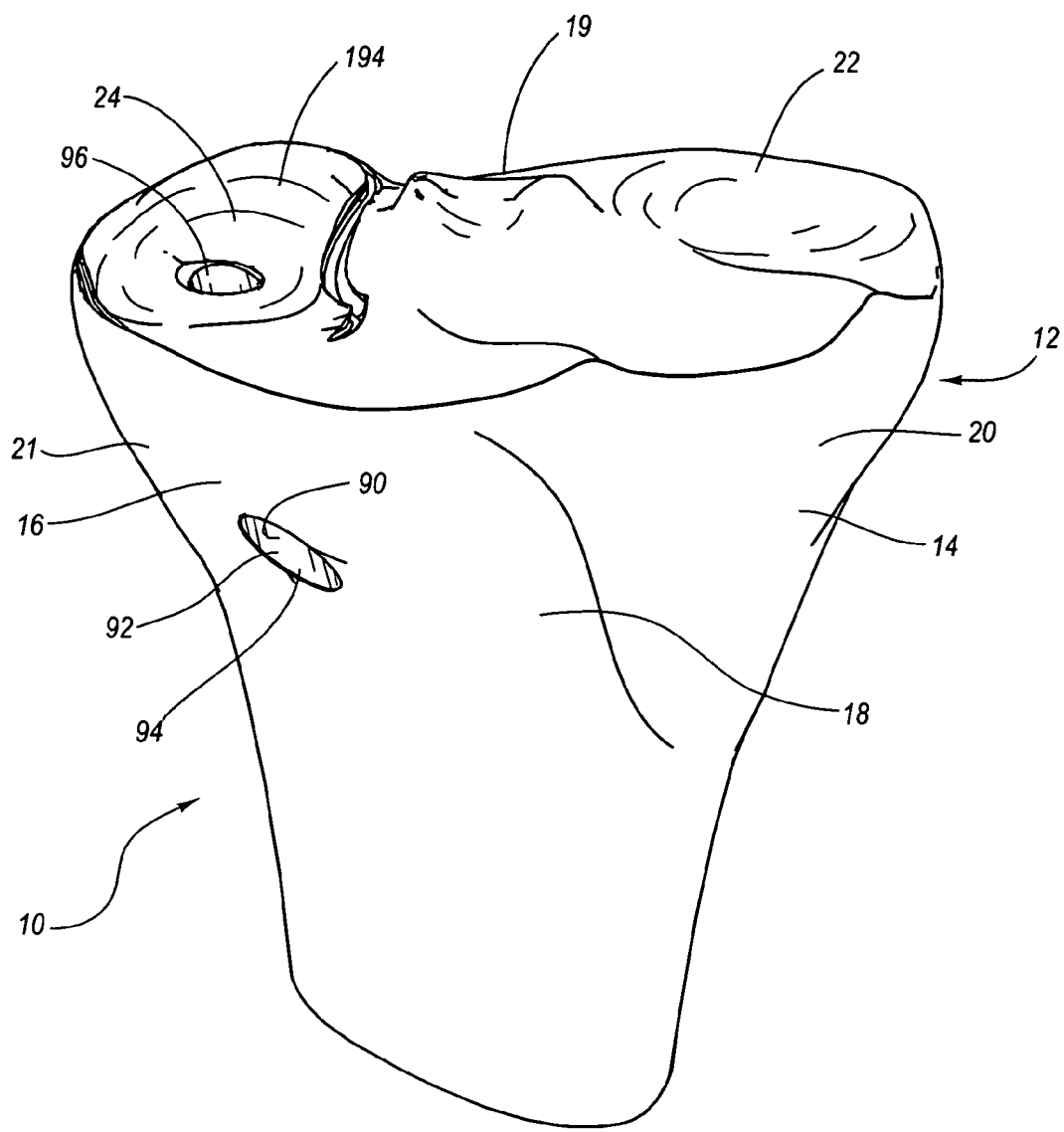
FIG. 10 is a perspective view of the tibia shown in FIG. 4 having a recess formed thereon.

Once medial facet 24 has been sufficiently resected by rasp body 104, rasp assembly 100 and retention rod 102 are removed. The resected bone particles are removed by conventional flushing and suction. As depicted in FIG. 10, tibia 12 now has a resected recess 194 formed on medial facet 24.

Figure 11:
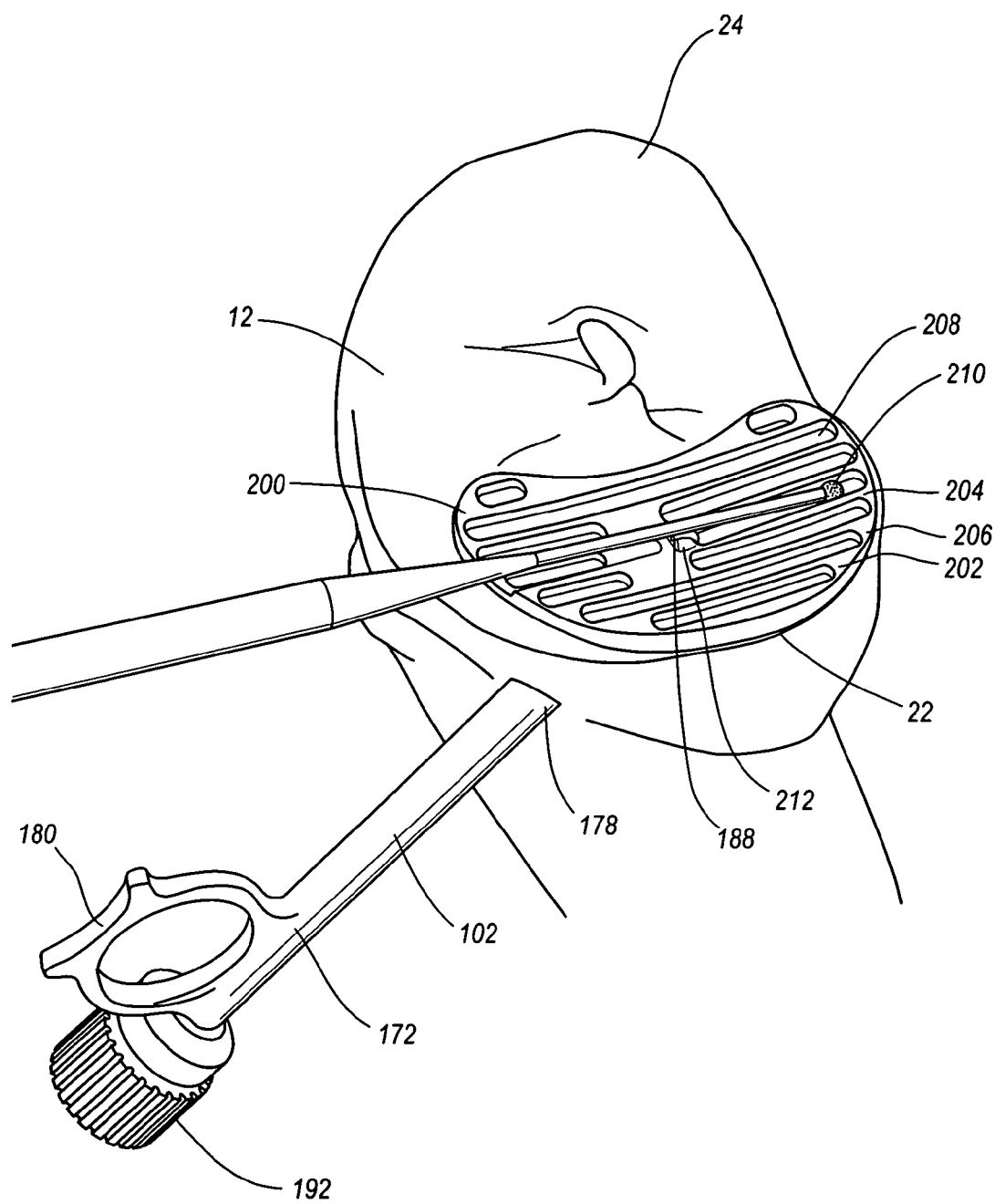
FIG. 11 is a perspective view of a cutting template being mounted on the tibia shown in FIG. 4.

It is appreciated that the resection of tibia 12 can be accomplished using a variety of different techniques. For example, in one alternative depicted in FIG. 11, the resection of tibia 12 is accomplished by cutting through an area bounded by a cutting template 200. Cutting template 200 comprises a plate 202 having a top surface 204 and an opposing bottom surface 206. In the embodiment depicted cutting template 200 is configured to rest on lateral facet 22 of tibia 12. Of course, cutting template 200 can also be designed for resting on medial facet 24.

Extending between opposing surfaces 204 and 206 are a plurality of guide spaces 208. Guide spaces 208 are formed so that when cutting template 200 is positioned, guide spaces 208 are positioned over at least a portion of the facet to be resected. In the embodiment depicted, guide spaces 208 have the configuration of an elongated channel. As will be discussed below in greater detail, the channels facilitate guided receipt of a cutting burr 210 which is used to selectively remove the unwanted bone. In alternative embodiments, depending on the type and size of tool used to remove the bone, guide spaces 208 can come in a variety of different sizes, shapes, and orientations.

In one embodiment, although not required or shown, a second cutting template is provided having guide spaces extending therethrough. In the second cutting template, the guide spaces are aligned so as to bound the area of the facet to be resected which was blocked by plate 202 of cutting template 200. As a result, by sequentially using both cutting templates, all or at least a greater proportion of the bone can be removed by cutting burr 210. Additional cutting templates can also be used.

Cutting template 200 is used in association with retention rod 102 as previously discussed. In the embodiment depicted, handle 180 has a different configuration. During use, cutting template 200 is position over lateral facet 22. Distal end 178 of set rod 172 is advanced through tunnel 90 so that hook 188 of hook rod 182 projects out of set rod 172. Hook 188 is passed though a guide space 208 and then pulled back onto top surface 204 of plate 202. A rib 212 upwardly projects from plate 202 adjacent to guide space 208. Hook 188 is hooked over rib 212 so as to improve the engagement between hook 188 and cutting template 200.

Once hook 188 is engaged to cutting template 200, knob 192 is rotated so as to bias set rod 172 against bottom surface 206 of template 200. As a result, retention rod 102 is securely clamped to cutting template 200. Accordingly, by pulling retention rod 102, cutting template 200 is securely held in place on lateral facet 22. Cutting burr 210 or some other form of drill bit is then advanced into and along each of guide spaces 208 so as to resect the portion of the bone directly below guide space 208. As previously discussed, in one embodiment cutting template 200 can be removed and replaced with a second template. Burr 100 can then be passed through guide spaces of the second template to remove further bone that was covered by cutting template 200.

In other alternatives, it is appreciated that once cutting template 200 is removed, the remaining bone portion can be removed by sight and feel without the use of a template. In yet other embodiments, depending on the type and amount of bone needed to be resected, a single template can be rotated or shifted on lateral facet 22 so that the single template is used to remove the desired bone.

In one embodiment of the present invention, means are provided for removably engaging retention rod 102 to cutting template 200 so that retention rod 102 secures cutting template 200 to the lateral or medial facet of tibia 12 when retention rod 102 is received within tunnel 90 of tibia 12. By way of example and not by limitation, one embodiment of such means comprises hook 188 and guide space 208 which enables hook 188 to engage with cutting template 200.

The present invention also envisions that there are a variety of other structures that can accomplish the same function. For example, the same structures and techniques as discussed above for securing retention rod 102 to rasp assembly 100 can also be used with cutting template 200. That is, in one alternative forks 132A and B with pin 134 can be mounted on bottom surface 206 of plate 202. Other connections such as threaded connection, bayonet connections, and the like can also be used.

By using the above discussed instruments and methods, the lateral and medial facets of tibia 12 can be selectively resected by procedures that are minimally invasive.

Figure 12A:
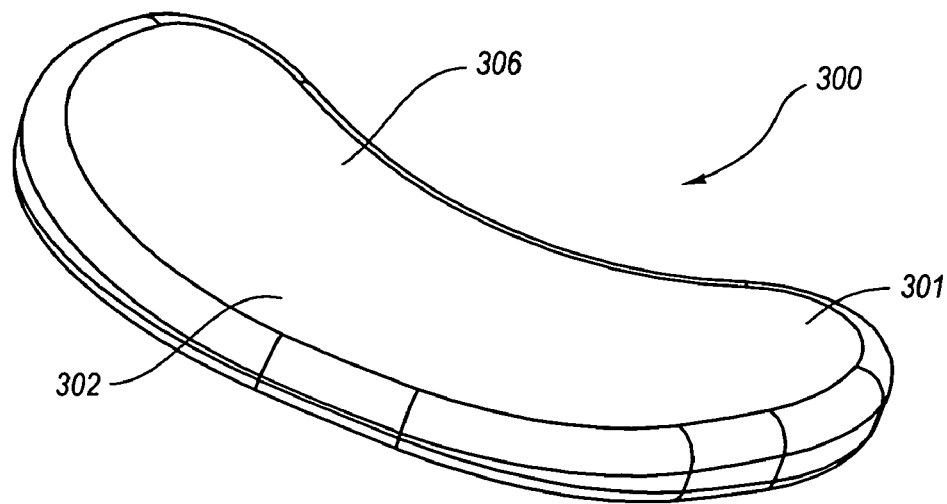
FIG. 12A is a top perspective view of a condylar implant.
Figure 12B:
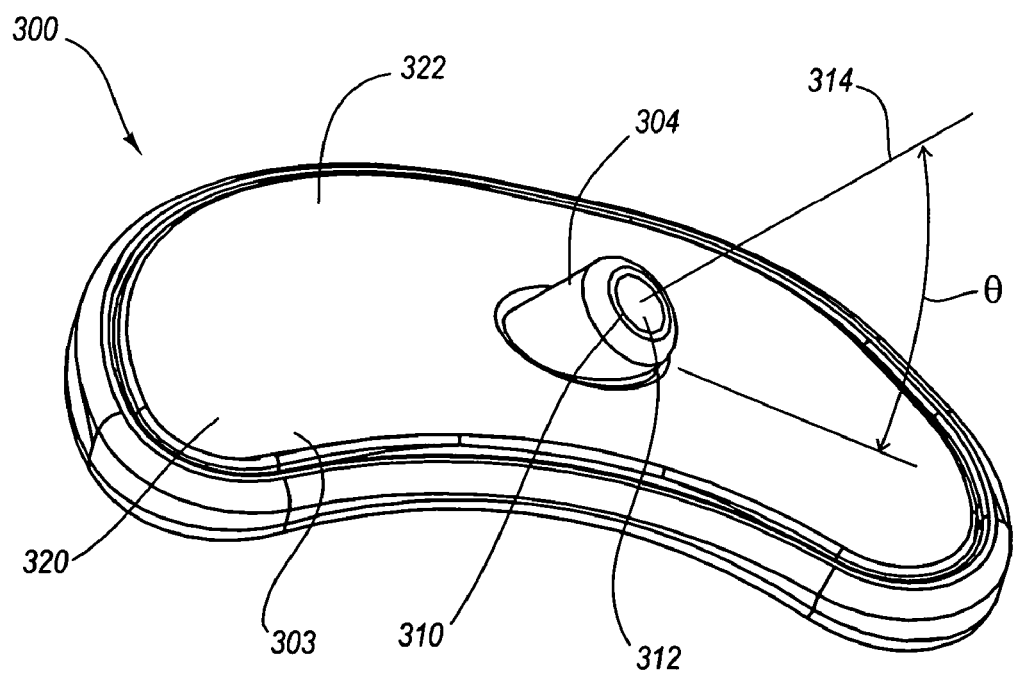
FIG. 12B is a bottom perspective view of the condylar implant shown in FIG. 12A.
Figure 12C:
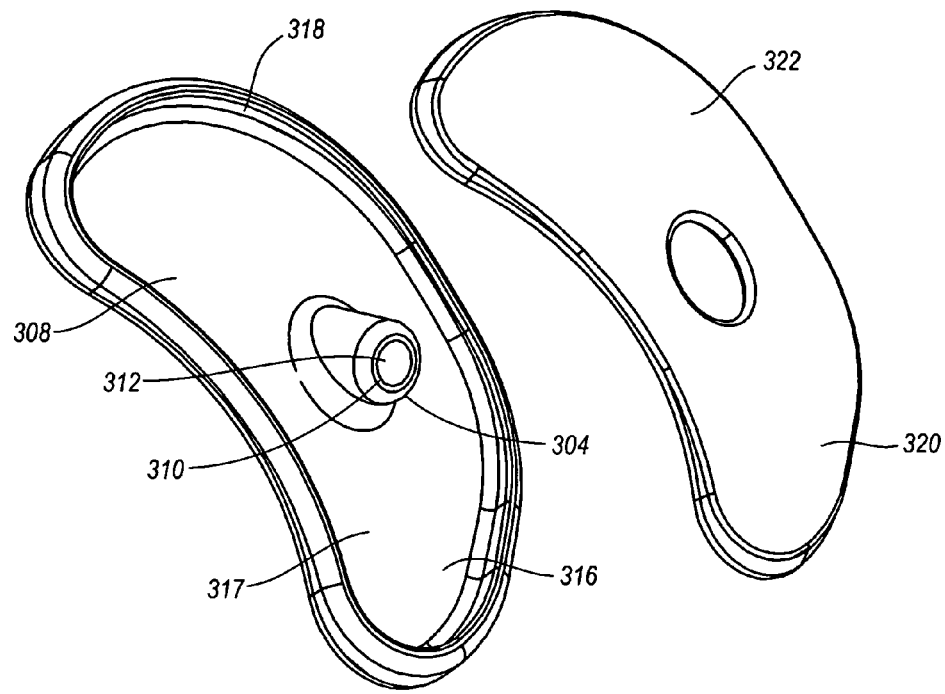
FIG. 12C is an exploded perspective view of the condylar implant shown in FIG. 12B.

Depicted in FIGS. 12A-12C is one embodiment of a condylar implant 300 incorporating features of the present invention. The term "condylar implant" is broadly intended to include implants that can replace all or a portion of a condyle of a tibia. The condylar implant can also replace all or a portion of the articular surface of the condyle. Accordingly, while the depicted embodiments show one conventional size and configuration for a condylar implant, in alternative embodiments the condylar implant can be larger to replace more of the tibia or can be smaller to replace only a section of a condyle of a tibia. In such alternatives, the condylar implant can have a variety of different configurations.

In general, condylar implant 300 comprises a body 301 having a top articular surface 306 and an opposing bone apposition surface 303. In one embodiment, top articular surface 306 is contoured to mate with a corresponding femoral condyle. A stem 304 projects from bone apposition surface 303. Body 301 comprises a bearing plate 302 having top articular surface 306 and an opposing bottom surface 308. A pocket 316 is recess on bottom surface 308. Pocket 316 is bounded by a floor 317 and a sidewall 318 upstanding around the perimeter thereof. As discussed below in greater detail, an inlay 320 is disposed within pocket 316.

Stem 304 projects from bottom surface 308 of bearing plate 302 and terminates at a distal terminus 310. Recessed within distal terminus is a threaded socket 312. Bearing plate 302 and stem 304 are typically comprised of a metal such as chromium, cobalt, titanium, or the like and alloys thereof but can also be made of ceramics or plastics. Bearing plate 302 and/or stem 304 can also be comprised of layers or sections of different materials. In one embodiment, bearing plate 302 has a maximum thickness typically in a range between about 2 mm to about 10 mm. Other dimensions can also be used depending on the amount that the tibial condyle is resected or worn away.

In one embodiment of the present invention, means are provided for connecting a fastener to stem 304. One example of such means comprises threaded socket 312 as discussed above. In alternative embodiments, the threads within the socket on stem 304 could be replaced with bayonet slots, bayonet posts, ribs which are configured to mate with barbs or other forms of connectors. The socket can also be filled with an adhesive. In still other embodiments, the socket can be eliminated and threads, bayonet posts, barbs or other forms of connections can be formed on the exterior of stem 304.

Secured within pocket 316 so as to encircle stem 304 is inlay 320. Inlay 320 is comprised of a porous bone ingrowth material such as porous tantalum. Other conventional porous bone ingrowth materials can also be used. Inlay 320 is secured within pocket 316 using conventional techniques such as press fit, welding, adhesive, and the like. Inlay 320 has an exposed bottom surface 322 that can be substantially flat, arched, or can have any other desired configuration. In this embodiment, bottom surface 322 of inlay 320 comprises substantially all of bone apposition surface 303 of base plate 301.

Centrally extending through stem 304 is a central longitudinal axis 314. In one embodiment, stem 304 projects from floor 317 so as to form an angle θ between central longitudinal axis 314 and inlay 320 in a range between about 30° to about 60°. Other angles can also be used. Stem 304 typically has a length in a range between about 2 mm to about 10 mm. Other dimensions can also be used.

It is appreciated that condylar implant 300 can have a variety of alternative configurations. For example, stem 304 is primarily formed to provide sufficient room for socket 312 when bearing plate 302 has a relative small thickness. As the thickness of bearing plate 302 increases, stem 304 can be increasingly shortened as more of socket 312 can be formed directly into bearing plate 302. As such, in some embodiments stem 304 can be eliminated in that all of socket 312 can be formed directly on bearing plate 302.

Furthermore, in the depicted condylar implant 300, pocket 316 is formed to receive inlay 320. In alternative embodiments pocket 316 can be eliminated and a section of the porous bone ingrowth material can be mounted on the bottom surface of bearing plate 302 using other conventional fastening techniques such as adhesives, screws, alternative press fits, and the like. Furthermore, in contrast to one pocket 316, a plurality of spaced apart pockets can be formed on bottom surface 308 with each pocket receiving a separate inlay 320. Here it is noted that spikes, fins, or other forms of projections can also be formed projecting from bottom surface 308 of bearing plate 302. These projections can penetrate into the tibia or be received within slots formed on the tibia to help prevent movement of bearing plate 302.

Figure 13:
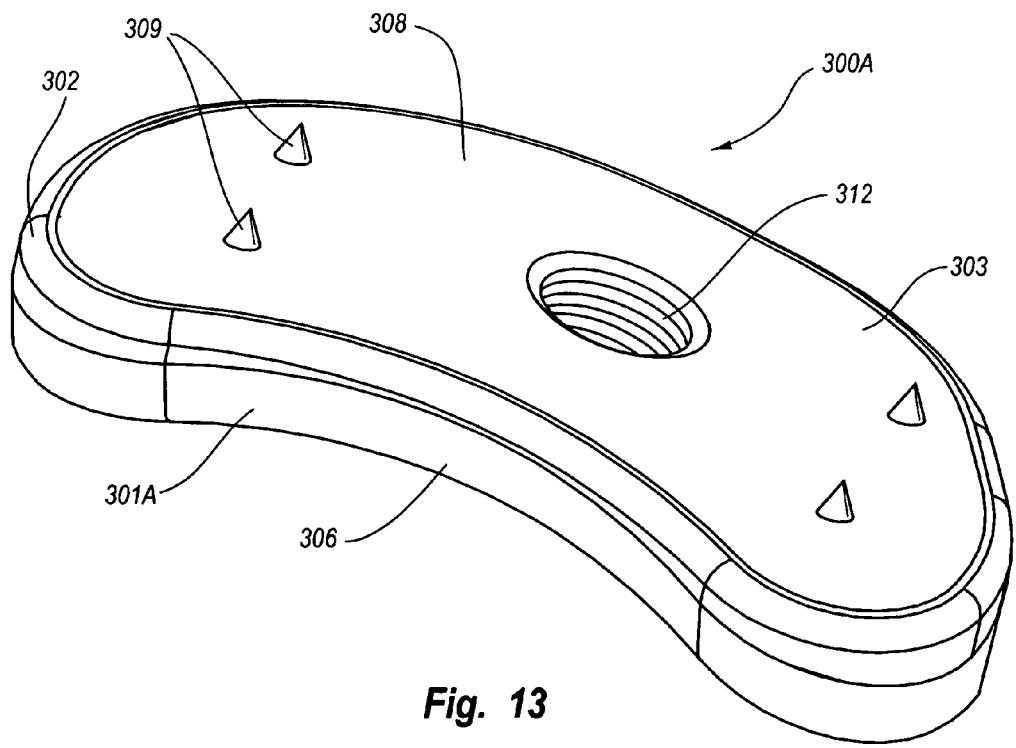
FIG. 13 is a perspective view of an alternative embodiment of a condylar implant.

In still other embodiments, it is appreciated that inlay 320 or other forms of the porous bone ingrowth material can be eliminated. In this embodiment, the condylar implant can comprise a single integral member. For example, depicted in FIG. 13 is an alternative embodiment of a condylar implant 300A. Implant 300A is formed as a single integral body 301A having top articular surface 306 and bone apposition surface 303. Implant 300A can also be characterized as comprising a bearing plate that is free to pockets or inlays. The bottom surface of the bearing plate comprises bone apposition surface 303. Because of the increased thickness of implant 300A, stem 304 is eliminated. Threaded socket 312 is formed directly on bone appositions surface 303. Projections 309 extend from surface 303.

Figure 14:
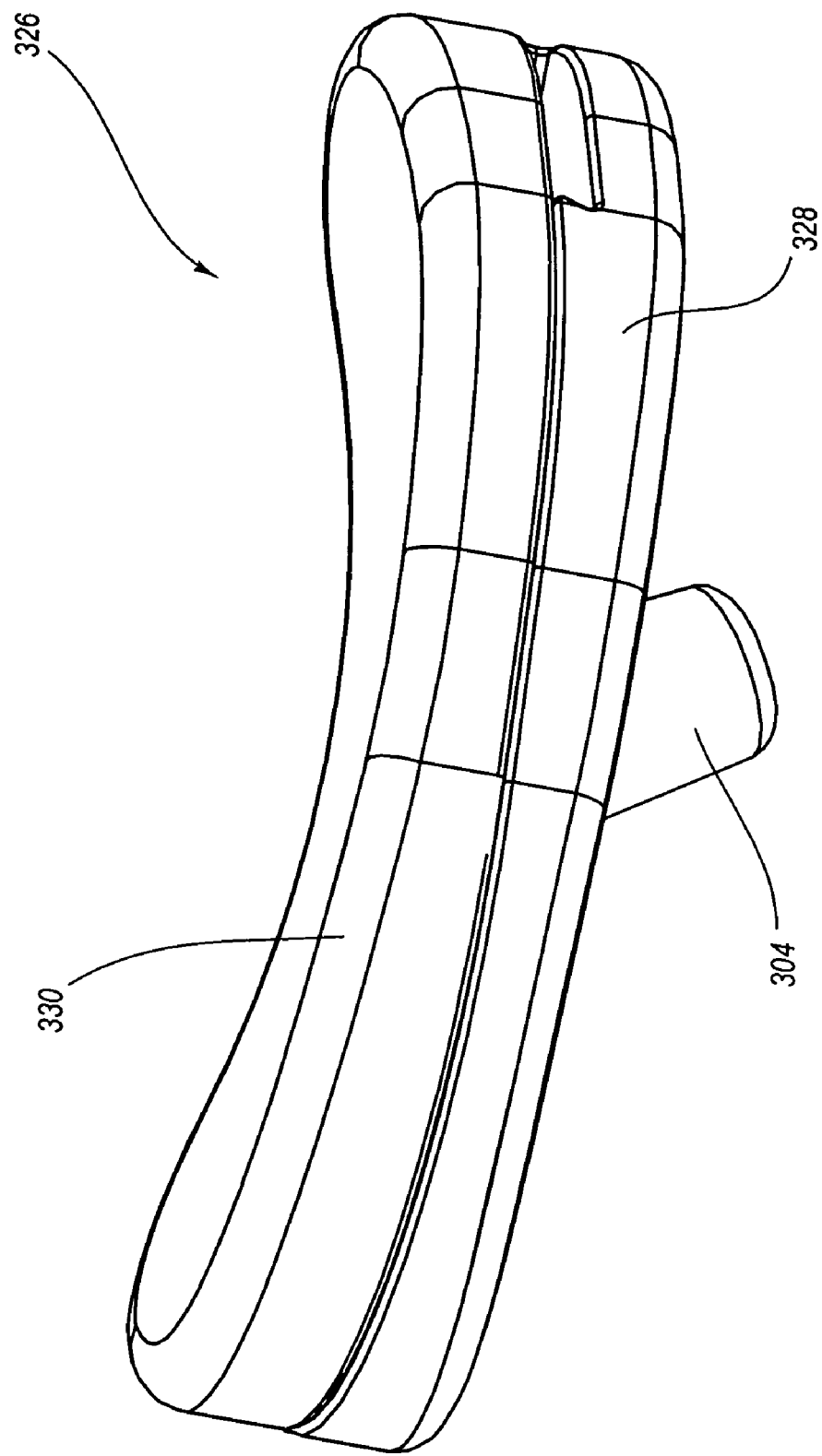
FIG. 14 is a perspective view of another alternative embodiment of a condylar implant.

In yet another alternative embodiment, depicted in FIG. 14 is a condylar implant 326. Like elements between condylar implants 300 and 326 are identified by like reference characters. In contrast to condylar implant 300 which is fixed and rigid, condylar implant 326 is mobile. Specifically, condylar implant 326 comprises a lower bearing plate 328 from which stem 304 projects and an upper bearing plate 330 that is slidably mounted on lower bearing plate 328.

Figure 15A:
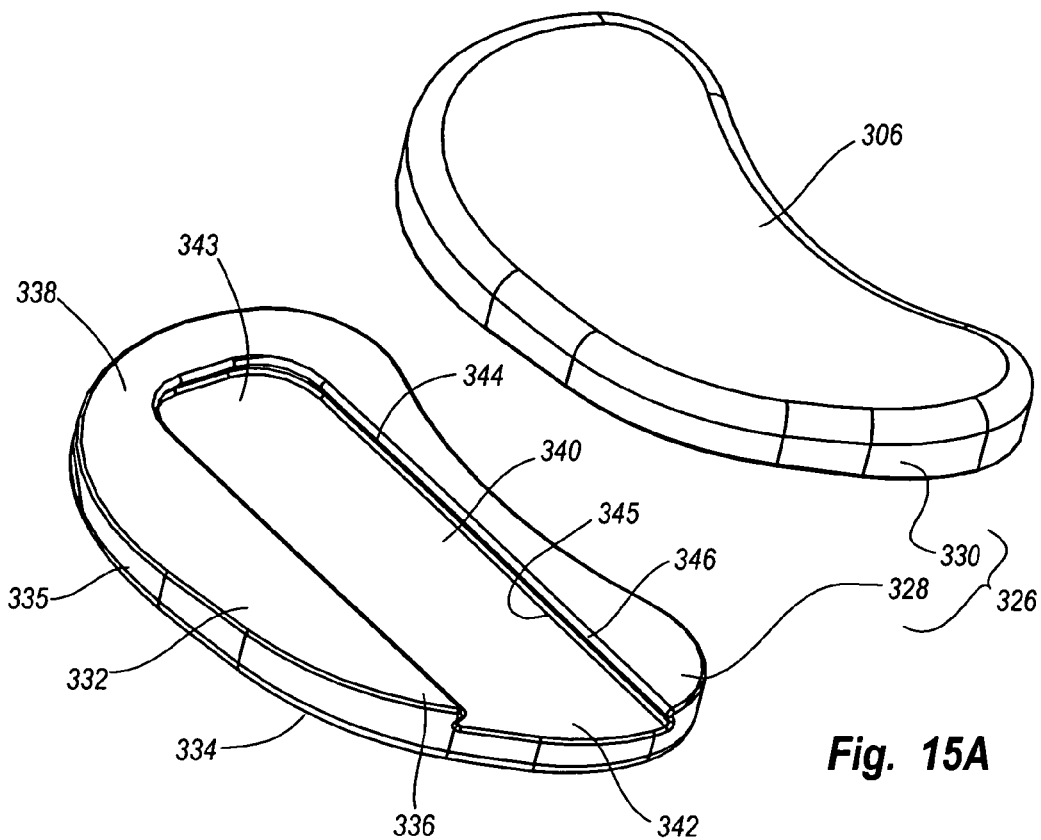
FIG. 15A is a top exploded perspective view of the condylar implant shown in FIG. 14.
Figure 15B:
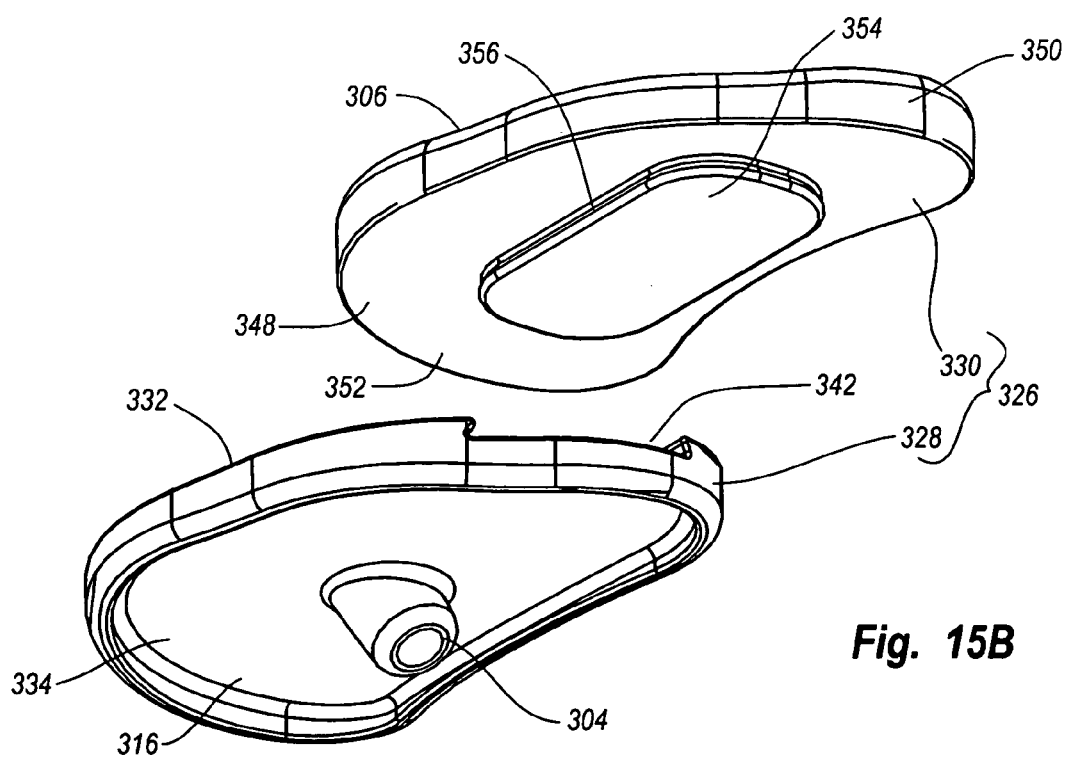
FIG. 15B is bottom exploded perspective view of the condylar implant shown in FIG. 15A.

As depicted in FIGS. 15A and B, lower bearing plate 328 has a top surface 332 and an opposing bottom surface 334 with a perimeter edge 335 extending therebetween. Pocket 316 is formed on bottom surface 334 to receive inlay 320. Top surface 332 is substantially flat or inwardly arched and extends between an anterior end 336 and a posterior end 338. A track 340 is recessed on top surface 332. Track 340 has an open mouth extending through perimeter edge 335 at anterior end 336 and longitudinally extends toward posterior end 338. Track 340 is bounded by a substantially flat floor 343 having a sidewall 344 upstanding therefrom. Sidewall 344 comprises a recess groove 345 which extends along floor 343 and an outwardly projecting lip 346 which projects along top surface 332. As such, the opposing sidewalls 344 of track 340 form a mortis.

Upper bearing plate 330 comprises top articular surface 306 and a bottom surface 348 which each extend between an anterior end 350 and an opposing posterior end 352. Bottom surface 348 has a configuration substantially congruent to top surface 332 of lower bearing plate 328. Projecting from bottom surface 348 is an elongated key 354 which extends from toward anterior end 350 to toward posterior end 352. Key 354 has a sidewall 356 that is substantially complementary to sidewall 344 of tack 340 such that key 354 forms a tenon that can slide into track 340 from mouth 342. In this position key 354 can freely slide along track 340 but is prevented from vertically separating from track 340.

During use, upper bearing plate 330 can slide posterior-anterior on lower bearing plate 328 as the femoral condyle rotates on top articular surface 306. This ability of upper bearing plate 330 to slide minimizes high stress points between the femoral condyle and upper bearing plate, thereby minimizing wear. Furthermore, because bearing plates 328 and 330 slide against each other on congruent surfaces, both of bearing plates 328 and 330 can be comprised of metal without producing undue wear. In other embodiments, bearing plates 328 and 330 can be comprised of plastics, ceramics, or composites of different materials. In addition, bearing plates 328 and 330 can be made of the same or different materials.

Figure 16A:
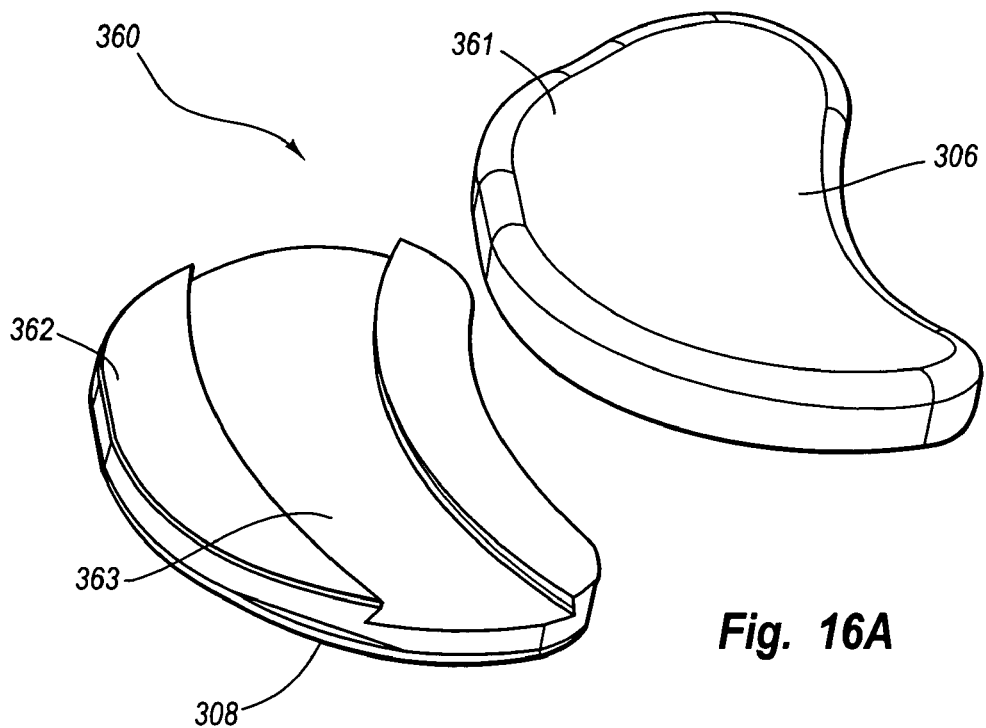
FIG. 16A is a top exploded perspective view of an alternative condylar implant.
Figure 16B:
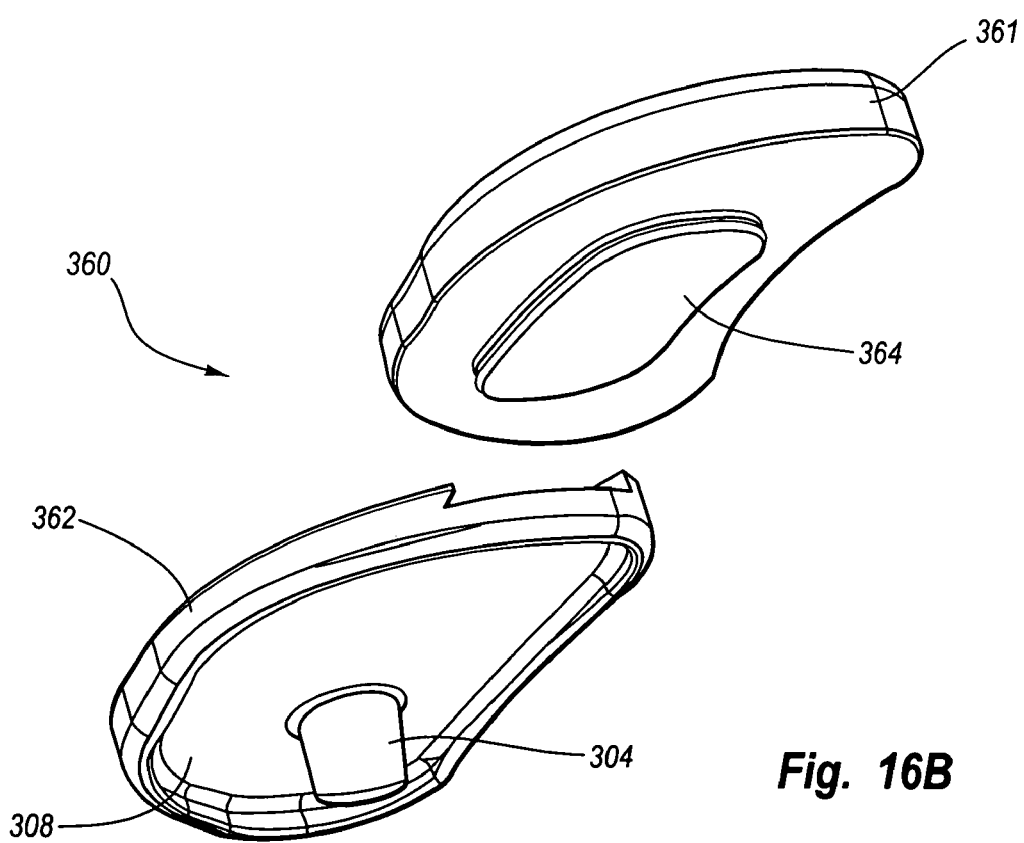
FIG. 16B is bottom exploded perspective view of the condylar implant shown in FIG. 16A.

Although key 354 and track 340 are shown as being linear, in alternative embodiments they can be congruently curved to more naturally correspond to the bending movement of the knee. For example, depicted in FIGS. 16A and B is another alternative embodiment of a condylar implant 360 which includes an upper bearing plate 361 and a lower bearing plate 362. In this embodiment, lower bearing plate 362 includes a track 363 that is curved along the length thereof. Upper bearing plate 361 includes an elongated key 364 having a curve complementary to track 363 such that key 364 can freely slide within track 363. As previously discussed, key 364 and track 363 can also be arched or curved in a vertical plane.

Figure 17:
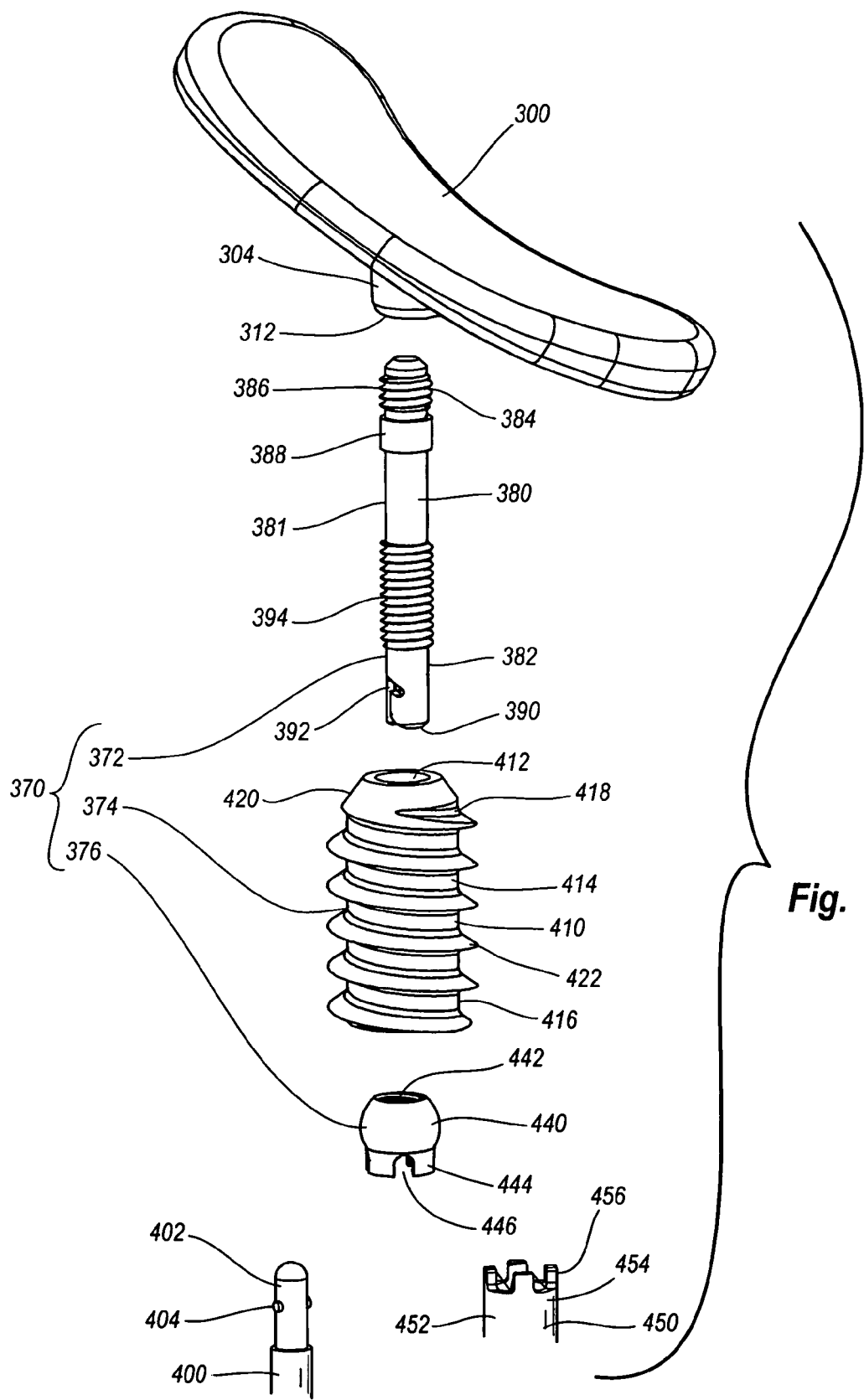
FIG. 17 is an exploded view of an anchor assembly for securing a condylar implant to the tibia shown in FIG. 10.

Depicted in FIG. 17 is one embodiment of an anchor assembly 370 used to secure condylar implant 300 to tibia 12. Anchor assembly 370 comprises a fastener 372, a bone anchor 374, and a crown nut 376. Fastener 372 comprises an elongated shaft 380 having an exterior surface 381 extending between a proximal end 382 and an opposing distal end 384. In one embodiment, fastener 372 has a length greater than 8 mm and more commonly greater 15 mm. Other dimensions can also be used.

Formed at distal end 384 of shaft 380 are threads 386 that are configured to threadedly mate with threaded socket 312 of stem 304. Outwardly projecting proximal of threads 386 is an annular flange 388 which functions as a stop when fastener 372 is threaded into stem 304. Recessed into proximal end 382 is a socket 390. A pair of opposing bayonet slots 392 longitudinally extend through the sidewall bounding socket 390. Finally, encircling and radially outwardly projecting from exterior surface 381 between proximal end 382 and flange 388 are engagement threads 394.

Figure 18:
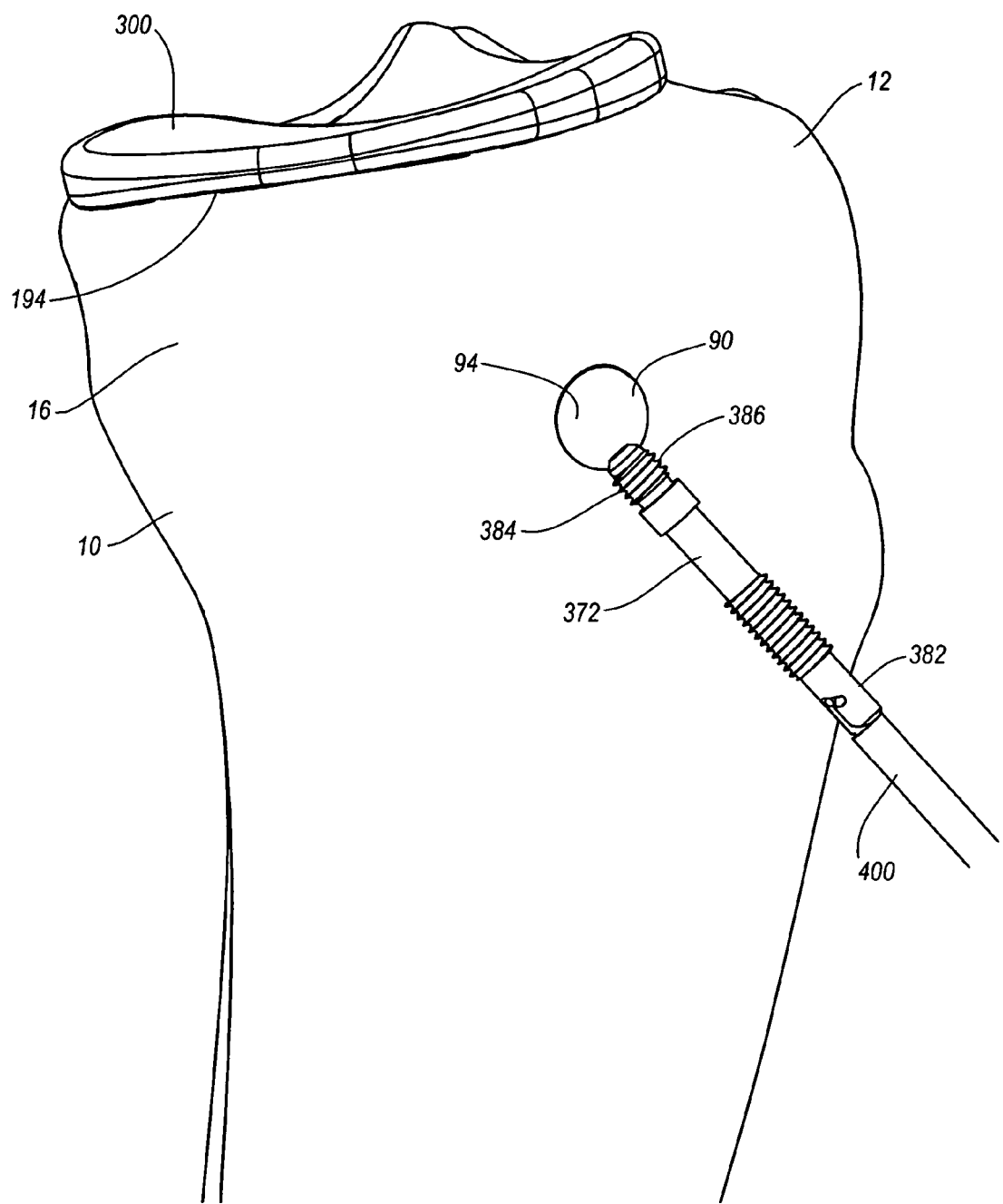
FIG. 18 is a side view of the fastener of the anchor assembly shown in FIG. 17 being secured to the condylar implant positioned on the tibia.

As depicted in FIG. 18, condylar implant 300 is mounted within recess 194 such that stem 304 is received within second end 96 of tunnel 90. Here it is noted that because condylar implant 300 has a relatively low profile, condylar implant 300 can be easily passed through the relatively small incision that was originally formed over the medial meniscus. This is in contrast to other conventional procedures where larger incisions must be made to either allow placement of an implant having a large stem that is embedded within the bone for securing or to provide access room to enable securing of the implant by passing screws down through the top of at least a portion of the implant.

Once implant 300 is positioned, a fastener driver 400 has a distal head 402 (FIG. 17) that is configured to be received within socket 390 of fastener 372. A pair of opposing bayonet prongs 404 project from head 402 and are configured to mate within bayonet slots 392. With fastener driver 400 secured to proximal end 382 of fastener 372, fastener driver 400 is used to advance distal end 384 into tunnel 90 through first end 94. Fastener 372 is advanced through tunnel 90 so that threads 386 are received within socket 312 of stem 304. Fastener driver 400 is then rotated so that fastener 372 is threaded into stem 304.

Next, bone anchor 374 is secured within tunnel 90. In one embodiment, a tap, not shown, is used to initially thread interior surface 92 of tunnel 90. This can be accomplished before or after positioning of fastener 372. Alternatively, bone anchor 374 can be self-tapping.

As depicted in FIG. 17, bone anchor 374 comprises a tubular body 410 having a substantially cylindrical configuration. Body 410 includes an interior surface 412 and an exterior surface 414 that each extend between a proximal end 416 and an opposing distal end 418. Distal end 418 includes a tapered nose 420. Encircling and radially outwardly projecting from exterior surface 414 are one or more helical threads 422. As mentioned above, the threads can be conventional or self-taping. In alternative embodiments, threads 422 can be replaced by ridges, barbs, or other bone engaging structures used in conventional bone anchors. Bone anchor 374 can be formed of a biocompatible metal, a bioabsorbable polymer, a bioactive ceramic, or any other desired material.

Figure 19:
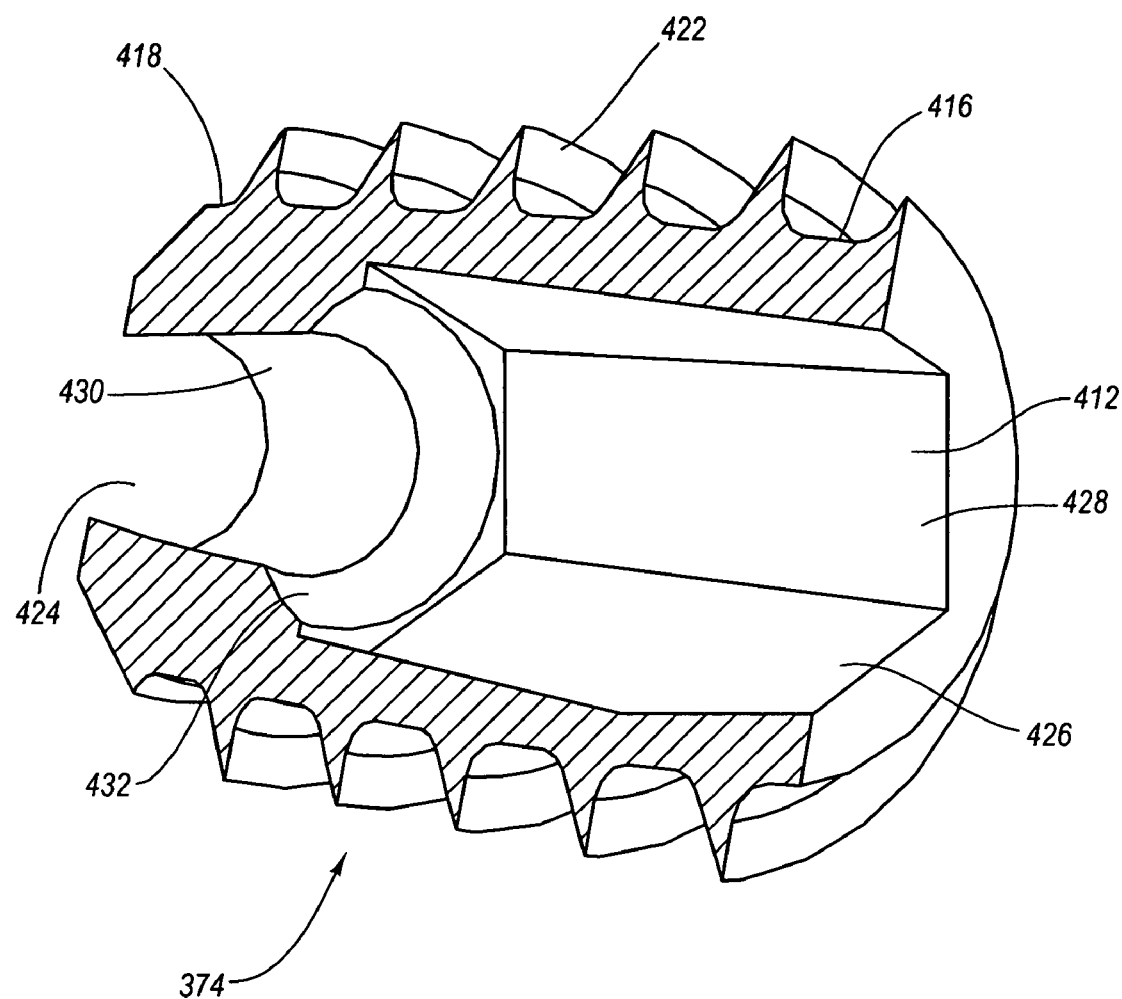
FIG. 19 is a cross sectional perspective view of the bone anchor of the anchor assembly shown in FIG. 17.

As depicted in FIG. 19, interior surface 412 bounds a channel 424 longitudinally extending through bone anchor 374. Interior surface 412 comprises a first sidewall 426 extending from proximal end 416, a second sidewall 430 extending from distal end 418, and an annular shoulder 432 extending between first sidewall 426 and second sidewall 430. First sidewall 426 has a maximum diameter that is greater than the maximum diameter of second sidewall 430. As such, shoulder 432 is tapered so as to constrict from first sidewall 426 to second sidewall 430. First sidewall 426 bounds a socket 430 which is configured to receive a tool for rotation of bone anchor 374. As such, first sidewall 426 has a non-circular transverse cross section. In typical embodiments, first sidewall 426 has a polygonal transverse cross section.

Figure 20:
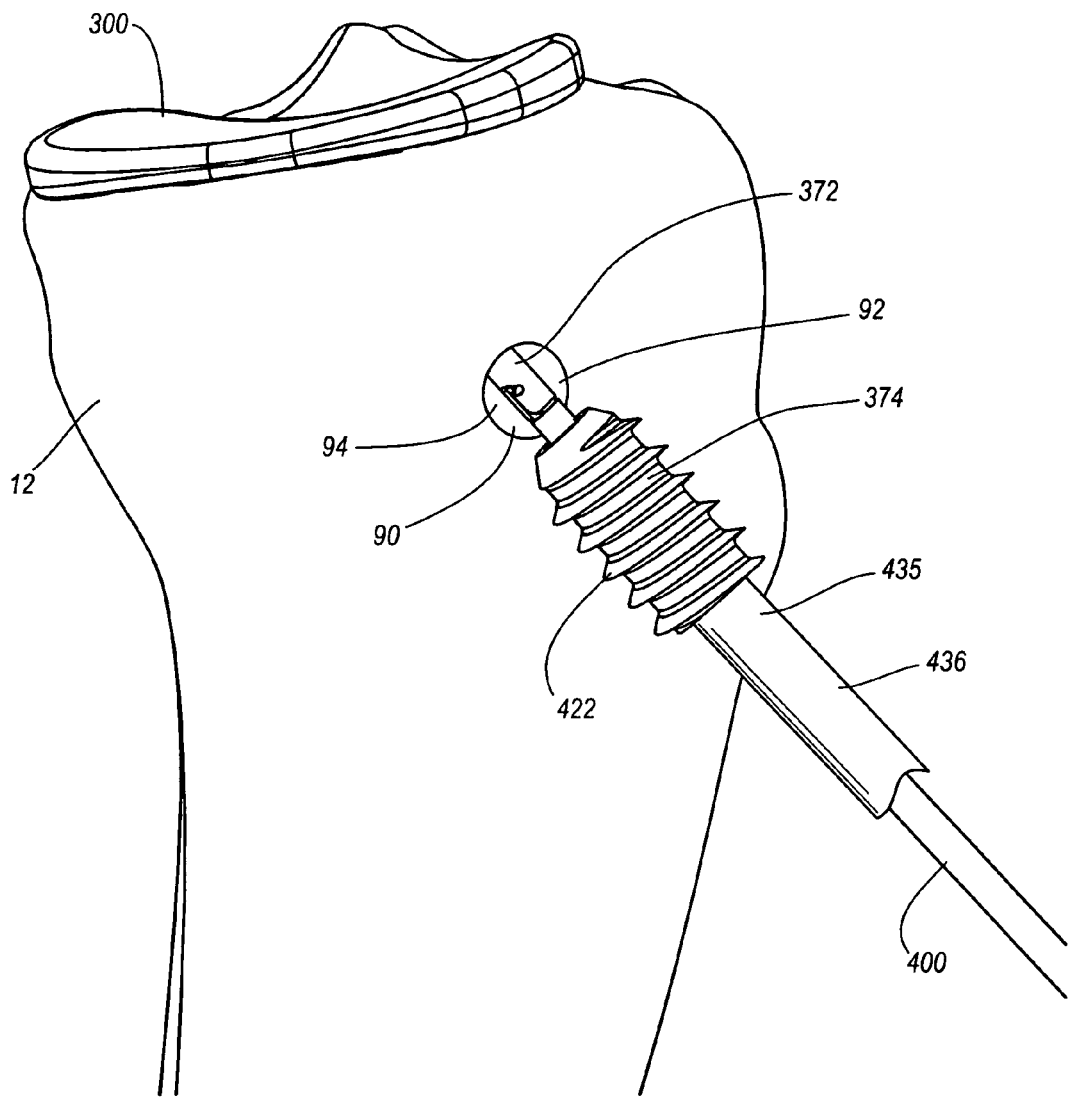
FIG. 20 is a side view of the bone anchor shown in FIG. 19 being mounted to the tibia shown in FIG. 18.

Turning to FIG. 20, a distal end 435 of a tubular anchor driver 436 is received within engagement socket 438 of bone anchor 374. Distal end 435 has a polygonal configuration complementary to socket 438 such that rotation of anchor driver 436 rotates bone anchor 364. Bone anchor 374 and anchor driver 436 are passed over the proximal end of fastener driver 400 and advanced to first end 94 of tunnel 90. By rotating anchor driver 436, bone anchor 374 is screwed into tunnel 90 using fastener driver 400 as a guide. Bone anchor 374 is sized so that threads 422 engage with interior surface 92 of tunnel 90, thereby securing bone anchor 374 to tibia 12 within tunnel 90. Bone anchor 374 is advanced so that bone anchor 374 encircles engagement threads 394 of fastener 372. Using fastener driver 400 as a guide for bone anchor 374 helps to concentrically dispose bone anchor 374 around fastener 372.

Once bone anchor 374 is positioned, anchor driver 436 is removed and crown nut 376 is positioned. As depicted in FIG. 17, crown nut 376 comprises a rounded head 440 having a threaded bore 442 extending therethrough. Projecting from head 440 are a plurality of spaced apart prongs 444 having notches 446 formed therebetween. Crown nut 376 is configured to mate with a nut driver 450. Nut driver 450 comprises a tubular shaft 452 that terminates at a distal end 454. Projecting from distal end 454 are a plurality of spaced apart prongs 456. Prongs 456 are configured to mate with crown nut 376 by being received within notches 446. In this mated configuration, rotation of nut driver 450 facilitates rotation of crown nut 376.

Figure 21:
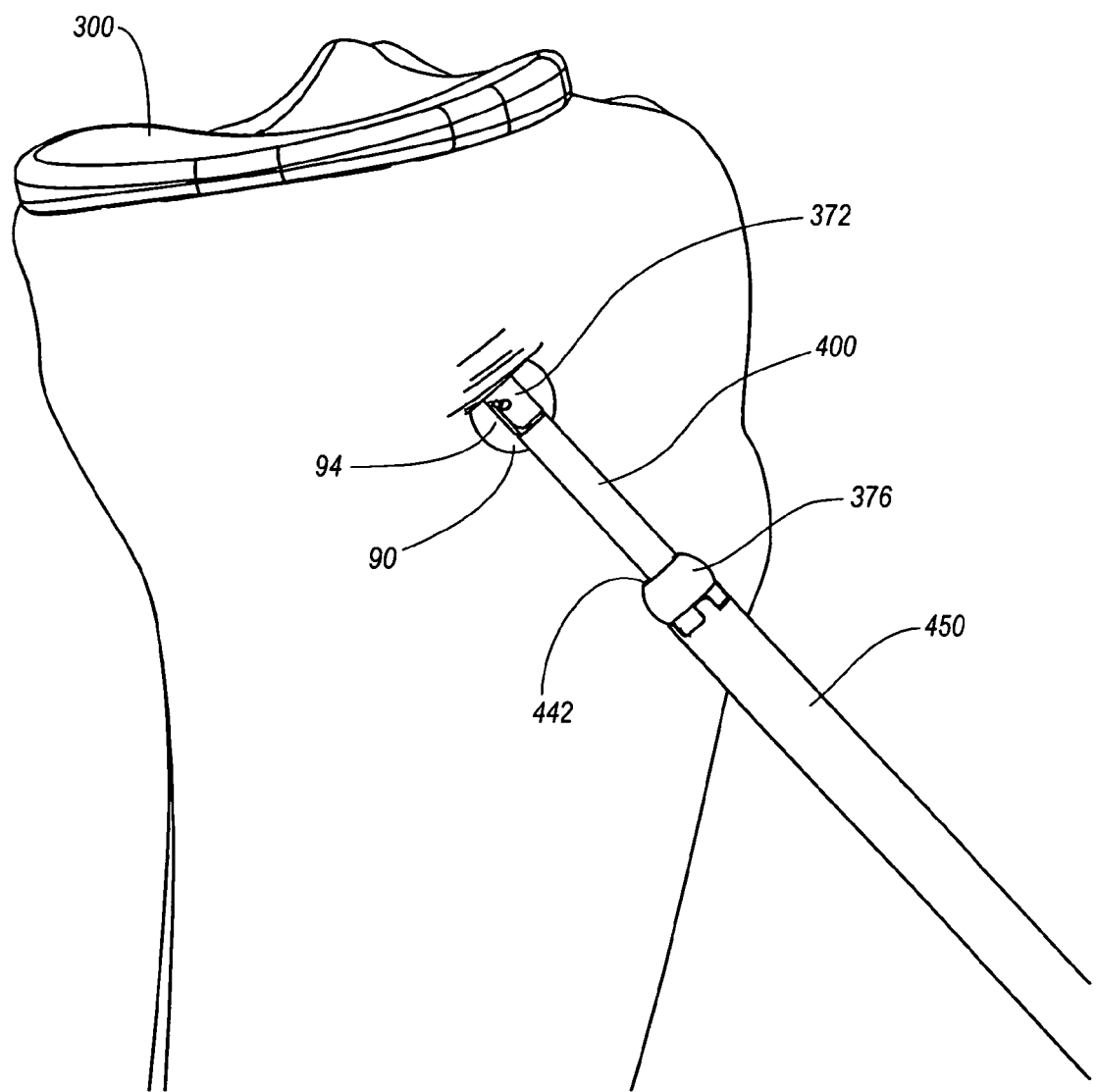
FIG. 21 is a side view of a crown nut of the anchor assembly shown in FIG. 17 being mounted to the fastener shown in FIG. 18.

Turning to FIG. 21, with crown nut 376 mounted on nut driver 450, crown nut 376 and nut driver 450 are passed over the proximal end of fastener driver 400. Nut driver 450 is used to advance crown nut along fastener driver 400, into tunnel 90, and over fastener 372. Threaded bore 442 of crown nut 376 is configured to threadedly mate with engagement threads 394 on fastener 372. Accordingly, once crown nut 376 is advanced over fastener 372 to engagement threads 394, nut driver 450 is rotated causing crown nut 376 to threadedly engage with engagement threads 394.

Figure 22:
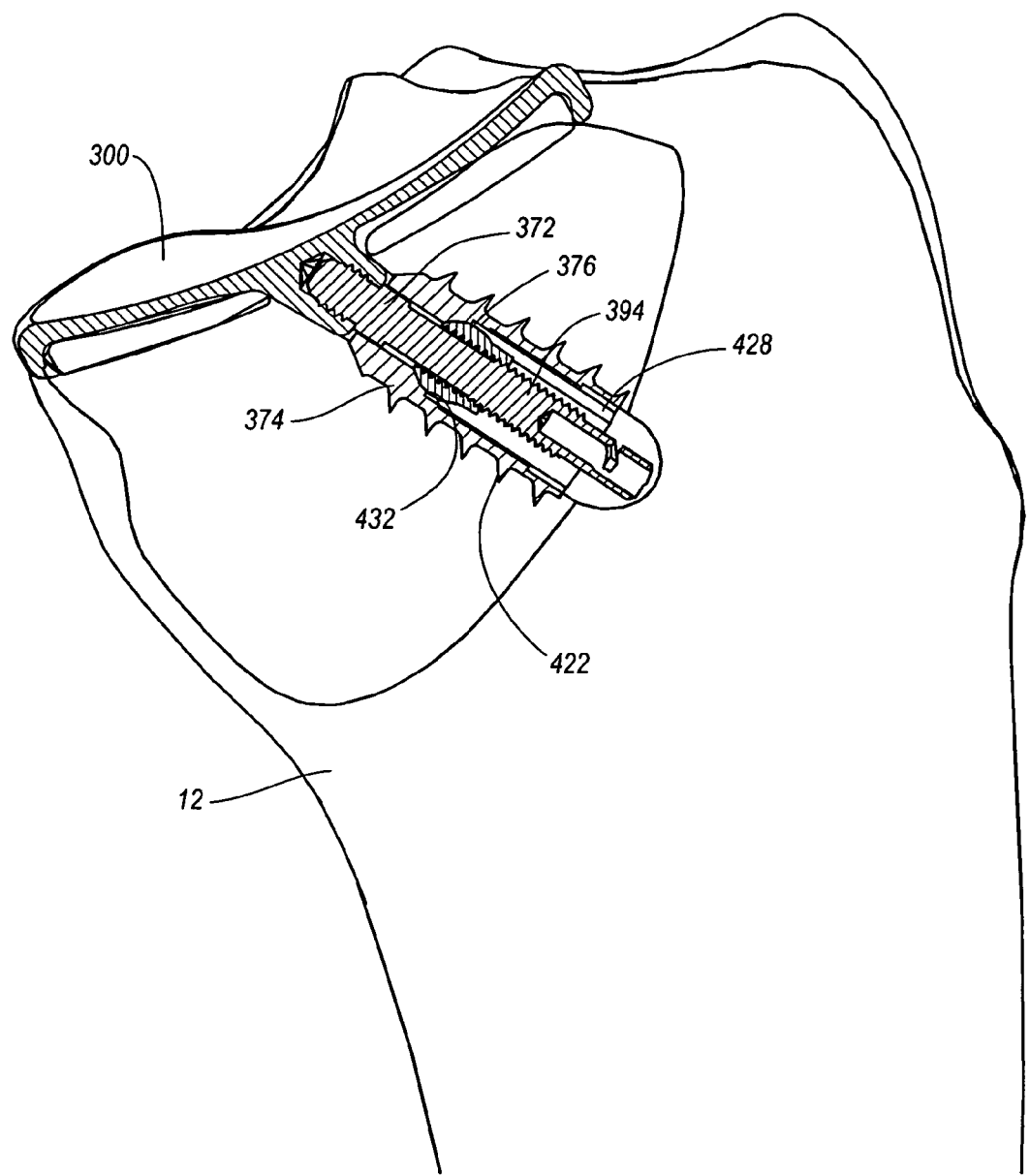
FIG. 22 is a cross sectional side view of the assembled anchor assembly shown in FIG. 17 securing the condylar implant to the tibia.

As depicted in FIG. 22, socket 428 of bone anchor 374 is larger than head of crown nut 376 such that crown nut 376 can freely pass therethrough. Shoulder 432, however, constricts to a diameter smaller than the diameter of head 440 of crown nut 376. Accordingly, crown nut 376 is advanced along fastener 372 by engaging with threads 394 until head 440 of crown nut 376 biases against shoulder 432 of bone anchor 374. Tightening crown nut 376 against shoulder 432 produces tension on fastener 376 which tightly secures condylar implant 300 against tibia 12.

In one embodiment, engagement threads 394 on fastener 372 rotate in a direction opposite threads 422 on bone anchor 374. For example, engagement threads 394 can be right-hand threads while threads 422 are left-hand threads. As a result, rotation of crown nut 376 against bone anchor 374 does not cause bone anchor 364 to rotate concurrently. Furthermore, once crown nut 376 is initially positioned, nut driver 450 is removed. Anchor driver 436 can then be repositioned over fastener driver 400 so as to engage with bone anchor 374. Anchor driver 436 can then be used to back bone anchor 374 a distance back toward first end 94 of tunnel 90. In so doing, fastener 372 is further tensioned so as to increase the force securing condylar implant 300 on tibia 12. Again, because threads 394 and threads 422 rotate in opposite directions, backing bone anchor 374 does not cause crown nut 376 to unscrew.

Finally, once crown nut 376 and bone anchor 374 are positioned in their final state, fastener driver 400 is removed from fastener 372. Closing procedures for the tissue are then performed. In one alternative embodiment, bone anchor 374 can be eliminated. In this embodiment, crown nut 376 can be sized to bias directly against the bone so as to tension fastener 372. For example, crown nut 376 can be tapered to bias against the bone surrounding the opening at first end 94 of tunnel 90. In yet other embodiments, tunnel 90 can be counter bored so as to form a constricting shoulder within tunnel 90. Crown nut 376 can be configured to bias against the constricting shoulder of tunnel 90.

In still other embodiments, bone anchor 374 can be replaced with an insert that is fitted within tunnel and provides a hard bearing surface against which crown nut 376 can bear. For example, the insert can comprise a tubular member having a tapered exterior surface that biases against the bone and a tapered interior surface against which crown nut 376 can bias. In view of the foregoing, it is appreciated that crown nut 376 can have any desired configuration. Likewise, any type of attachment mechanism can be used to secure crown nut 367 to fastener 372.

Figure 23:
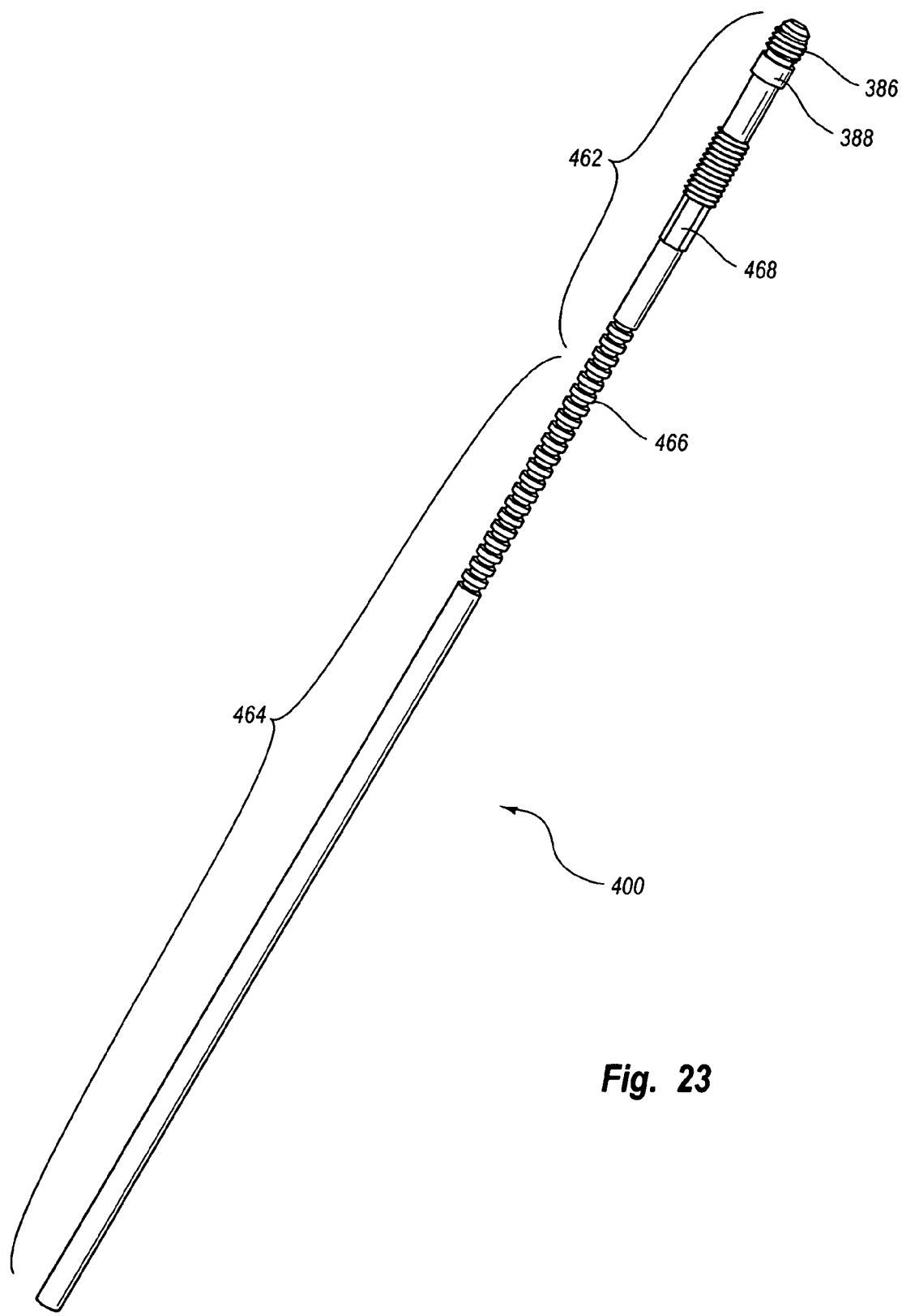
FIG. 23 is a perspective view of an alternative embodiment of the fastener shown in FIG. 17.

As discussed above, fastener driver 400 is useful as a guide in directing placement of bone anchor 374 and crown nut 376. In contrast to being separately connected to fastener 372, in one alternative embodiment the fastener driver can be integrally formed with fastener 372. For example, depicted in FIG. 23 is a fastener system 460. Fastener system 460 includes a fastener 462 and an elongated drive rod 464 integrally formed with fastener 462. Like elements between fasteners 372 and 462 are identified by like reference characters. As with fastener 372, fastener 462 includes flange 388 and threads 386 and 394. Formed proximal of threads 394 is a mating region 468. Mating region has a polygonal or other non-circular transverse cross section. As such removal or further tightening of fastener 462 can be accomplished by passing a tubular driver over fastener 462 so as to engage with mating region 468.

In contrast to socket 390 of fastener 372, fastener 462 is integrally formed with drive rod 464. To facilitate separation of drive rod 464 from fastener 462, a plurality of annular breaking grooves 466 encircle fastener system 460 at spaced apart locations along the junction between fastener 462 and drive rod 464.

Fastener system 460 is used in substantially the same manner as fastener 372 and fastener driver 400. However, once bone anchor 374 and crown nut 376 are finally positioned, fastener 462 and drive rod 464 are separated by breaking fastener system 460 at a annular breaking grooves 466 located adjacent to first end 94 of tunnel 90.

Figure 24:
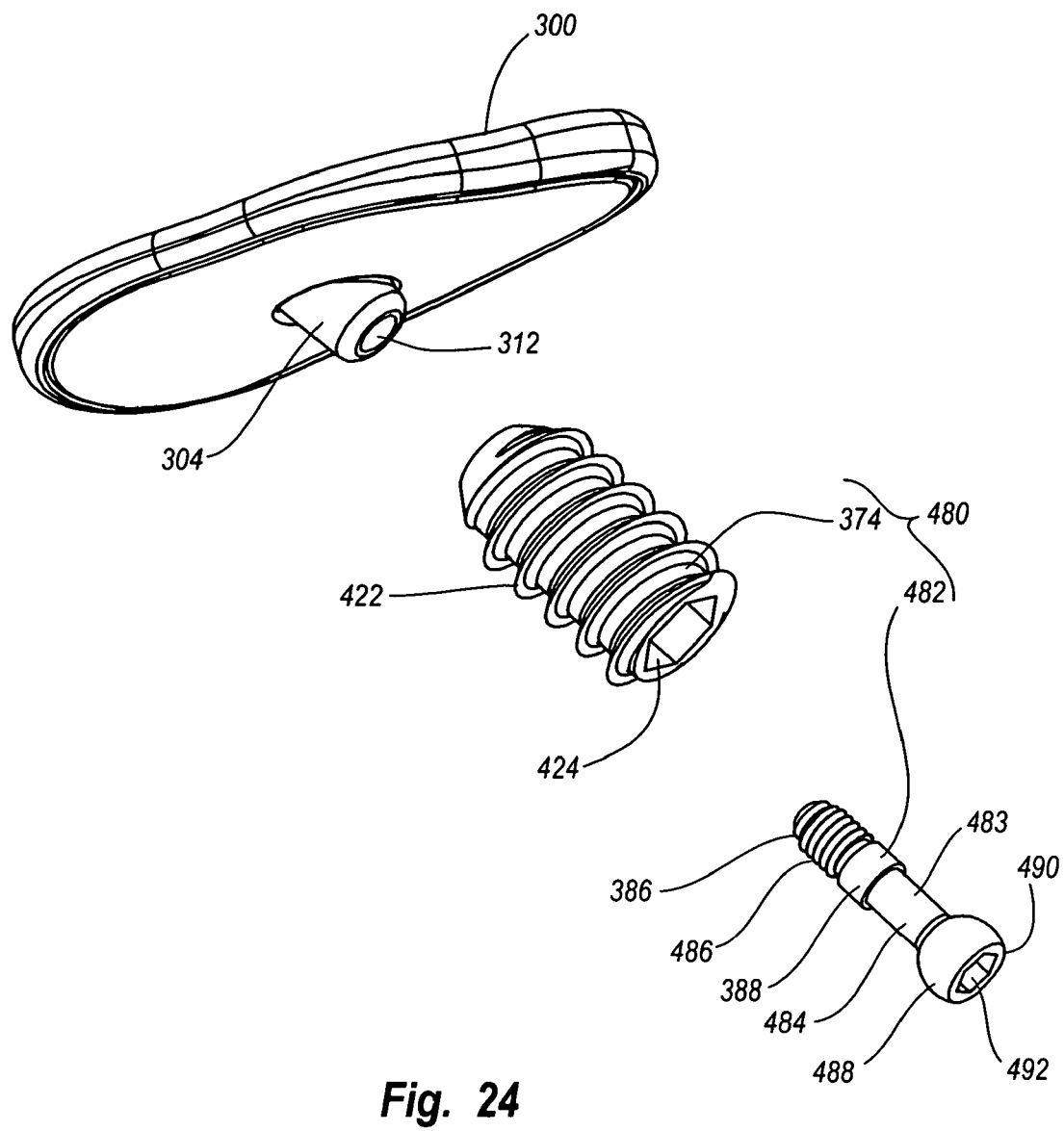
FIG. 24 is an alternative embodiment of an anchor assembly.

It is appreciated that the anchor assembly for condylar implant 300 can have a variety of different configurations. For example, depicted in FIG. 24 is an alternative embodiment of an anchor assembly 480. Anchor assembly 480 includes bone anchor 374, as discussed above, and a fastener 482. Like elements between fasteners 372 and 482 are identified by like reference characters. Fastener 482 includes a shaft 483 having a proximal end 484 and an opposing distal end 486. Mounted at or toward distal end 486 are threads 386 and flange 388 as discussed above. Mounted at proximal end 484 is an enlarged rounded head 488 that terminates at an end face 490. Recessed within end face 490 is a socket having a polygonal or other non-circular configuration. It is noted that head 488 has a maximum diameter that is smaller than the diameter of socket 424 of bone anchor 374 but larger than the minimum diameter of shoulder 432 of bone anchor 374. As such, head 488 seats against shoulder 432 when passed through bone anchor 374.

Figure 25:
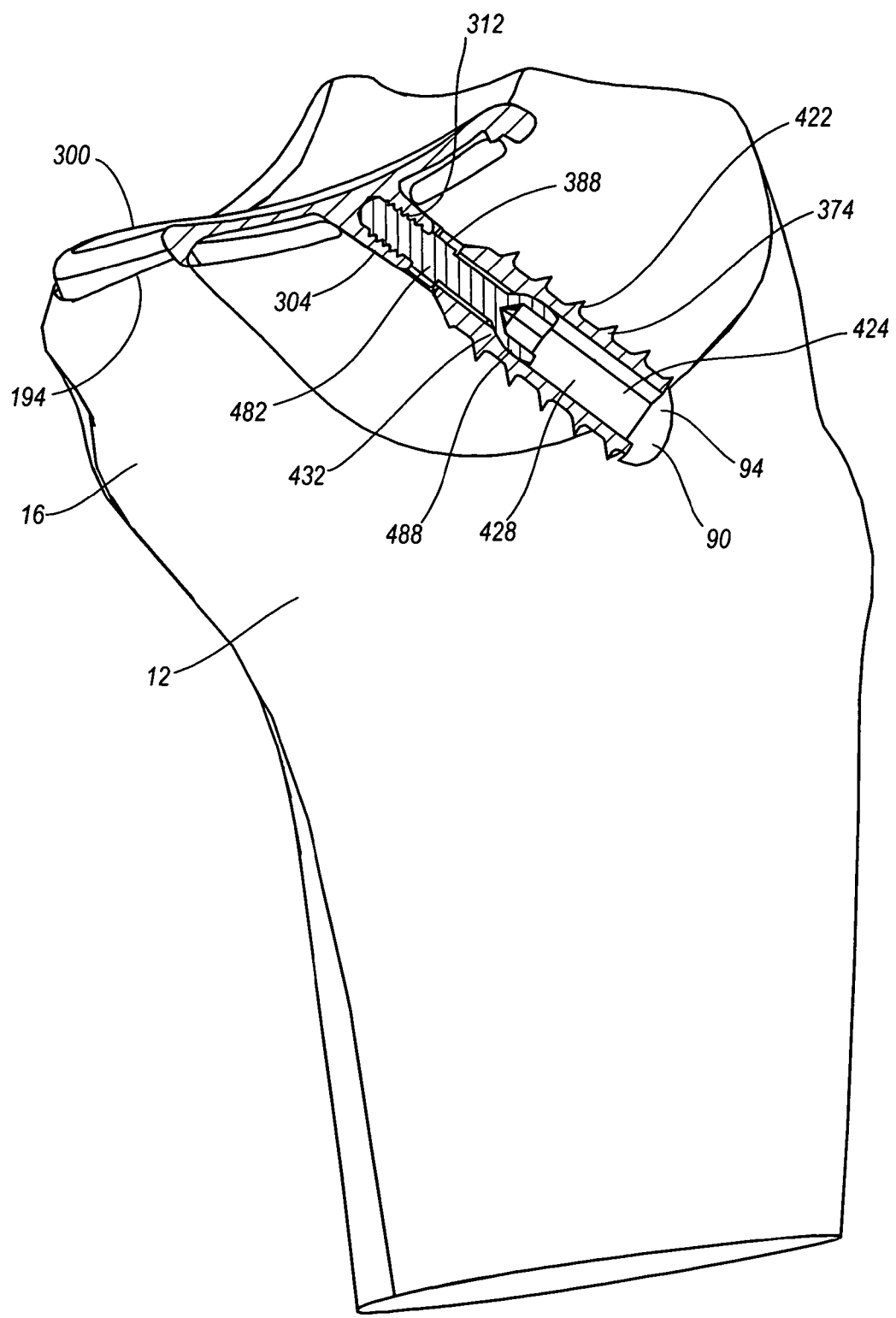
FIG. 25 is a cross section side view of the anchor assembly shown in FIG. 24 securing a condylar implant to a tibia.

Turning to FIG. 25, in contrast to anchor assembly 370 where fastener 372 is initially positioned, in anchor assembly 480 bone anchor 374 is initially secured within tunnel 90 using anchor driver 436. Again, tunnel 90 can be pre-tapped or threads 422 on bone anchor 374 can be self-tapping. Once bone anchor 374 is positioned, a driver, not shown, is inserted within socket 492 of fastener 482. The driver is then used to advance distal end 486 of fastener 482 into tunnel 90, through channel 424 of bone anchor 374, and into socket 312 of condylar implant 300. The driver is then used to rotate fastener 482 so that threads 386 threadedly engage with socket 312. Fastener 482 is advanced into socket 312 until flange 388 contacts the end face of stem 304. The driver for fastener 482 is then removed.

Next, anchor driver 436 is inserted back into socket 428 of bone anchor 374. This can be accomplished by passing anchor driver 436 over the driver for fastener 482 or by first removing the driver for fastener 482. Anchor driver 436 is then used to back bone anchor 374 a distance toward first end 94 of tunnel 90. In so doing, shoulder 432 of bone anchor 374 biases against head 488 of fastener 482, thereby tensioning fastener 482 so as to securely bias condylar implant 300 against tibia 12. It is appreciated that threads 386 of fastener 482 and threads 422 of bone anchor 374 rotate in opposite directions so that the backing of bone anchor 374 does not unscrew fastener 482 from condylar implant 300.

It is appreciated that in alternative embodiments the various threaded connections used in association with the anchor assemblies can be replaced with bayonet connections, expanding collets, press fit barb connections, and other conventional connections commonly used in place of thread connections.

In one embodiment of the present invention means are provided for securing a fastener to the bone apposition side of an implant after the bone apposition surface of the implant is biased against the natural or resected articulating surface of the bone such that applying increased tension to the fasten increases the force at which the bone apposition surface biases against the natural or resected articulating surface of the bone. Examples of such means, which can be formed on implant 300 or any other implant within the scope of the present invention, include stem 304 which projects from the bone apposition surface. Stem 304 can include threaded socket 312 or the other alternatives to threaded socket 312, as discussed above, which enable the connection of a fastener. Other examples of such means comprise the formation of threaded socket 312 directly on bone apposition surface as depicted in FIG. 13. In other alternatives, the threads of socket 312 can be replaced with barbs, bayonet connectors, adhesive, or other alternative forms of connectors. Other examples of such means are discussed with other embodiment disclosed below.

By using the above discussed implants and anchor assemblies with the corresponding methods and instruments, it is appreciated that the implants can be securely mounted to tibia 12 using procedures that are minimally invasive. Furthermore, because the implants are only secured in place after they are positioned on the proximal end of the tibia, the surgeon can easily switch out different sizes of implants when trying to determine an appropriate fit. Likewise, because the anchoring assemblies are operated through the first end of the tunnel which is remote from the implant, the inventive anchoring assemblies enable the surgeon to easily adjust the placement of the implant during initial positioning and to subsequently remove the implant should a replacement be required at a later date.

Because the inventive implants, anchor assemblies, tissue preparation instruments, and corresponding methods each produce independently unique benefits, it is appreciated that theses various features can be used independently with other conventional apparatus and techniques. For example, in one embodiment a larger incisions can be made at the knee of a patient and the proximal end of tibia 12 resected using conventional resection techniques. In this embodiment, tunnel 90 can be formed either before or after the resection of tibia 12. Once the tibia is resected and tunnel 94 formed, the above procedure can then be used to secure condylar implant 300. In another alternative, tunnel 94 can be formed and tibia 12 resected as discussed above. However, once tibia 12 is resected, a conventional implant can be mounted on tibia 12 using conventional techniques.

In one alternative, distal end 384 of fastener 372 can initially be mounted on or integrally formed with condylar implant 300 (FIG. 17) before implant 300 is positioned on the resected articulating surface. Proximal end 382 of fastener 372 can then be advanced into tunnel 90 from second end 96 (as opposed to first end 94) as implant 300 is being positioned on the resected articulating surface. As discussed above, the bone anchor and crown nut can then be used to secure fastener 372 within tunnel 90.

Figure 26:
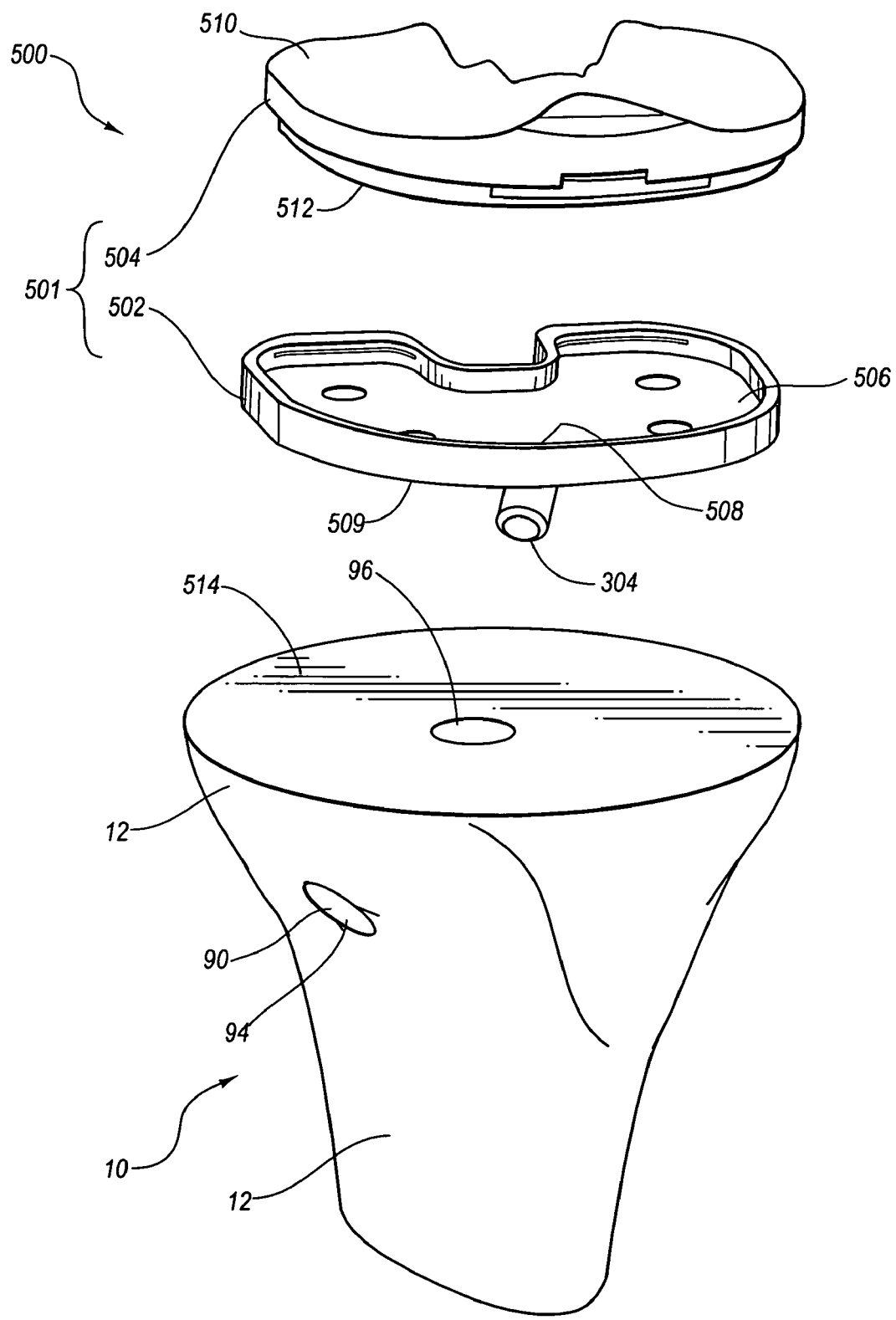
FIG. 26 is an exploded perspective view of an inventive full tibia implant for mounting on the proximal end of a tibia.

The above discussed embodiments relate to mounting a condylar implant on tibia 12. As previously mentioned, however, the present invention can also be used to mount other types of implants on other articulating surface so as to achieve one or more of the same benefits. For example, depicted in FIG. 26 is a full tibial implant 500. Tibial implant 500 comprises body 501 which includes a tray 502 and a bearing plate 504. Tray 502 has a top surface 506 and an opposing bone apposition surface 509. Top surface 506 bounds a pocket 508 which is configured to receive and lock bearing plate 504. Bearing plate 504 has a top articular surface 510 and a bottom surface 512 which is selectively snap fit within pocket 508 of tray 502.

In one embodiment, tray 502 is comprised of metal while bearing plate 504 is comprised of a polymeric material. It is noted that bearing plate 504 and tray 502, as discussed above, are well known in the art and can be replaced with a variety of other conventional bearing plates 504 and trays 502 used in full tibial implants. The distinction over the prior art, however, is that tray 502 has been modified so that stem 304, as previously discussed, projects from bone apposition surface 509.

As also depicted in FIG. 26, proximal end 10 of tibia 12 has been uniformly resected so as to form a resected articulating surface in the form of a tibial plateau 514. Tunnel 90 includes second end 96 formed on tibial plateau 514 and first end 94 spaced apart from tibial plateau 514. Tibia 12 can be resected to form tibial plateau 514 by using conventional techniques or by using a larger rasp assembly 100 in conjunction with retention rod 102 being disposed within tunnel 90. Depending on the method used, tunnel 90 can be formed before or after resection of tibia 12.

Once tibia 12 is resected, tray 502 is positioned on tibial plateau 514 so that stem 304 aligns with second end 96 of tunnel 90. One of the above discussed anchor assemblies is then used to secure tray 502 to tibia 12. Bearing plate 504 can be secured to tray 502 either before or after securing tray 502 to tibia 12.

In one alternative, by increasing the thickness of tray 502, stem 304 can be eliminated and replaced with socket 312 as discussed with regard to FIG. 13. Furthermore, one or more pockets can be formed on bone apposition surface 509 of tray 502 so as to receive one or more inlays of bone growth material.

Figure 27:
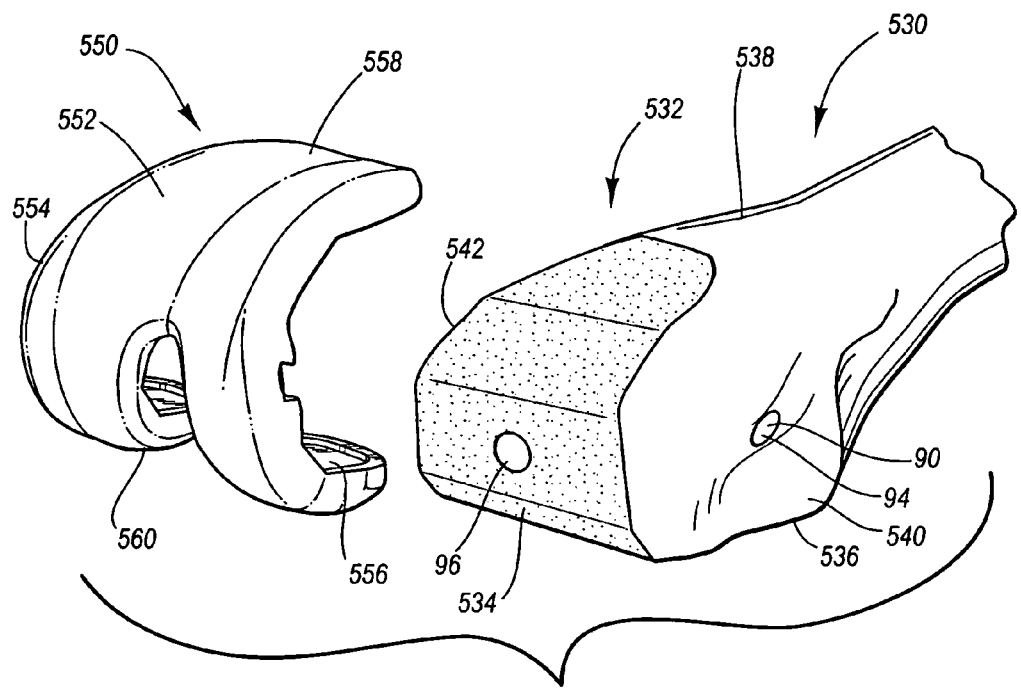
FIG. 27 is a perspective view of an inventive femoral implant for mounting on the distal end of a resected femur.

Features of the present invention can also be used for mounting a femoral implant on the distal end of a femur. Like elements between different embodiments are identified by like reference characters. For example, depicted in FIG. 27 is a distal end 532 of a femur 530. Femur 530 has a posterior side 536 and an anterior side 538 that each extend between a medial side 540 and a lateral side 542. The articulating surface at distal end 532, notably the femoral medial condyle and lateral condyle, have been resected so as to form a resected articulating surface 534.

Tunnel 90 is formed on femur 530. Second end 96 of tunnel 90 extends through resected articulating surface 534 while first end 94 of tunnel 90 is formed on medial side 540 at a location spaced apart from resected articulating surface 534. Tunnel 90 can be bored through femur 530 at an oblique angle α, as reflected in FIG. 30. In one embodiment the angle α is in a range between about 15° to about 50° with about 20° to about 40° being more common. Other angles can also be used. Tunnel 90 can be bored by making an incision in the skin adjacent femur 530, properly orienting a tubular alignment guide, then boring tunnel 90 with a drill through the alignment guide. In one embodiment tunnel 90 can be formed using a modified guide assembly similar to guide assembly 30 as previously discussed.

Figure 28:
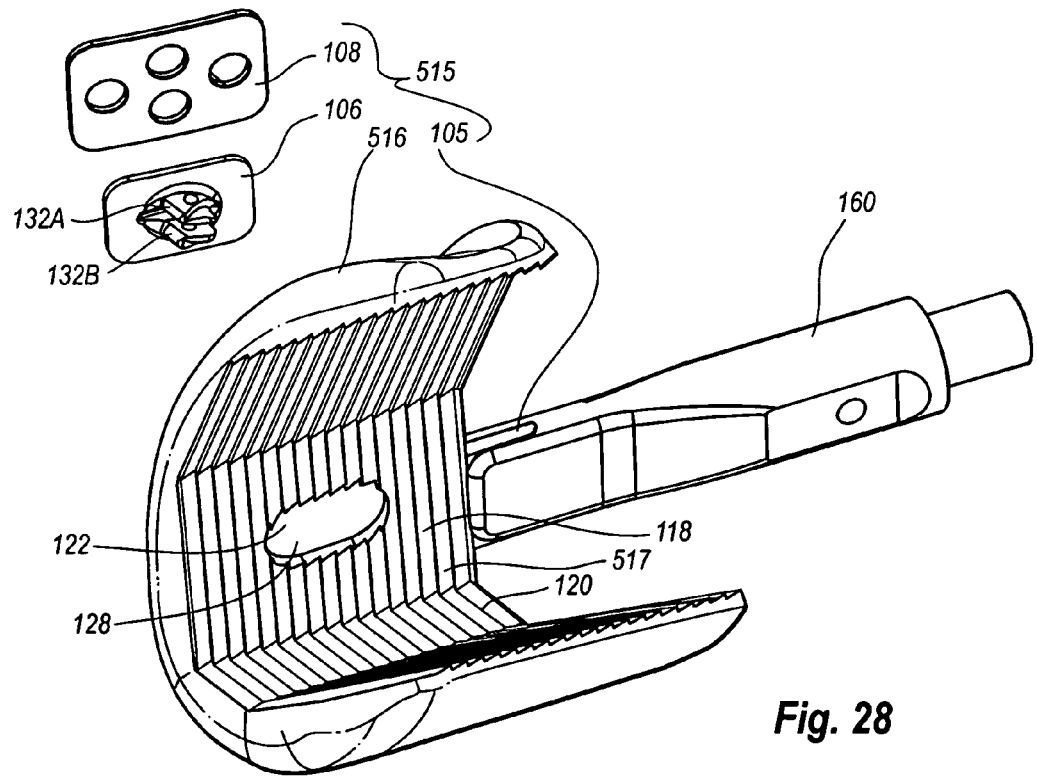
FIG. 28 is a perspective view of a femoral rasp assembly for resecting the distal end of a femur.

Resected articulating surface 534 can be formed using the present invention or other conventional resecting techniques. For example, depicted in FIG. 28 is a femoral rasp assembly 515 which has components similar to rasp assembly 100 previously discussed with regard to FIGS. 6-9. Femoral rasp assembly 515 comprises a substantially U-shaped rasp body 516, pivot arm 105, rasp guide 106, and cover plate 108.

Insertion handle 160 is show removably disposed over pivot arm 105 and, if desired, can be used to initially place rasp assembly 515 on femur 530. Rasp body 516 has a substantially concave cutting surface 517 having a plurality of ridges 118 formed thereon. Ridges 118 each terminate at sharpened cutting edge 120. It is appreciated that ridges 118 and cutting edges 120 can be at any desired orientation or combination of different orientations that facilitate cutting.

As with rasp assembly 100, extending through rasp body 516 is guide slot 122 and opening 128. Rasp guide 106 is received within guide slot 122 so that forks 132A-B pass through opening 128. Cover plate 108 secures rasp guide 106 within guide slot 122.

During operation, rasp assembly 515 is mounted on the distal end of femur 530 such that forks 132A and B of rasp guide 106 are aligned with second end 96 of tunnel 90. Once rasp assembly 515 is positioned, retention rod 102 (FIGS. 8 and 9) is advance within tunnel 90 from first end 94 and connected to rasp guide 106 as previously discussed.

Once retention rod 102 is secured to rasp assembly 515, insertion handle 160 is removed and a reciprocal driver, such as a reciprocal saw, is connected pivot arm 105. While holding rasp guide 106 substantially stationary by holding onto retention rod 102, the reciprocal driver rapidly reciprocates rasp body 516 so that cutting edges 120 resects the distal end of femur 530. In the embodiment depicted, rasp body 516 is only designed to resect the medial side of the distal end of femur 530. A complementary rasp assembly can then be used to resect the lateral side of the distal end of femur 530 using a second tunnel 90 extending through lateral side 542 of femur 530, thereby forming resected articulating surface 534.

Figure 29:
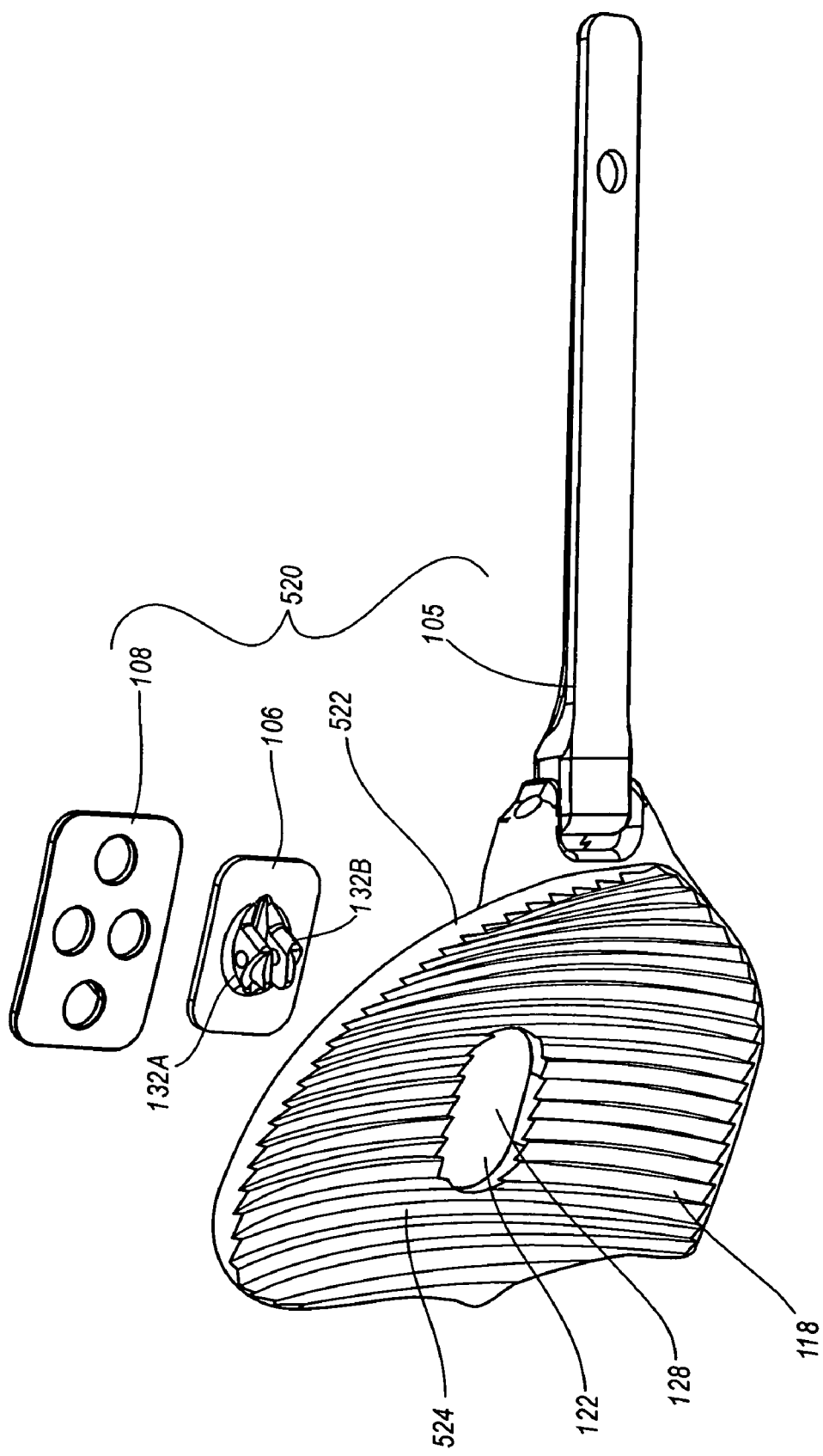
FIG. 29 is a perspective view of an alternative embodiment of a femoral rasp assembly for resecting the distal end of a femur.

In yet other embodiments, it is appreciated that multiple different rasp assemblies with one or more different tunnels can be used to resect femur 530 or a single rasp assembly can be configured to simultaneously resect the entire distal end of femur 530. For example, depicted in FIG. 29 is another embodiment of a femoral rasp assembly 520. Rasp assembly 520 comprises an arched rasp body 522, pivot arm 105, rasp guide 106, and cover plate 108. Rasp body 522 has a substantially concave cutting surface 524 having a plurality of ridges 118 formed thereon. As with rasp body 516, extending through rasp body 522 is guide slot 122 and opening 128. Rasp guide 106 is received within guide slot 122 so that forks 132A-B pass through opening 128. Cover plate 108 secures rasp guide 106 within guide slot 122.

Rasp body 522 is configured to primarily resect the anterior surface at the distal end of femur 530. As such, a corresponding tunnel 90 is need on femur 530 to ensure proper placement of rasp body 522 during resection. A complementary rasp body is then be used to resect the remainder of the distal end of femur 530. For example, depicted in FIGS. 33-39 are alternative embodiments of two piece femoral implants. Corresponding two piece rasp bodies can be formed to resect the corresponding surfaces that receive the pieces of the femoral implants.

Furthermore, it is also appreciated that although resected articulating surface 534 is shown having a plurality of planar faces, in alternative embodiments the one or more rasp assemblies can be configured so as to produce resected articulating surface 534 having a continuous smooth arched surface or combinations of different surfaces.

Figure 30:
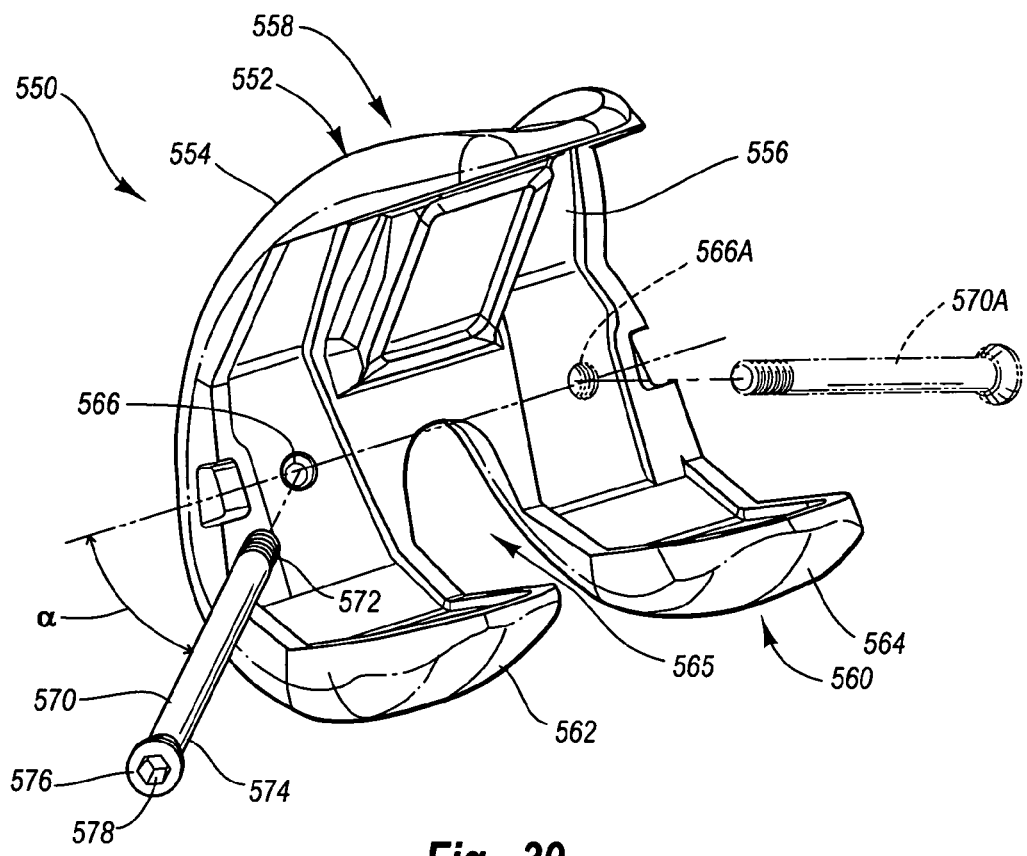
FIG. 30 is an inside perspective view of the femoral implant shown in FIG. 27.

In one embodiment of the present invention, a femoral implant 550 is provided incorporating features of the present invention. As depicted in FIGS. 27 and 30, femoral implant 550 comprises a substantially U-shaped body 552 having an articular surface 554 and an opposing bone apposition surface 556 which each extend between an anterior end 558 and a posterior end 560. Articular surface 554 is configured to mate with a tibia or tibial implant while bone apposition surface 556 is configured to mate with resected articulating surface 534 of femur 530.

More specifically, body 552 of femoral implant 550 comprises a substantially U-shaped medial condyle 562 and a substantially U-shaped lateral condyle 564. Condyles 562 and 564 are connected together at anterior end 558 but are spaced apart at posterior end 560 so that an elongated slot 565 is formed thereat. In an alternative embodiment, the femoral implant can comprise a unicondylar femoral implant which independently comprises medial condyle 562 or lateral condyle 564. It is appreciated that where only one of medial condyle 562 or lateral condyle 564 is being implanted, it is necessary only to resect one of the medial condyle or lateral condyle at the distal end of femur 530.

Formed on bone apposition surface 556 of medial condyle 562 is a threaded socket 566. In alternative embodiments, socket 556 can be replaced with outwardly projecting stem 304 as previously discussed with regard to FIG. 12. Stem 304 can have external threads or a socket with internal threads. In turn, the threads can be replaced with bayonet connectors or other alternatives as previously discussed.

As also depicted in FIG. 30, a fastener 570 is provided. Fastener 570 has a distal end 572 with threads formed thereat and an opposing proximal end 574. An enlarged head 576 is formed at proximal end 574 and has a polygonal socket 578 to receive a drive rod. Distal end 572 is configured to mate with socket 566. In alternative embodiments, distal end 572 can be modified to mate with the above discussed alternatives that can replace socket 566.

Figure 31:
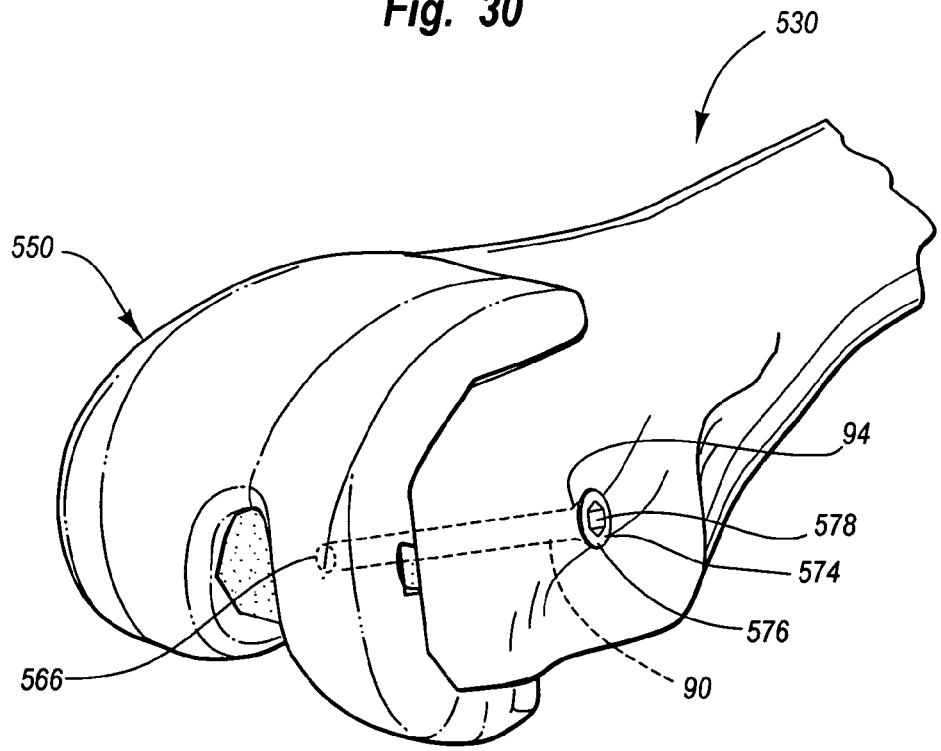
FIG. 31 is a perspective view of the femoral implant shown in FIGS. 27 and 30 mounted to the femur shown in FIG. 27.

During use femoral implant 550 is positioned on resected articulating surface 534 so that socket 566 is aligned with second end 96 of tunnel 90. Here it is appreciated that because there are no posts projecting from bone apposition surface 556, femoral implant 550 can be slide on to resected articulating surface 534 lateral to medial or medial to lateral through a medial or lateral incision on the knee of the patent. As a result, it is not necessary to openly expose distal end 532 of femur 530 during placement of femoral implant 550. As depicted in FIG. 31, once tunnel 90 and socket 566 are aligned, distal end 572 of fastener 574 is placed in first end 94 of tunnel 90 and advanced through tunnel 90. By inserting a driver into socket 578, fastener 570 is selectively rotated so that first end 572 threaded into socket 566. Enlarged head 576 biases against femur 530 so as to securely bias femoral implant 550 against femur 530.

In one alternative embodiment, enlarged head 576 can be threaded or otherwise mounted on proximal end 574 such that screwing head 576 onto the shaft of fastener 570 causes head 576 to bias against the bone and thereby tension fastener 570. In this embodiment head 576 would function as a crown nut.

In contrast to using fastener 574, it is appreciated that anchor assembly 370 or 480, as previously discussed with regard to FIGS. 17 and 24, or their discussed alternatives can be used to secure femoral implant 550 to femur 530. Furthermore, as depicted in FIG. 30, in one alternative embodiment a second socket 566A can be formed on bone apposition surface 556 of lateral condyle 564. A second fastener 570A can be passed through a second tunnel on the lateral side of femur 530 to couple with second socket 566A, thereby further securing femoral implant 550 to femur 530. Alternatively, second fastener 570A can be used instead of first fastener 570.

Figure 32:
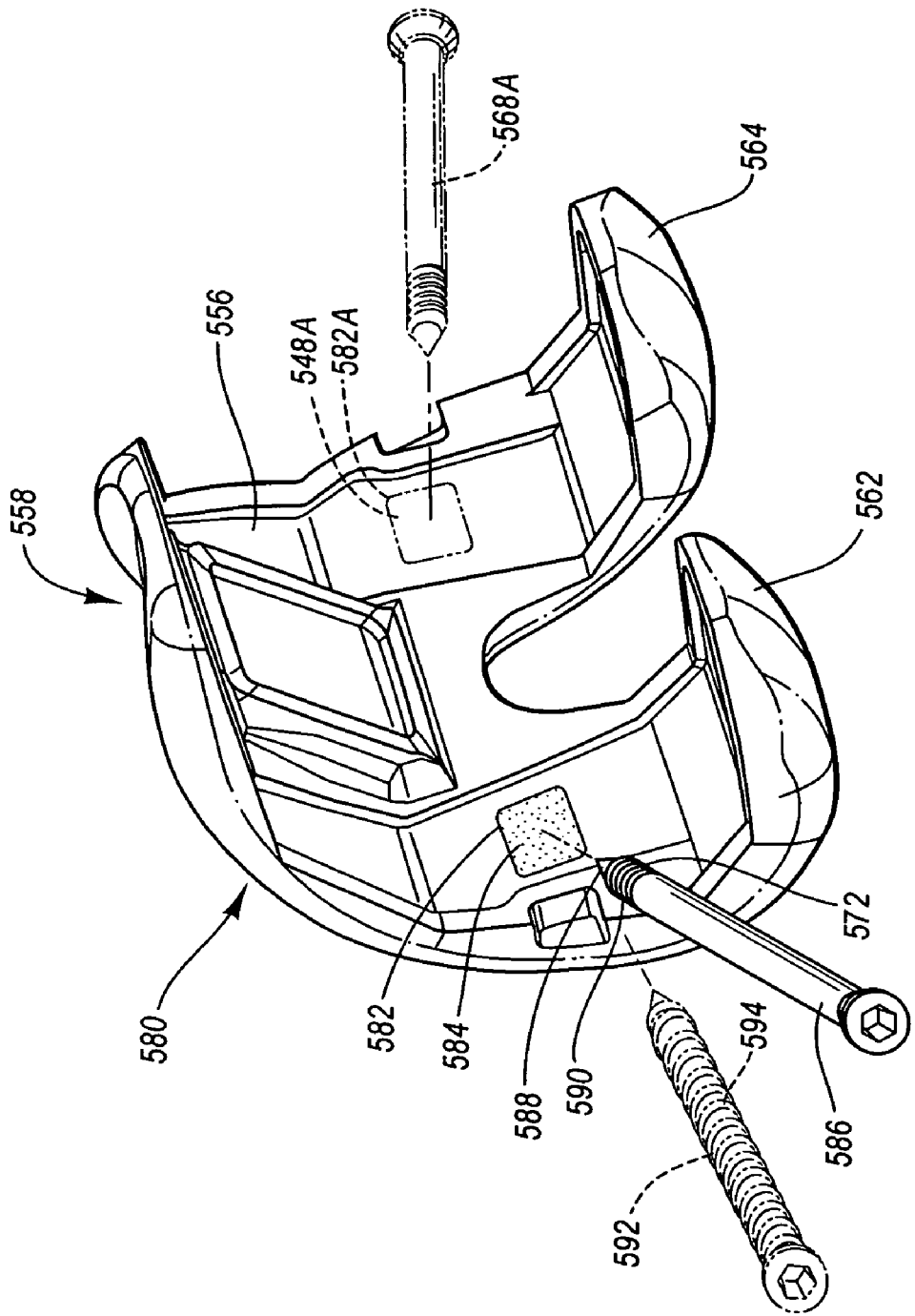
FIG. 32 is a perspective view of an alternative embodiment of the femoral implant shown in FIG. 30.

Depicted in FIG. 32 is an alternative embodiment of a femoral implant 580 incorporating features of the present invention. Again, like elements of different embodiments are identified by like reference characters. In contrast to threaded sockets 566 of femoral implant 558, femoral implant 580 comprises an enlarged socket 582 filled with a curable adhesive 584 such as polymethylmethacrylate or the like. In yet other embodiments, socket 582 can be filled with a polymer such as Delrin, polyetheretherketone, or the like that is capable of receiving and deforming to the shape of a fastener received therein.

A fastener 586 is also depicted in FIG. 32. Distal end 572 of fastener 586 terminates at a pointed nose 588. Threads or ribs 590 are disposed adjacent to pointed nose 588. In this embodiment, because of pointed nose 588, fastener 586 can simply be driven through femur 530, such as by being impacted with a hammer or other tool, without the prior formation of tunnel 90. As ribs 590 are received within socket 582, the material therein cures or deforms around threads or ribs 590 so as to secure fastener 586 to femoral implant 580, thereby securing femoral implant 580 to femur 530. Alternatively, fastener 586 can also be used in association with tunnel 90. In yet another alternative embodiment, fastener 586 can be replaced with a fastener 592. Fastener 592 has a helical screw thread 594 extending along the length thereof. As such, fastener 592 can be screwed into femur 530 so as to engage with femoral implant 580 with or without prior formation of tunnel 90.

In one embodiment, in addition to the use of a fastener to attach the femoral implant to the femur 530, a bone cement can be employed to further enhance the adhesion of the femoral implant to resected femur 530. The bone cement can be applied before and/or during mounting of the femoral implant. For example, the femoral implant can be partially attached and then a syringe or other form of delivery tube used to inject bone cement between the femoral implant and femur 530. In addition, a porous or fibrous material, such as a wire mesh, may be attached to bone apposition surface 556 of the femoral implant to thereby foster bone growth between the femoral implant and resected femur 530 and/or to provide surface area for attaching the bone cement between the femoral implant and resected femur 530. In one embodiment, one more pockets can be formed on bone apposition surface 556. An inlay of porous bone ingrowth, such as previously discussed with regard to inlay 320, can be secured within the pockets.

Depicted in FIGS. 33-39 are connectible two-piece femoral implants incorporating features of the present invention. The implants can be used in knee arthroplasty wherein the two parts are independently slid in from the medial or lateral side of the knee through an incision and then connected and mounted onto resected articulating surface 534 of femur 530. A coupling member, such as a bolt, screw, pin, or the like, can be used to attach one part of the femoral implant to the other. Optionally, one part may be mounted on resected articulating surface 534 followed by the other part being connected thereto. A fastener is passed through femur 530, as discussed above, to connect the femoral implant to femur 530. Because the smaller parts of the two-piece femoral implant can be sequentially inserted through an incision, the required incision can be smaller than required for unitary implants.

Figure 33:
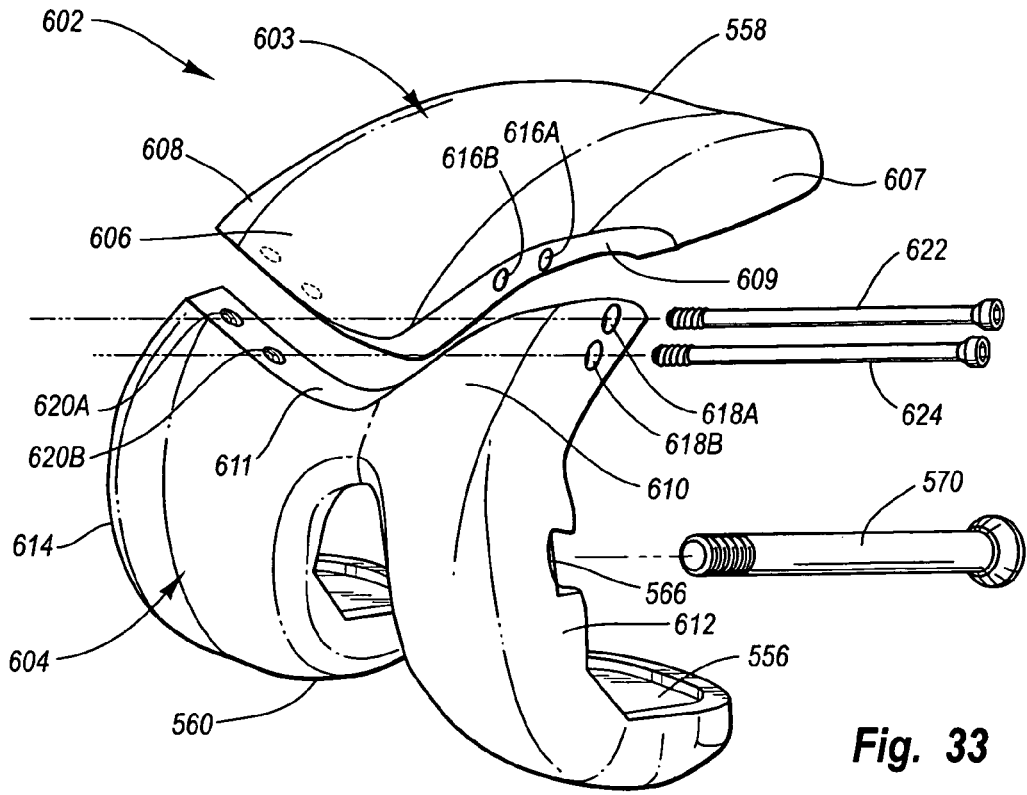
FIG. 33 is a perspective view of a laterally bisected, two-piece femoral implant in a disassemble state.
Figure 34:
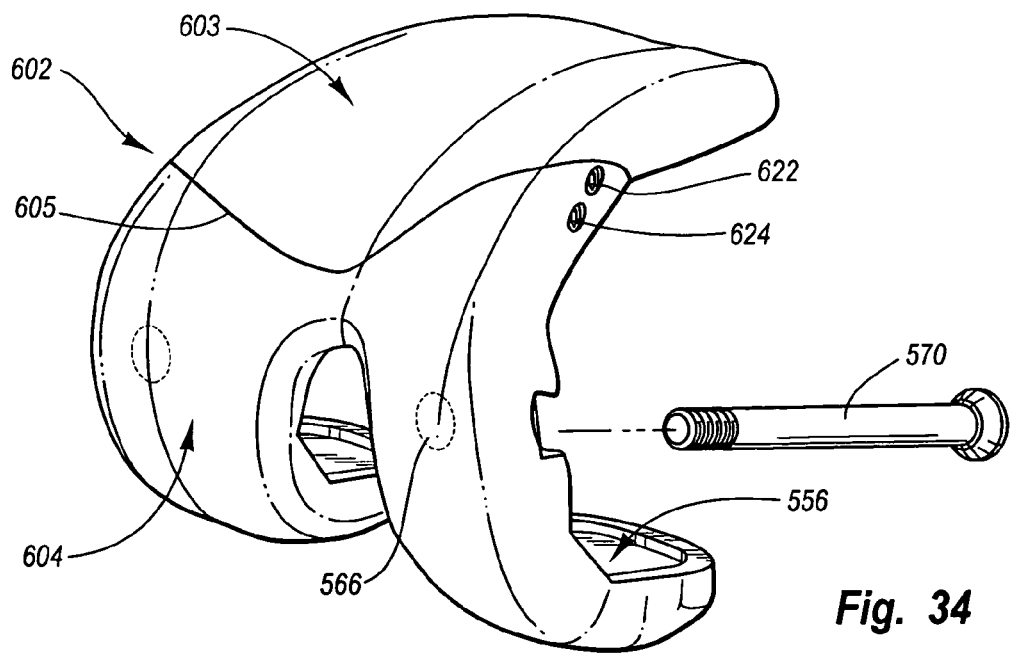
FIG. 34 is a perspective view of the implant shown in FIG. 33 in an assembled state.

FIG. 33 is a perspective view of a two-piece femoral implant 602 in a divided state while FIG. 34 is a perspective view of femoral implant 602 shown in an assembled state. In one embodiment, femoral implant 602 can be designated as "end use" in that the entire structure is configured to be permanently mounted onto the resected articulating surface during a resurfacing procedure and is designed for permanent daily use by a patient.

Femoral implant 602 is centrally divided lateral to medial and comprises a patellar condyle 603, which includes anterior end 558, and a tibial condyle 604, which includes posterior end 560. Patellar condyle 603 includes at a substantially V-shaped posterior end 606. Posterior end 606 terminates at an end face 609 that extends between a medial side 607 and a lateral side 608 of patellar condyle 603. A pair of spaced apart linear passageways 616A-B transversely extend through posterior end 606 of patellar condyle 603 so as to enter and exit through end face 609.

Tibial condyle 604 terminates at a V-notched anterior end 610 that is complementary to V-shaped posterior end 606 of patellar condyle 603. Anterior end 610 terminates at an end face 611 that also extends between a medial side 612 and lateral side 614 of tibial condyle 604. A pair of spaced apart passageways 618A-B transversely extend through anterior end 610 of tibial condyle 604 between medial side 612 and end face 611. A pair of threaded sockets 620A-B are formed on end face 611 toward lateral side 614 in alignment with passageways 618A-B.

When patellar condyle 603 and tibial condyle 604 are mated, a joint line 605 is formed at the intersection. In one embodiment, joint line 605 is positioned so that it corresponds to the location of the sulcus of femur 530 when femoral implant 602 is mounted on femur 530. In the mated position, passageways 616A-B, passageways 618A-B, and sockets 620A-B are aligned. As a results, bolts 622 and 624 having threaded ends can be passed through passageways 616A-B, 618A-B and screwed into sockets 620A-B so as to securely connect patellar condyle 603 and tibial condyle 604. It is appreciated that bolts 622 and 624 can be replaced with a variety of other structures to connect patellar condyle 603 and tibial condyle 604.

Femoral implant 602 further comprises socket 566 formed on bone apposition surface 556 of tibial condyle 604. As a result, fasteners 570 or anchor assemblies 370 or 480 can secure femoral implant 602 to femur 530 as discussed in the above embodiments.

Figure 35:
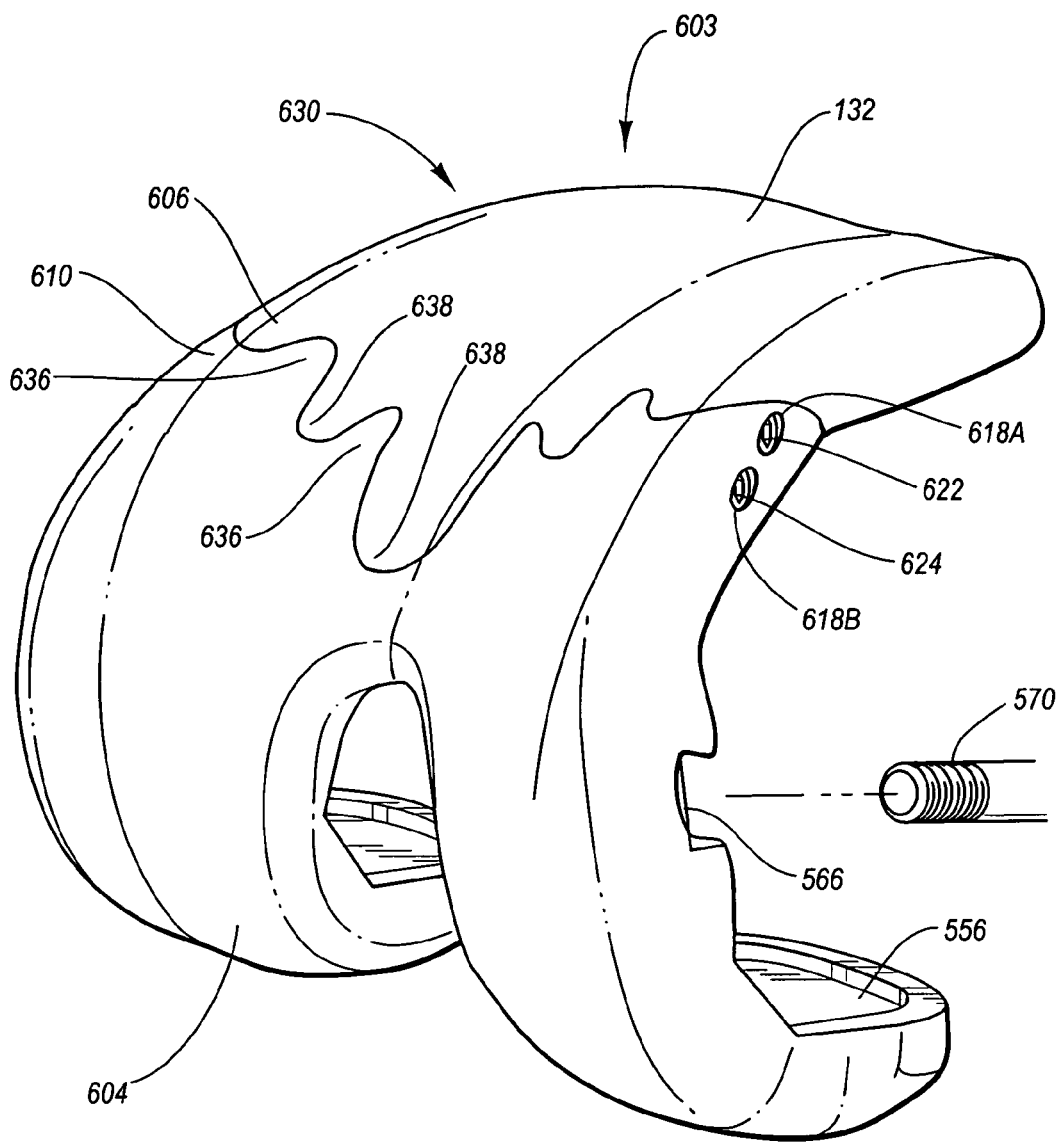
FIG. 35 is a perspective view of an alternative embodiment of the implant shown in FIGS. 33 and 34.

Depicted in FIG. 35 is a femoral implant 630 that is substantially the same as femoral implant 602. The only difference is that interlocking teeth 636 and 638 are formed along posterior end 606 of patellar condyle 603 and anterior end 610 of tibial condyle 604, respectively. Interlocking teeth 636 and 638 provide greater engagement and stability between patellar condyle 603 and tibial condyle 604.

Figure 36:
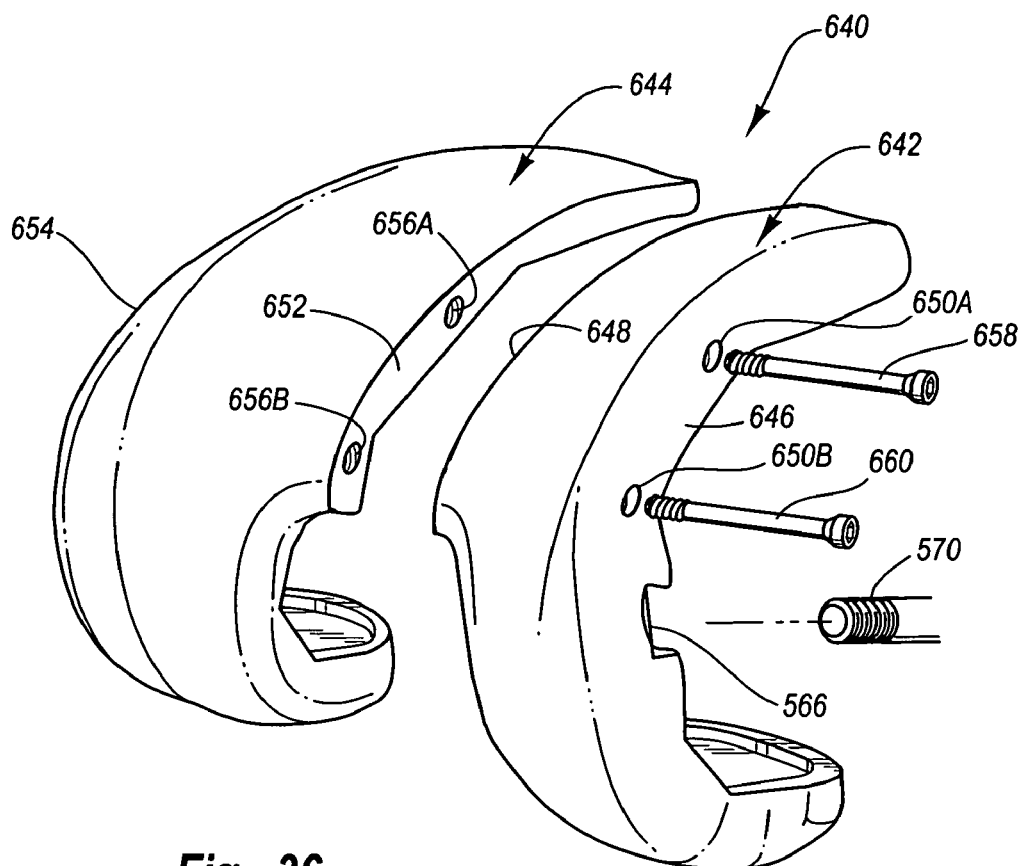
FIG. 36 is a perspective view of a longitudinally bisected, two-piece femoral implant in a disassemble state.
Figure 37:
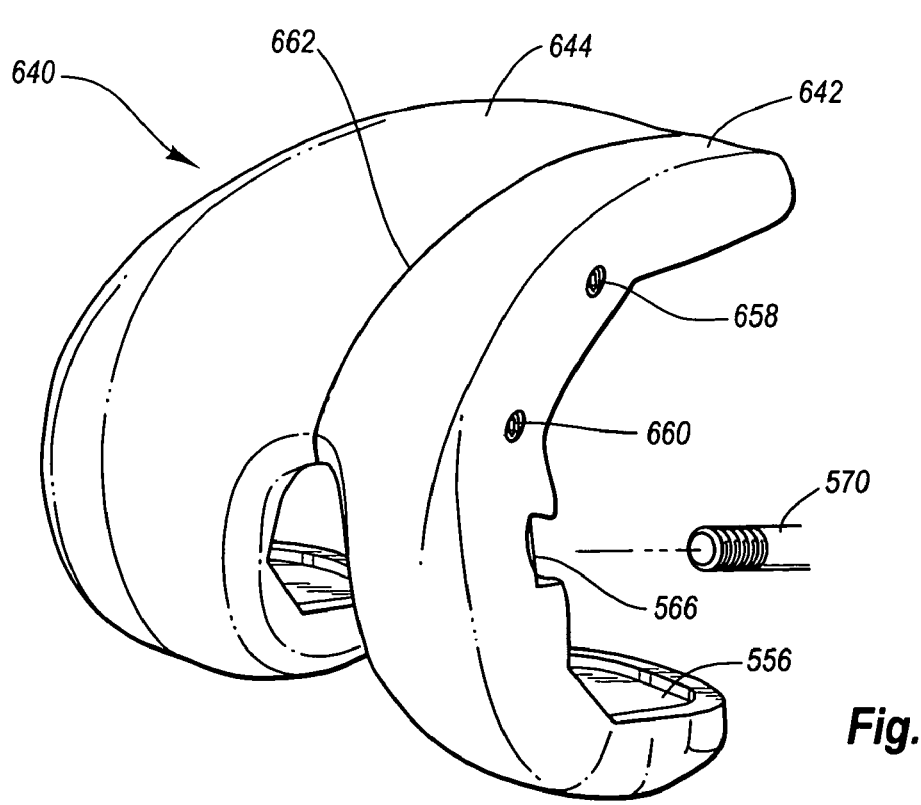
FIG. 37 is a perspective view of the implant shown in FIG. 36 in an assembled state.

Depicted in FIGS. 36 and 37 is another alternative embodiment a two-piece femoral implant 640. Femoral implant 640 is centrally divided anterior to posterior so as to comprise a substantially U-shaped medial condyle 642 a substantially U-shaped lateral condyle 644. Medial condyle 642 has a medial side face 646 and a lateral side face 648. A pair of spaced apart passageways 650A-B transversely extend through medial condyle 642 between side faces 646 and 648.

Lateral condyle 644 also has a medial side face 652 and a lateral side face 654. A pair of spaced apart threaded sockets 656A-B are formed on medial face 652 of lateral condyle 644. When condyles 642 and 644 are mated, a joint line 662 is formed at the intersection. In one embodiment, joint line 662 is positioned so that it corresponds to the location of the trochlear groove of femur 530 when femoral implant 640 is mounted on femur 530. In the mated position, passageways 650A-B are aligned with threaded sockets 656A-B. As a result, fasteners 658 and 660 each having a threaded end can be selectively passed through passageways 650A-B and screwed into sockets 656A-B so as to secure condyles 642 and 644 together.

Figure 38:
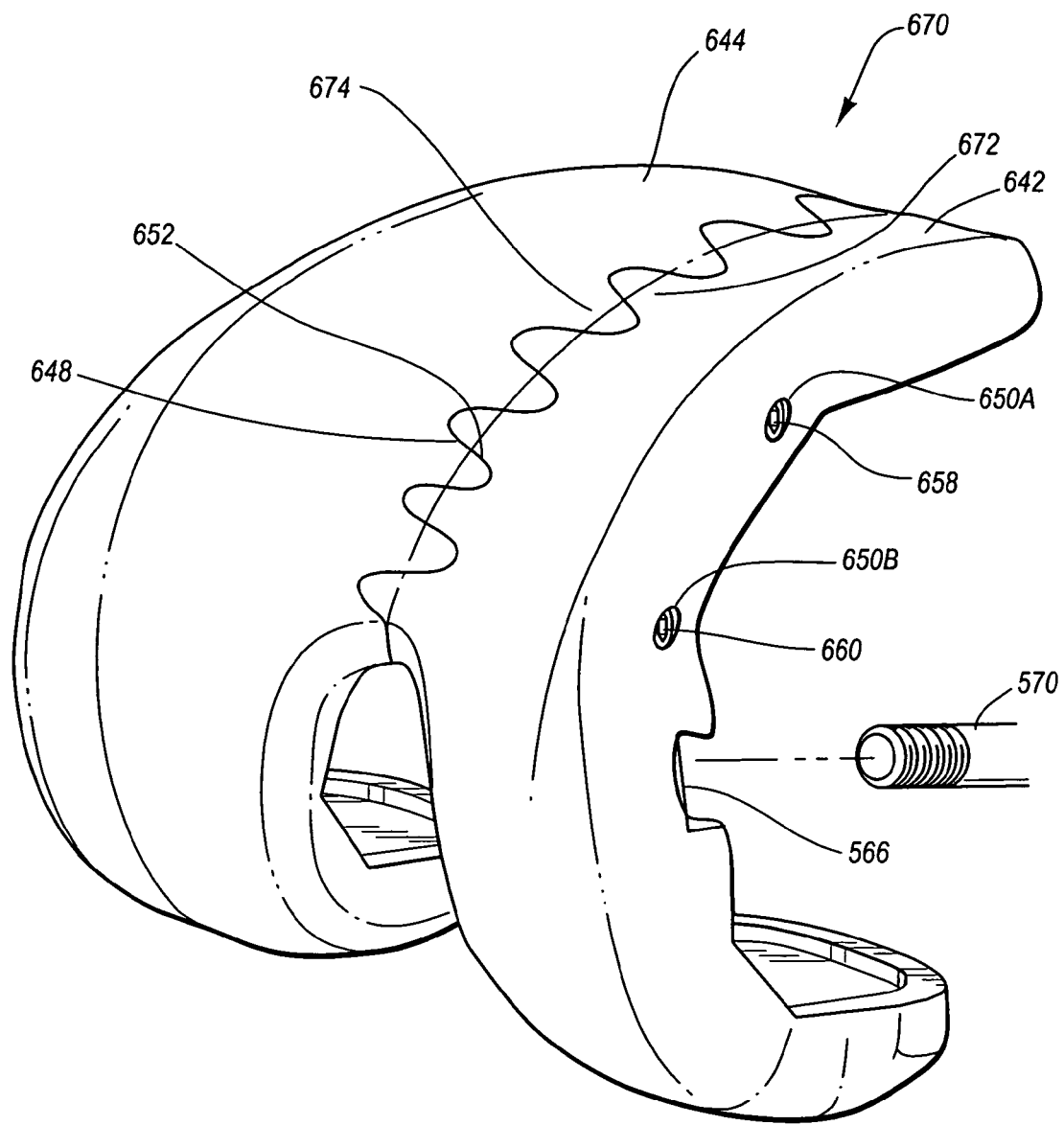
FIG. 38 is a perspective view of an alternative embodiment of the implant shown in FIGS. 36 and 37.
Figure 39A:
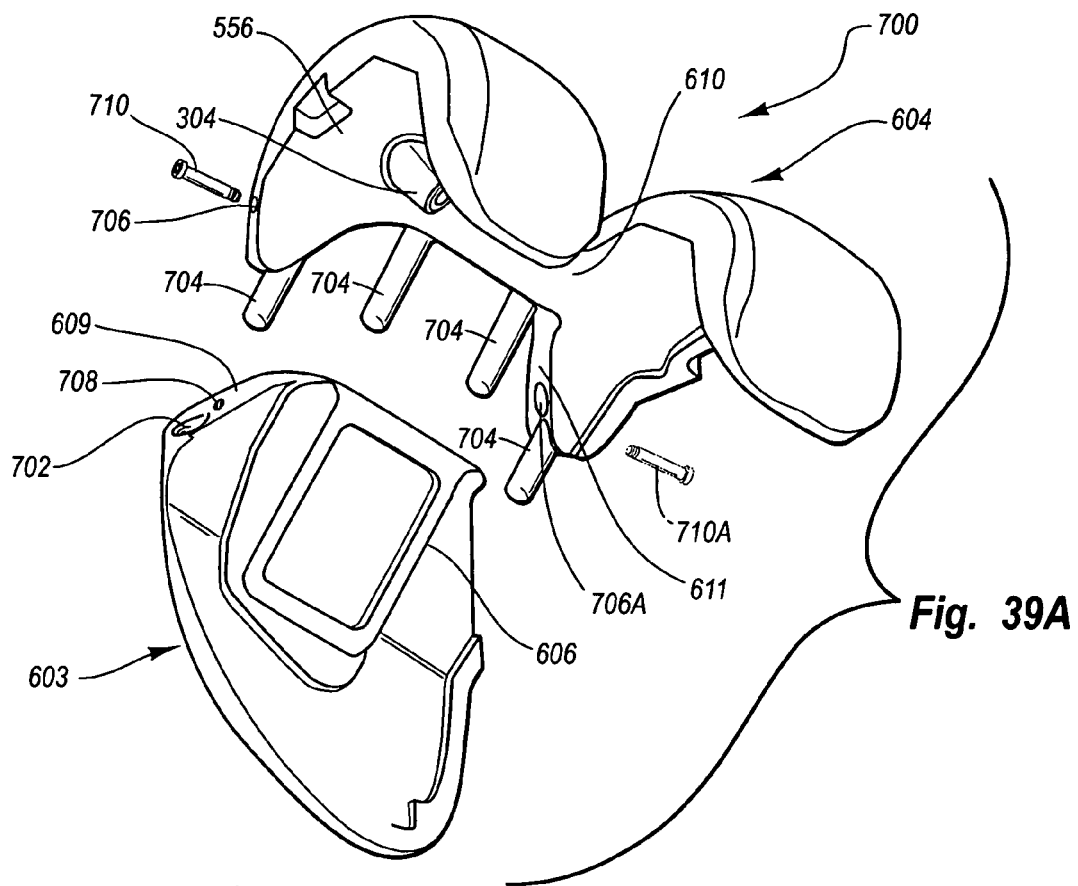
FIGS. 39A-D are perspective views of another alternative embodiment of a laterally bisected, two-piece femoral implant.
Figure 39B:
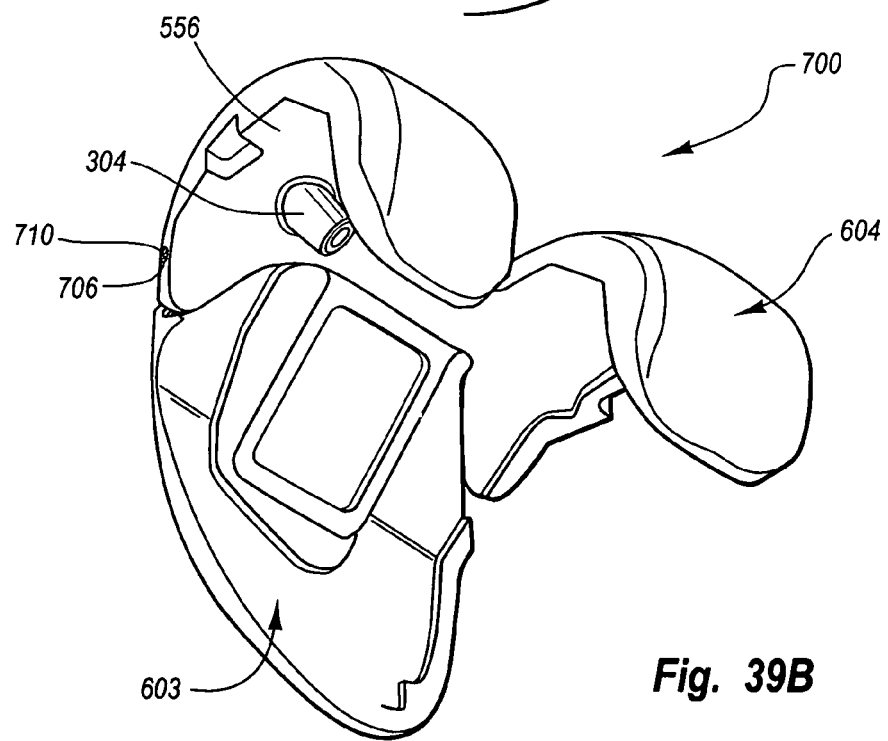
Figure 39C:
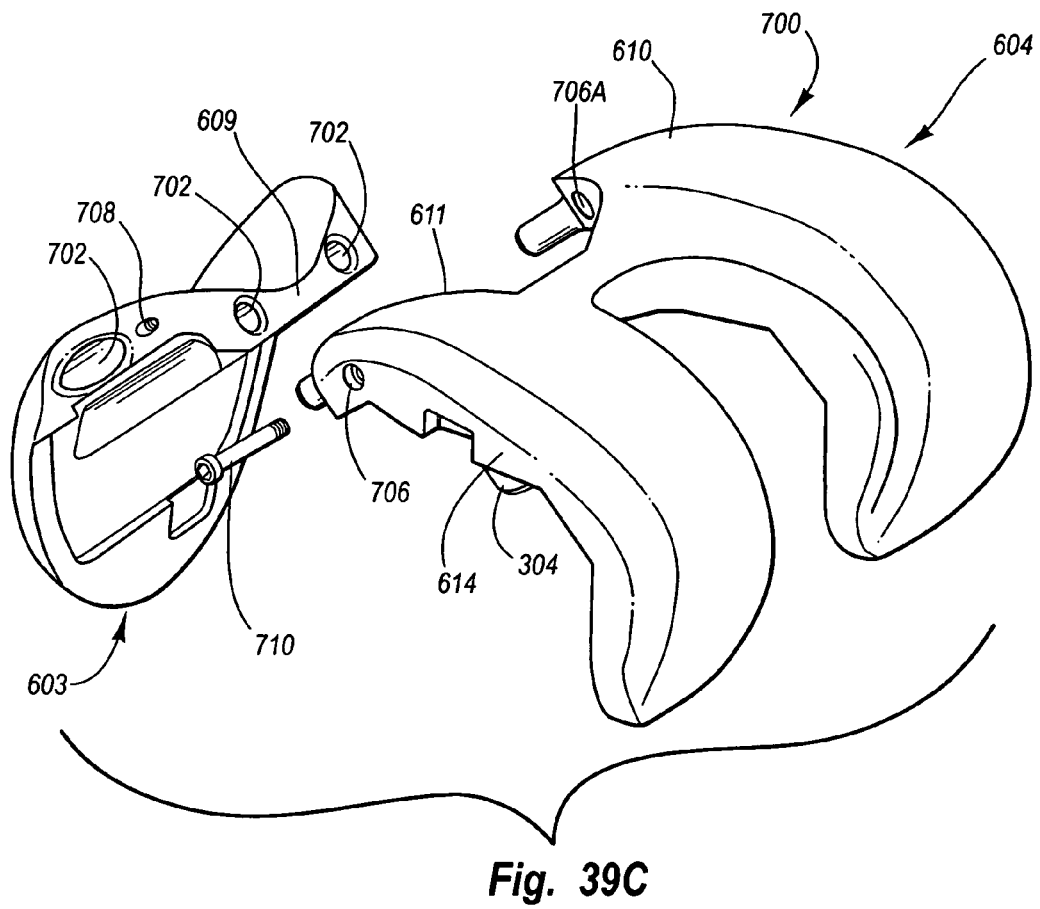
Figure 39D:
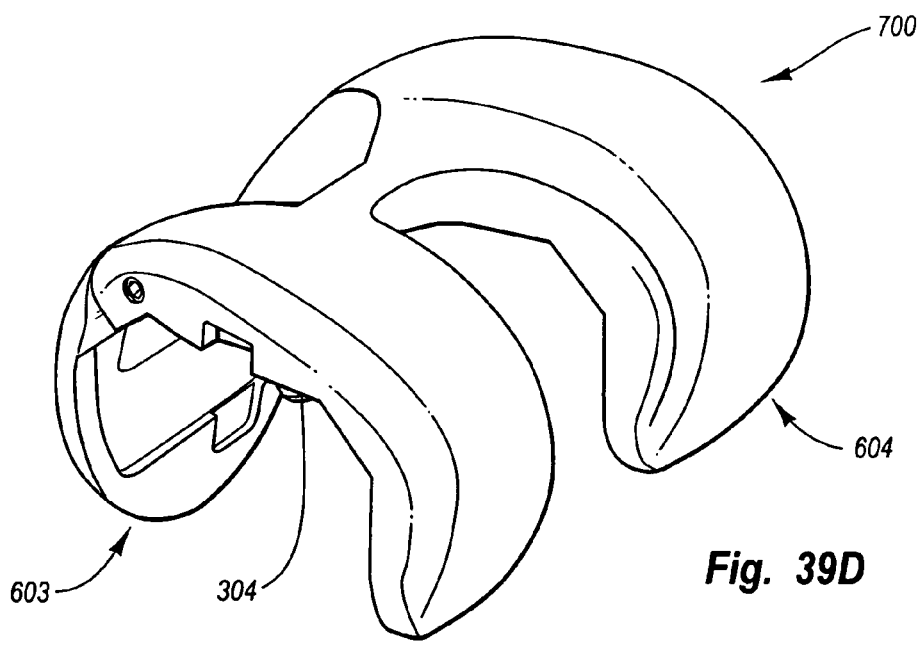

Depicted in FIG. 38 is a femoral implant 670 that is substantially the same as femoral implant 640. The only difference is that a plurality of interlocking teeth 672 and 674 are formed along lateral side face 648 of medial condyle 642 and medial side face 652 of lateral condyle 644, respectively.

Interlocking teeth 672 and 674 provide greater engagement and stability between medial condyle 642 and lateral condyle 644.

Depicted in FIGS. 39A-D is another embodiment of a two-piece femoral implant 700 incorporating features of the present invention. Femoral implant 700 is substantially similar to implant 602 discussed above with regard to FIGS. 33 and 34. As such, like elements are identified by like reference characters. In contrast to implant 602, a plurality of spaced apart holes 702 are formed on end face 609 of posterior end 606 of patellar condyle 603. A plurality of spaced apart pegs 704 project from end face 611 of anterior end 610 of tibial condyle 604. Pegs 704 are formed complementary to holes 702 such that when patellar condyle 603 and tibial condyle 604 are mated together, pegs 704 are received within holes 702 so as to rigidly hold condyles 603 and 604 together.

In contrast to having a pair of bolts transversely extending across patellar condyle 603 in femoral implant 602, femoral implant 700 comprises a passageway 706 that extends from lateral side 614 of tibial condyle 604 to end face 611 at anterior end 610 of tibial condyle 604. A threaded socket 708 is formed on end face 609 of posterior end 606 of patellar condyle 603. When condyles 603 and 604 are mated, passageway 706 and socket 708 are aligned. A bolt 710 having a threaded end is passed through passageway 706 and screwed into socket 708 so as to secure condyles 603 and 604 together. In one alternative, a complementary passageway 706A and socket 708A can also be formed on the medial side of condyles 603 and 604 to provide further engagement by a bolt 710A.

Finally in contrast to have socket 566 to receive fastener 570, tubular stem 304 is formed on bone apposition surface 556 of tibial condyle 604. Stem 304 is designed to mate to fastener 570 or the other anchor assemblies as previously discussed. Alternatively, stem 304 can be replaced with socket 566.

Figure 40:
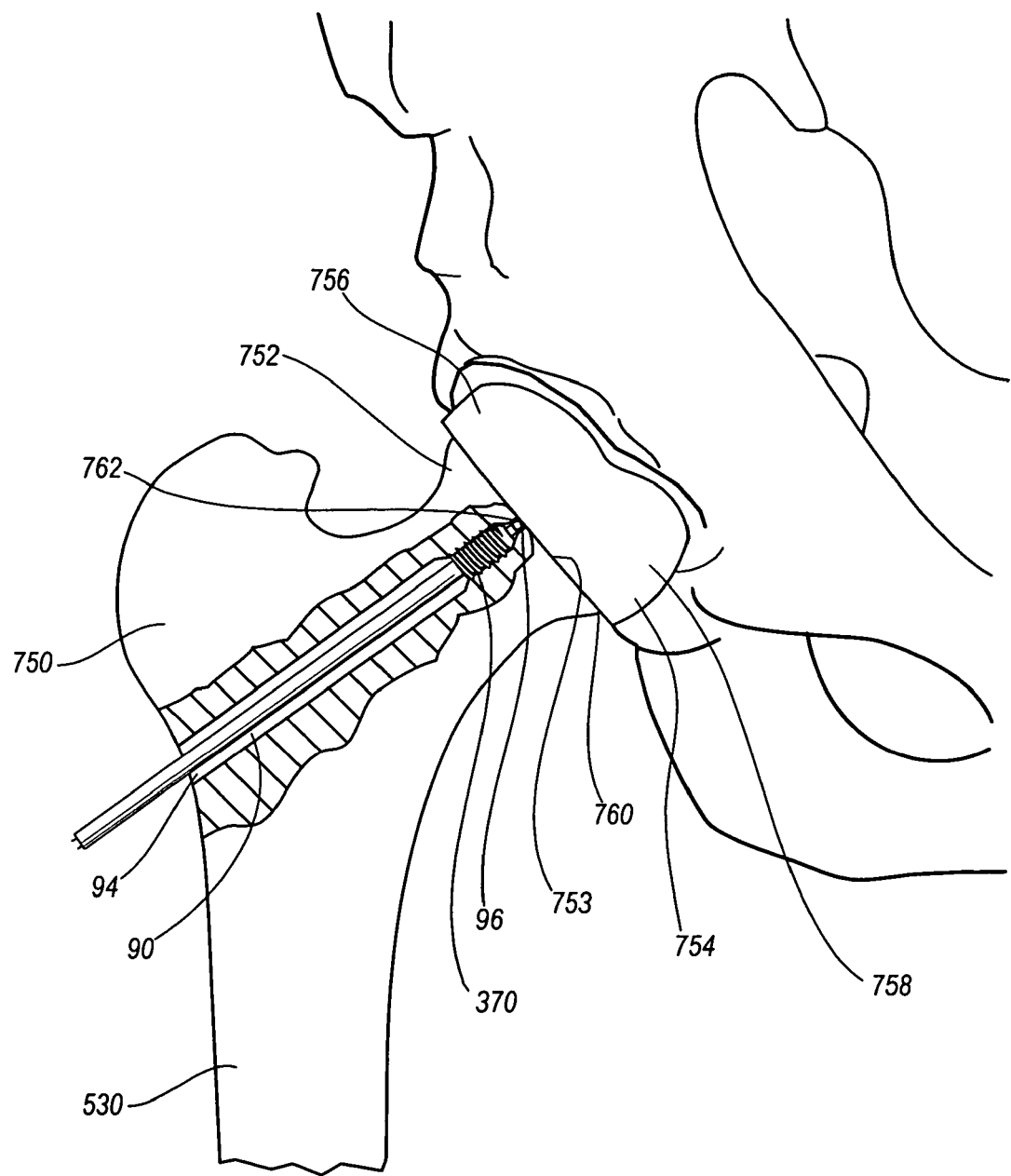
FIG. 40 is a partial cross sectional side view of an inventive implant mounted on the proximal end of a femur.
Figure 41:
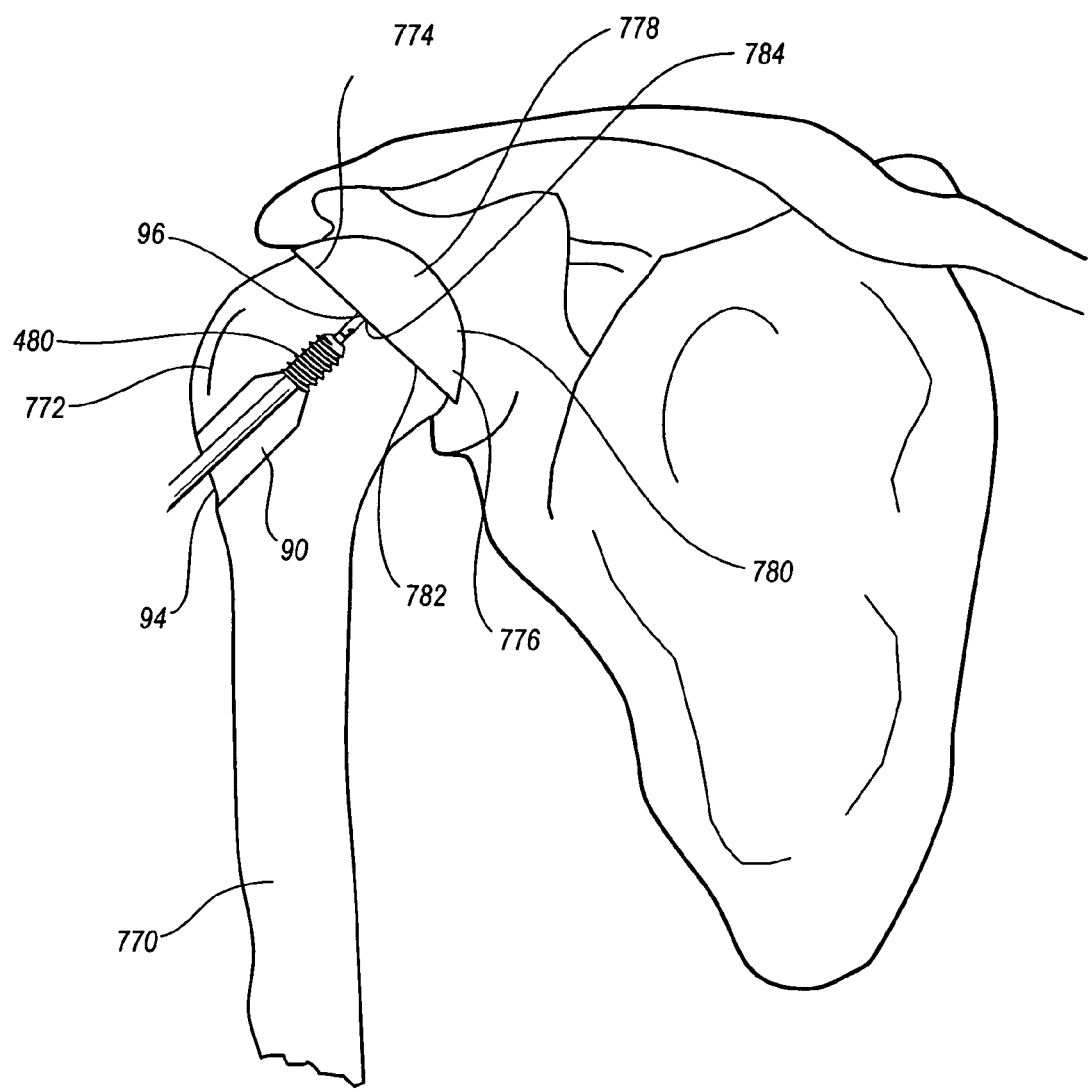
FIG. 41 is a partial cross sectional side view of an inventive implant mounted on the proximal end of a humerus.
Figure 42:
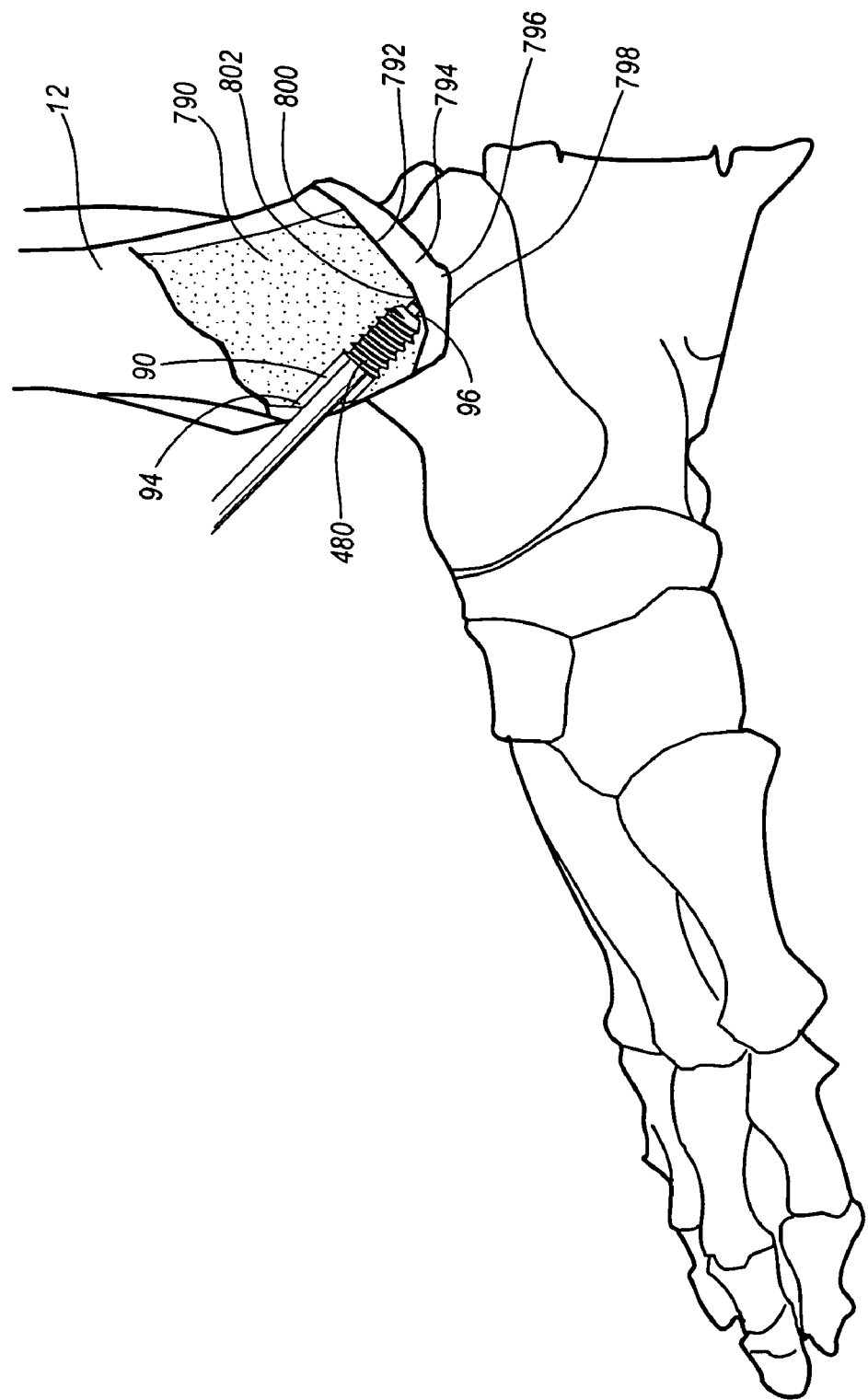
FIG. 42 is a partial cross sectional side view of an inventive implant mounted on the distal end of a tibia.

Depicted in FIGS. 40-42 are still other examples of inventive implants mounted on resected articulating surfaces of other orthopedic joints. For example, depicted in FIG. 40 is femur 530 having a proximal end 750 that would normally terminate at a femoral head 752 having an articulating surface. In the depicted drawing, femoral head 752 has been resected to from a resected articulating surface 753. In each of the embodiments depicted in FIGS. 40-42, it is appreciated that the resected articulating surface can be formed using conventional techniques or by using a modified rasp assembly of the present invention in combination with tunnel 90.

A proximal femoral implant 754 is shown mounted on resected articulating surface 753. Implant 754 comprises a body 756 having an articular surface 758 and an opposing bone apposition surface 760. Articular surface 758 engages with the acetabular socket while bone apposition surface 760 biases against resected articulating surface 753.

Tunnel 90 is formed on femur 530. Second end 96 of tunnel 90 is formed on resected articulating surface 753 while first end 94 of tunnel 90 is formed on the shaft of femur 530 at a location spaced apart from resected articulating surface 753. A threaded socket 762 is formed on bone apposition surface 760 of implant 754. Socket 762 can be replaced with stem 304 or other alternatives as discussed herein. Socket 762 is aligned with second end 96 of tunnel 90. Anchor assembly 370 is disposed within tunnel 90 and is coupled with implant 754 through socket 762 so as to secure implant 754 to femur 530.

Depicted in FIG. 41 is a humerus 770 having a proximal end 772 that would normally terminate at a humerus head having an articulating surface. In the depicted drawing, the humerus head has been resected to form a resected articulating surface 774. A proximal humerus implant 776 is shown mounted on resected articulating surface 774. Implant 776 comprises a body 778 having an articular surface 780 and an opposing bone apposition surface 782. Articular surface 780 engages with the scapula while bone apposition surface 782 biases against resected articulating surface 774.

Tunnel 90 is formed on humerus 770. Second end 96 of tunnel 90 is formed on resected articulating surface 774 while first end 94 of tunnel 90 is formed on the shaft of humerus 770 at a location spaced apart from resected articulating surface 774. A threaded socket 784 is formed on bone apposition surface 782 of implant 776. Socket 784 is aligned with second end 96 of tunnel 90. Anchor assembly 480 is disposed within tunnel 90 and is coupled with implant 776 through socket 784 so as to secure implant 776 to humerus 770.

Depicted in FIG. 42 is tibia 12 having a distal end 790 that would normally terminate at an articulating surface such as the inferior articular surface and the malleolar articular surface. In the depicted drawing, distal end 790 of tibia 12 has been resected to form a resected articulating surface 792. A distal tibial implant 794 is shown mounted to resected articulating surface 792. Implant 794 comprises a body 796 having an articular surface 798 and an opposing bone apposition surface 800. Articular surface 798 engages with the talus or an implant thereat while bone apposition surface 800 biases against resected articulating surface 792.

Tunnel 90 is formed on tibia 12. Second end 96 of tunnel 90 is formed on resected articulating surface 798 while first end 94 of tunnel 90 is formed on tibia 12 at a location proximally spaced apart from resected articulating surface 792. A threaded socket 802 is formed on bone apposition surface 800 of implant 794. Socket 802 is aligned with second end 96 of tunnel 90. Anchor assembly 480 is disposed within tunnel 90 and is coupled with implant 794 through socket 802 so as to secure implant 794 to tibia 12.

Set forth above are several different embodiments of the present invention. It is appreciated that the different features of the different embodiments can be mixed and matched to produce a variety of other embodiments within the scope of the present invention. By way of example and not by limitation, each of the different implants can be made with or without an inlay of porous bone ingrowth material on the bone apposition surface; each different implant can be made with a projecting stem or flush socket to receive a fastener; each different implant can be configured to mate with one or more different fasteners; and each different implant can be made as an integral body or two or more separate parts. For example, each implant can comprise a metal tray that is mounted to the bone and a plastic bearing plate that is mounted to the tray. It is likewise appreciated that the different methods steps for the different embodiments can also be mixed and matched and used with other techniques. Finally, it is again noted that the implants described herein are only by way of example and not by limitation. The present invention can also be used in association with resurfacing articulating surfaces of other orthopedic joints.

Finally, the above embodiments primarily discuss mounting implants on resected articulating surfaces. On occasion, however, a sufficient portion of a natural articulating surface has been worn down or otherwise removed by events other than surgical resection so that it is not necessary to resect the wear surface which is still functioning as a natural articulating surface. On these occasions, it is envisioned that the implant can be mounted directly on the worn natural articulating surface with minimal or no surgical resection of the articulating surface.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implant system for resurfacing at least a portion of an articulating surface of a bone, the system comprising:
    an implant having a top articular surface and an opposing bone apposition surface, the implant comprising:
        a lower bearing plate; and
        an upper bearing plate having the top articular surface formed thereon, one of the lower bearing plate and upper bearing plate having a track formed thereon while the other has a key that slidably rides within the track;
    an elongated fastener configured to rigidly mount to the implant so as to outwardly project from the bone apposition surface and prevent pivoting movement of the implant with respect to the fastener; and
    a tubular bone anchor adapted to encircle at least a portion of the fastener, the bone anchor comprising one or more threads or barbs formed on an exterior surface thereof.

2. An implant system as recited in claim 1, wherein the implant further comprises a stem projecting from the bone apposition surface, the stem being threaded to mate with the fastener.

3. An implant system as recited in claim 1, wherein the implant has a socket formed on the bone apposition surface, the socket being threaded to mate with the fastener.

4. An implant system as recited in claim 1, wherein the
    bearing plate has a bottom surface disposed opposite said top articular surface, a pocket being formed on the bottom surface of the bearing plate,
    an inlay of porous bone ingrowth material secured within the pocket.

5. An implant system as recited in claim 1, wherein the fastener comprises an elongated shaft having a length in a range between about 5 mm to about 15 mm.

6. An implant system as recited in claim 1, wherein the fastener comprises an elongated shaft having an enlarged head integrally formed thereon.

7. An implant system as recited in claim 1, further comprising an enlarged crown nut removably mountable to the fastener.

8. An implant system as recited in claim 7, wherein the crown nut is rotatable relative to the bone anchor.

9. An implant system as recited in claim 7, further comprising means for attaching an attachment tool to the crown nut.

10. An implant system as recited in claim 9, wherein the means for attaching the attachment tool comprises a plurality of prongs formed on the crown nut.

11. An implant system as recited in claim 1, wherein the fastener has at least one helical thread that engages with the implant and the bone anchor has at least one external helical thread, the helical thread of the bone anchor rotating in a direction opposite of the helical thread of the fastener.

12. An implant system as recited in claim 1, wherein the bone anchor has an interior surface bounding a channel extending between a first end and an opposing second end, the first end terminating at a first end face, the channel comprising a first channel portion extending from the first end, a second channel portion extending from the second end, and a radially inwardly projecting shoulder disposed between the first channel portion and the second channel portion.

13. An implant system as recited in claim 12, wherein the fastener comprises a shaft having an enlarged head integrally formed thereon, the head being biased against the shoulder of the bone anchor.

14. An implant system as recited in claim 12, further comprising an enlarged crown nut removably mounted on the fastener and biased against the shoulder of the bone anchor.

15. An implant system as recited in claim 1, further comprising a drive rod integrally formed with the fastener, a plurality of spaced apart annular breaking grooves being formed at the intersection between the fastener and the drive rod.

16. An implant system as recited in claim 1, wherein the fastener is configured to rigidly mount to the implant by threadedly engaging with the implant.

17. An implant system as recited in claim 1, wherein the fastener has at least one helical thread that engages with the implant.

18. An implant system as recited in claim 1, wherein the fastener has a proximal end and an opposing distal end, the distal end being mounted to the implant and the proximal end projecting away from the bone apposition surface of the implant, and wherein the implant system further comprises means for attaching a fastener driver to the proximal end of the fastener.

19. An implant system as recited in claim 18, wherein the means for attaching a fastener driver comprises a blind socket formed in the proximal end of the fastener.

20. An implant system as recited in claim 1, wherein the fastener has a first helical thread and the implant has a second helical thread and the fastener is rigidly mounted to the implant by threaded connection between the first and second helical threads.

21. An implant system for resurfacing at least a portion of an articulating surface of a bone, the system comprising:
    an implant having a top articular surface and an opposing bone apposition surface, the implant comprising:
        a tray having the bone apposition surface; and
        a bearing plate mounted on the tray, the bearing plate being comprised of a polymeric material and having the top articular surface;
    an elongated fastener configured to rigidly mount to the implant so as to outwardly project from the bone apposition surface and prevent pivoting movement of the implant with respect to the fastener; and
    a tubular bone anchor adapted to encircle at least a portion of the fastener, the bone anchor comprising one or more threads or barbs formed on an exterior surface thereof.

22. An implant system as recited in claim 21, wherein the implant further comprises a stem projecting from the bone apposition surface, the stem being threaded to mate with the fastener.

23. An implant system as recited in claim 21, wherein the implant has a socket formed on the bone apposition surface, the socket being threaded to mate with the fastener.

24. An implant system as recited in claim 21, wherein the
    bearing plate has a bottom surface disposed opposite said top articular surface, a pocket being formed on the bottom surface of the bearing plate,
    an inlay of porous bone ingrowth material secured within the pocket.

25. An implant system as recited in claim 21, wherein the fastener comprises an elongated shaft having a length in a range between about 5 mm to about 15 mm.

26. An implant system as recited in claim 21, wherein the fastener comprises an elongated shaft having an enlarged head integrally formed thereon.

27. An implant system as recited in claim 21, further comprising an enlarged crown nut removably mountable to the fastener.

28. An implant system as recited in claim 27, wherein the crown nut is rotatable relative to the bone anchor.

29. An implant system as recited in claim 27, further comprising means for attaching an attachment tool to the crown nut.

30. An implant system as recited in claim 29, wherein the means for attaching the attachment tool comprises a plurality of prongs formed on the crown nut.

31. An implant system as recited in claim 21, wherein the fastener has at least one helical thread that engages with the implant and the bone anchor has at least one external helical thread, the helical thread of the bone anchor rotating in a direction opposite of the helical thread of the fastener.

32. An implant system as recited in claim 21, wherein the bone anchor has an interior surface bounding a channel extending between a first end and an opposing second end, the first end terminating at a first end face, the channel comprising a first channel portion extending from the first end, a second channel portion extending from the second end, and a radially inwardly projecting shoulder disposed between the first channel portion and the second channel portion.

33. An implant system as recited in claim 32, wherein the fastener comprises a shaft having an enlarged head integrally formed thereon, the head being biased against the shoulder of the bone anchor.

34. An implant system as recited in claim 32, further comprising an enlarged crown nut removably mounted on the fastener and biased against the shoulder of the bone anchor.

35. An implant system as recited in claim 21, further comprising a drive rod integrally formed with the fastener, a plurality of spaced apart annular breaking grooves being formed at the intersection between the fastener and the drive rod.

36. An implant system as recited in claim 21, wherein the fastener is configured to rigidly mount to the implant by threadedly engaging with the implant.

37. An implant system as recited in claim 21, wherein the fastener has at least one helical thread that engages with the implant.

38. An implant system as recited in claim 21, wherein the fastener has a proximal end and an opposing distal end, the distal end being mounted to the implant and the proximal end projecting away from the bone apposition surface of the implant, and wherein the implant system further comprises means for attaching a fastener driver to the proximal end of the fastener.

39. An implant system as recited in claim 38, wherein the means for attaching a fastener driver comprises a blind socket formed in the proximal end of the fastener.

40. An implant system as recited in claim 21, wherein the tray further comprises a top surface opposite the bone apposition surface and the means for securing the fastener is configured so as to be inaccessible from the top surface of the tray.

41. An implant system as recited in claim 21, wherein the fastener has a first helical thread and the implant has a second helical thread and the fastener is rigidly mounted to the implant by threaded connection between the first and second helical threads.

42. An implant for resurfacing at least a portion of an articulating surface of a bone, the implant comprising:
a body having a first side with a top articular surface and an opposing second side with a bone apposition surface, the bone apposition surface being adapted to bias against a natural or resected articulating surface of a bone, the body comprising:
a tray having the bone apposition surface; and
a bearing plate mounted on the tray, the bearing plate being comprised of a polymeric material and having the top articular surface; and
means for securing a fastener to the second side of the body after the bone apposition surface is biased against the natural or resected articulating surface such that the fastener is rigidly fixed to the body so as to prevent pivoting movement of the body with respect to the fastener and such that applying increased tension to the fastener increases a force at which the bone apposition surface biases against the natural or resected articulating surface.

43. An implant as recited in claim 42, wherein the tray further comprises a top surface opposite the bone apposition surface and the means for securing the fastener is configured so as to be inaccessible from the top surface of the tray.

* * * * *